US012138273B2

(12) United States Patent
Sharp et al.

(10) Patent No.: US 12,138,273 B2
(45) Date of Patent: *Nov. 12, 2024

(54) ABIRATERONE PRODRUGS

(71) Applicant: Propella Therapeutics, Inc., Pittsboro, NC (US)

(72) Inventors: Matthew J. Sharp, Apex, NC (US); William R. Moore, Jr., Pittsboro, NC (US)

(73) Assignee: PROPELLA THERAPEUTICS, INC., Pittsboro, NC (US)

( * ) Notice: Subject to any disclaimer, the term of this patent is extended or adjusted under 35 U.S.C. 154(b) by 106 days.

This patent is subject to a terminal disclaimer.

(21) Appl. No.: 18/098,798

(22) Filed: Jan. 19, 2023

(65) Prior Publication Data

US 2023/0233582 A1    Jul. 27, 2023

Related U.S. Application Data

(63) Continuation of application No. 16/989,304, filed on Aug. 10, 2020, now Pat. No. 11,559,534, which is a continuation of application No. 16/808,912, filed on Mar. 4, 2020, now Pat. No. 10,792,292.

(60) Provisional application No. 62/849,259, filed on May 17, 2019, provisional application No. 62/814,568, filed on Mar. 6, 2019.

(51) Int. Cl.
| A61K 31/58 | (2006.01) |
| A61K 9/00  | (2006.01) |
| A61K 47/14 | (2017.01) |
| A61K 47/44 | (2017.01) |

(52) U.S. Cl.
CPC ............ *A61K 31/58* (2013.01); *A61K 9/0019* (2013.01); *A61K 47/14* (2013.01); *A61K 47/44* (2013.01)

(58) Field of Classification Search
None
See application file for complete search history.

(56) References Cited

U.S. PATENT DOCUMENTS

| 5,604,213 | A  | 2/1997  | Barrie et al. |
| 5,618,807 | A  | 4/1997  | Barrie et al. |
| 8,338,588 | B2 | 12/2012 | Hunt |
| 8,791,095 | B2 | 7/2014  | Casebier |
| 8,822,438 | B2 | 9/2014  | Auerbach et al. |
| 8,975,244 | B2 | 3/2015  | Marom et al. |
| 9,353,145 | B2 | 5/2016  | Derrien et al. |
| 9,359,395 | B2 | 6/2016  | Casebier |
| 9,737,540 | B2 | 8/2017  | Davies |
| 9,889,144 | B2 | 2/2018  | Murphy et al. |
| 9,937,259 | B2 | 4/2018  | Sun |
| 10,087,212 | B2 | 10/2018 | Xing et al. |
| 10,292,990 | B2 | 5/2019  | Nemeth et al. |
| 10,792,292 | B2 | 10/2020 | Sharp et al. |
| 11,559,534 | B2 | 1/2023  | Sharp et al. |
| 11,957,696 | B2 | 4/2024  | Sharp |
| 2005/0159361 | A1 | 7/2005  | Hara |
| 2009/0124587 | A1 | 5/2009  | Auerbach et al. |
| 2011/0129423 | A1 | 6/2011  | Frincke |
| 2011/0312916 | A1 | 12/2011 | Casebier |
| 2014/0011992 | A1 | 1/2014  | Perez Encabo et al. |
| 2015/0005265 | A1 | 1/2015  | Stewart |
| 2015/0005268 | A1 | 1/2015  | Auerbach |
| 2015/0337003 | A1 | 11/2015 | Koziol et al. |
| 2016/0228456 | A1 | 8/2016  | Cornfeld et al. |
| 2017/0216443 | A1 | 8/2017  | Sun |
| 2018/0030085 | A1 | 2/2018  | Xing |
| 2019/0040098 | A1 | 2/2019  | Wang et al. |
| 2019/0151458 | A1 | 5/2019  | Ciufolini et al. |
| 2019/0275170 | A1 | 9/2019  | Benenato |
| 2019/0315797 | A1 | 10/2019 | Sun et al. |
| 2020/0237784 | A1 | 7/2020  | Wang et al. |
| 2020/0281945 | A1 | 9/2020  | Sharp et al. |
| 2022/0265681 | A1 | 8/2022  | Sharp et al. |

FOREIGN PATENT DOCUMENTS

| CA | 3133620 A1    | 9/2020 |
| CN | 101044155 A   | 9/2007 |
| CN | 102686600 A   | 9/2012 |
| CN | 104017045 A   | 9/2014 |
| CN | 104447394 A   | 3/2015 |
| CN | 105646637     | 6/2016 |
| CN | 105646637 A   | 6/2016 |
| CN | 106977577 A   | 7/2017 |
| CN | 113929727 A   | 1/2022 |
| EA | 025518 B9     | 12/2016 |
| EP | 3610876 A1    | 2/2020 |
| JP | 2004002321 A  | 1/2004 |
| JP | 2005533036 A  | 11/2005 |
| JP | 2008546713 A  | 12/2008 |

(Continued)

OTHER PUBLICATIONS

Avitia, J., et al., "A Phase 1 Study of PRL-02, a Long-Acting IM Depot Injection of Abiraterone Decanoate in Patients with Prostate Cancer," Presented at the 2022 ESMO Congress, Sep. 9-13, 2022, Paris, France, Propella Therapeutics, Inc.

Moore, W., et al., "Abiraterone decanoate (PRL-02): Pharmacology of a single intramuscular (IM) depot injection compared to oral abiraterone acetate (AA) in intact male rats (Abstract #160)," 2022 Genitourinary Cancers Symposium, Propella Therapeutics, Inc. (Feb. 17, 2022).

(Continued)

*Primary Examiner* — Zinna Northington-Davis

(74) *Attorney, Agent, or Firm* — Nixon & Vanderhye, PC

(57) ABSTRACT

Sustained-release abiraterone prodrug formulations, methods, and kits for parenteral administration to a subject having a sex hormone-dependent benign or malignant disorder such as prostate cancer, a syndrome due to androgen excess, and/or a syndrome due to glucocorticoid excess such as hypercortisolemia.

34 Claims, 28 Drawing Sheets

(56) References Cited

FOREIGN PATENT DOCUMENTS

| | | |
|---|---|---|
| JP | 2010501575 A | 1/2010 |
| JP | 2018505206 A | 2/2018 |
| RU | 2013132766 A | 1/2015 |
| RU | 2015144285 A | 4/2017 |
| WO | 03101539 A1 | 12/2003 |
| WO | 2006138608 A2 | 12/2006 |
| WO | 2008024484 A1 | 2/2008 |
| WO | 2011083830 A1 | 7/2011 |
| WO | WO-2013158644 A2 | 10/2013 |
| WO | WO-2013159225 A1 | 10/2013 |
| WO | WO-2014009434 A1 | 1/2014 |
| WO | WO2014111815 A2 | 7/2014 |
| WO | WO-2014145813 A1 | 9/2014 |
| WO | WO-2015038649 A1 | 3/2015 |
| WO | WO-2015134464 A2 | 9/2015 |
| WO | WO-2015143004 A2 | 9/2015 |
| WO | WO-2016044701 A1 | 3/2016 |
| WO | WO-2016050116 A1 | 4/2016 |
| WO | WO-2016082792 A1 | 6/2016 |
| WO | WO2017106957 A1 | 6/2017 |
| WO | WO2020180942 A1 | 9/2020 |
| WO | WO2022051330 A1 | 3/2022 |
| WO | WO2022174134 A1 | 8/2022 |
| WO | 2023038933 A1 | 3/2023 |

OTHER PUBLICATIONS

Propella Therapeutics Corporate Presentation at the 11th Annual LifeSci Partners Corporate Access Event (Jan. 5-7, 2022), 26 pages, last accessed at https://propellatx.com/category/presentations/ on Mar. 27, 2023.

Warneke, T., et al., "Abstract 337037: A Phase ½a, Open-label, Multicenter Study of Intramuscular Abiraterone Decanoate (PRL-02) Depot in Patients with Advanced Prostate Cancer (NCT04729114)," ASCO Poster, Propella Therapeutics, Inc. (Jun. 4, 2021).

Pouton, C. W., "Formulation of self-emulsifying drug delivery systems," Advanced Drug Delivery Reviews, 25:47-58 (1997).

Presentation at the MedInvest Oncology Conference (Dec. 7-10, 2021): Propella Therapeutics Corporate Presentation, 26 pages, last accessed at https://propellatx.com/category/presentations/ on Mar. 27, 2023.

Zafeiriou, Managing Metastatic Prostate Cancer in Your Urological Oncology Practice, Springer International Publishing AG, XP093127386, May 9, 2016.

Warneke, "A phase 1 /2a, open-label, multicenter study of intramuscular (IM) abiraterone decanoate (PRL-02) depot in patients with advanced prostate cancer (NCT04729114). Journal of Clinical Oncology", Jan. 1, 2021, XP093051039, Retrieved from the Internet: URL:https://ascopubs.org/doi/10.1200/JC0.2021.39.15_suppl. TPS5090.

Moore, "Abiraterone decanoate (AD): Potent and long-acting activity of a novel intramuscular (IM) abiraterone prodrug depot in a castrate monkey model. Journal of Clinical Oncology", Jan. 1, 2021, XP2805809, Retrieved from the Internet: URL:https://ascopubs.org/doi/10.1200/JC0.2021.39.6_suppl.78.

Moore, "Abiraterone decanoate (PRL-02): Pharmacology of a single intramuscular (IM) depot injection compared to oral abiraterone acetate (AA) in intact male rats. Journal of Clinical Oncology", Feb. 16, 2022, XP9544705, Retrieved from the Internet: URL:https://ascopubs.org/doi/10.1200/JC0.2022.40.6_suppl. 160.

Benoist GE, Hendriks RJ, Mulders PF, Gerritsen WR, Somford DM, Schalken JA, van Oort IM, Burger DM, van Erp NP (Nov. 2016). "Pharmacokinetic Aspects of the Two Novel Oral Drugs Used for Metastatic Castration-Resistant Prostate Cancer: Abiraterone Acetate and Enzalutamide". Clin Pharmacokinet.

"Zytiga abiraterone acetate product information" (PDF). TGA eBusiness Services. Janssen-Cilag Pty Ltd. Mar. 1, 2012.

Li, Z., Bishop, A., Alyamani, M et al. Conversion of abiraterone to D4A drives anti-tumour activity in prostate cancer. Nature. Jul. 16, 2015; 523(7560): 347-351. doi:10.1038/nature14406.

Zytiga® (abiraterone acetate) tablets Prescribing Information, the Food and Drug Administration, 2018.

Larsen, S. W. and Larsen, C., "Critical Factors Influencing the In Vivo Performance of Long-acting Lipophilic Solutions—Impact on In Vitro Release Method Design," AAPS J., 11(4):762-770 (2009).

Minto, C. F., et al., "Pharmacokinetics and Pharmacodynamics of Nandrolone Esters in Oil Vehicle: Effects of Ester, Injection Site and Injection Volume," J Pharmacol Exp Ther., 281(1):93-102 (1997).

Tanaka, T., et al., "Intramuscular Absorption of Drugs from Oily Solutions in the Rat," Chem Pharm Bull., 22(6):1275-1284 (1974).

Chang, S.-C. and Lee, V. H. L., "Influence of chain length on the in vitro hydrolysis of model ester prodrugs by ocular esterases," Current Eye Research, 2(10):651-656 (1982).

Forsdahl, G., et al., "Detection of testosterone esters in blood," Drug Testing and Analysis, 7(11-12):983-989 (2015).

U.S. Appl. No. 17/635,106, filed Feb. 14, 2022, Sharp et al., related application.

U.S. Appl. No. 17/670,712, filed Feb. 14, 2022, SHARP et al., related application.

ABIRATERONE PRODRUGS

This application is a continuation of U.S. patent application Ser. No. 16/989,304, filed Aug. 10, 2020, which is a continuation of U.S. patent application Ser. No. 16/808,912, filed Mar. 4, 2020, which claims the benefit of U.S. Provisional Application Nos. 62/814,568, filed Mar. 6, 2019, and 62/849,259, filed May 17, 2019, the content of each of which is incorporated herein by reference in its entirety.

The present disclosure relates generally to novel prodrugs of abiraterone and long-acting, depot-based parenteral formulations of abiraterone prodrugs. The disclosure is subject to a wide range of applications, such as for intramuscular (IM) injection to a patient suffering from an androgen or estrogen hormone-dependent benign or malignant disorder, including various cancers (such as prostate cancer, bladder cancer, hepatocellular carcinoma, lung cancer, breast cancer, and ovarian cancer, etc.), and for the treatment of non-oncologic syndromes due to the overproduction of androgens (including both classical and nonclassical congenital adrenal hyperplasia, endometriosis, polycystic ovary syndrome precocious puberty, hirsutism, etc.) or due to the overproduction of glucocorticoids, typically cortisol in conditions such as Cushing's syndrome or Cushing's disease.

BACKGROUND

Abiraterone ((3β)-17-(pyridin-3-yl) androsta-5, 16-dien-3-ol; CAS #: 154229-19-3); Formula: $C_{24}H_{31}NO$; Mol. Weight: 349.5 g/mol) is an inhibitor of CYP17A1 (which is a member of the cytochrome P450 superfamily of enzymes that catalyze the synthesis of cholesterol, steroids and other lipids and are involved in drug metabolism). CYP17A1 has both 17α-hydroxylase activity and 17,20-lyase activity. Abiraterone potently and selectively inhibits both CYP17A1 17α-hydroxylase and 17,20-lyase enzyme activities. The 17α-hydroxylase activity of CYP17A1 is required for the generation of glucocorticoids such as cortisol. However, both the hydroxylase and 17,20-lyase activities of CYP17A1 are required for the production of androgenic (e.g., androstenedione, testosterone, and dihydrotestosterone) and estrogenic (estrone, estradiol. estratriol) steroids through the conversion of 17α-hydroxypregnenolone to the sex steroid precursor, dehydroepiandrosterone, see FIG. 14D. Thus, abiraterone interferes with the synthesis of androgens and estrogens in the gonads (primarily in the testes and ovaries) and extra-gonadally (e.g., in the adrenals and in the tumors themselves).

Though abiraterone itself is poorly absorbed, it can be administered orally as an abiraterone acetate prodrug. Abiraterone acetate is also poorly absorbed, but can be converted to abiraterone in the gut, which is poorly absorbed into the bloodstream following the cleavage of the acetate prodrug. Abiraterone acetate ((3β)-17-(3-Pyridyl)androsta-5, acetate; CAS #154229-18-2) is approved in the United States for treatment of castration resistant or castration sensitive prostate cancer under the brand name Zytiga®. Abiraterone acetate is now also available globally.

It is known that orally-administered abiraterone acetate is not absorbed by the gastrointestinal tract (and is not detected in blood plasma). Instead, it has been shown that abiraterone acetate is hydrolyzed to abiraterone in the intraluminal environment resulting in generation of abiraterone supersaturation, which is responsible for creating the strong driving force for abiraterone absorption (Stappaerts et al., *Eur. J. Pharmaceutics Biopharmaceutics* 90:1, 2015).

Because abiraterone blocks the normal physiologic production of steroids by the adrenal glands, its prodrug formulation is commonly prescribed with administration of a low dose of a steroid to prevent adrenal insufficiency. Indeed, Zytiga® tablets (250 mg) are approved in the United States in combination with prednisone for the treatment of patients with metastatic castration resistant prostate cancer and patients with metastatic castration-sensitive prostate cancer. The prescribing information provided with Zytiga® recommends oral administration of 1,000 mg (4×250 mg tablets) once daily in combination with prednisone (5 mg) administered orally twice daily for castration resistant prostate cancer patients or once daily for castration sensitive prostate cancer patients. In Europe, the use of Zytiga® is approved in combination with either prednisone or prednisolone.

Because the administration of abiraterone acetate with food increases the absorption of abiraterone acetate (and, therefore, has the potential to result in increased and highly variable exposures, which can potentially cause various side effects including cardiovascular side effects and/or hepatotoxicity etc.), the prodrug should be consumed on an empty stomach at least one hour before, or two hours after, a meal. Indeed, the prescribing information for Zytiga® states it must be taken on an empty stomach, and no food should be consumed for at least two hours before oral dosing and at least one hour after oral dosing.

The prescribing information explains that for a daily oral dose of 1,000 mg of Zytiga® in patients with metastatic castration-resistant prostate cancer, abiraterone's steady-state $C_{max}$ values were 226±178 ng/mL (mean±SD) and its area under the curve (AUC) values were 1173±690 ng·hr/mL (mean±SD). A single-dose (1,000 mg) cross-over study of Zytiga® in healthy subjects found that systemic exposure of abiraterone was increased when Zytiga® was administered with food. Specifically, abiraterone's $C_{max}$ and AUC values were approximately 7- and 5-fold higher, respectively, when Zytiga® was administered with a low-fat meal (7% fat, 300 calories) and approximately 17- and 10-fold higher, respectively, when Zytiga® was administered with a high-fat meal (57% fat, 825 calories).

The currently approved solid dosage oral form of the prodrug abiraterone acetate has several disadvantages. For example, it has very low bioavailability that necessitates a large daily pill burden for patients (4×250 mg tablets once daily). In addition, it causes highly variable blood levels in patients due to the combination of low bioavailability and a large food effect. Further, as abiraterone is rapidly cleared, this approved dosing regimen results in a daily $C_{min}$ of abiraterone, which is believed to be associated with a loss of therapeutic effect in metastatic castration resistant prostate cancer patients.

Non-oral modes of administration (for example, parenteral routes) have been explored for other classes of drugs. However, to date, there are no sustained-release injectable prodrug formulations of abiraterone.

SUMMARY

In various embodiments, the present disclosure provides novel abiraterone prodrugs, long-acting abiraterone prodrug formulations, and methods of using the same, for example, in treating a subject having a sex hormone-dependent benign or malignant disorder and/or a syndrome due to androgen and/or glucocorticoid excess. Typically, the novel abiraterone prodrugs herein can be a fatty acid ester of abiraterone, which upon cleavage, releases abiraterone and a safe and degradable fatty acid component. As detailed herein, compared to oral abiraterone acetate formulation, the novel abiraterone prodrugs and formulations disclosed herein are a breakthrough in that they provide increased bioavailability, elimination of the food effect, reduced pill burden, less frequent dosing frequency, and sustained effective blood plasma levels of abiraterone, e.g., continuous plasma exposures above daily $C_{min}$ levels observed for oral administration of abiraterone acetate, for example, for at least one week, typically, for at least two weeks following administration of the abiraterone prodrug formulation. Further, pharmacokinetics and pharmacodynamics studies of representative abiraterone prodrugs herein, such as abiraterone decanoate or abiraterone isocaproate, demonstrate that the novel abiraterone prodrugs and formulations disclosed herein are suitable for dosing once a week, once a month, or even less frequently, for treating a subject having a sex hormone-dependent benign or malignant disorder, a syndrome due to androgen excess and/or a syndrome due to glucocorticoid excess described herein. This feature alone represents a significant improvement over the currently marketed Zytiga® tablets, which require a large daily pill burden for patients (4×250 mg tablets once daily).

Some embodiments of the present disclosure are directed to novel abiraterone prodrugs. In some embodiments, the abiraterone prodrug can be a compound of Formula I, or a pharmaceutically acceptable salt thereof:

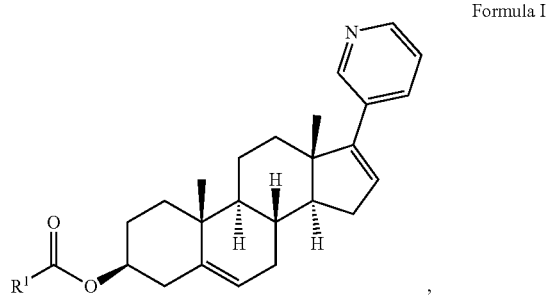

Formula I wherein $R^1$ is defined herein.

In one representative embodiment, an abiraterone prodrug formulation is provided for parenteral administration to a subject having a sex hormone-dependent benign or malignant disorder, a syndrome due to androgen excess, and/or a syndrome due to glucocorticoid (e.g., cortisol) excess. In one aspect, the formulation includes a lipophilic-ester form of abiraterone and one or more pharmaceutically acceptable carriers, diluents, or excipients (such that, for example, the prodrug formulation is present as a solution or suspension in a pharmaceutically acceptable oil, such as an oil of vegetable origin or a synthetic oil including synthetic mono- or di-glycerides of fatty acid; for example, the prodrug formulation can be present as a solution or suspension in vegetable oil and other co-solvents and excipients). In certain representative embodiments, the lipophilic-ester form of abiraterone can be an acetate, propionate, butanoate, valerate, caproate, enanthate, cypionate, isocaproate, buciclate, cyclohexanecarboxylate, phenyl propionate, decanoate or undecanoate. In some embodiments, the abiraterone prodrug formulation can include a compound of Formula II, or a pharmaceutically acceptable salt thereof:

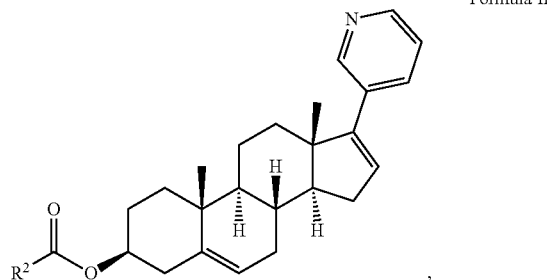

Formula II wherein $R^2$ is defined herein. In some embodiments, the abiraterone prodrug formulation can be formulated for intramuscular injection, intradermal injection, or subcutaneous injection. In some embodiments, the compound of Formula II or pharmaceutically acceptable salt thereof can be present in the formulation at a concentration of about 25 mg/ml to about 500 mg/ml.

Typically, upon administration of a formulation (e.g., the abiraterone prodrug formulation herein), a therapeutic blood plasma concentration of abiraterone is achieved and persists for at least one week, e.g., at least two weeks and up to four or more weeks. In one aspect, the therapeutic blood plasma concentration of abiraterone is at least 1 ng/ml, e.g., at least 1 ng/ml, at least 2 ng/ml, at least 4 ng/ml, or at least 8 ng/ml, following parenteral administration of the prodrug formulation. In some embodiments, the therapeutic blood plasma concentration of abiraterone can also be about 0.5 ng/ml or higher. Parenteral administration can be via IM injection, intradermal injection, or subcutaneous injection. In one aspect, the formulation is suitable for treatment of sex hormone-dependent benign or malignant disorders such as androgen-dependent disorders and estrogen-dependent disorders, such as androgen-dependent or estrogen-dependent cancers. The sex hormone-dependent benign or malignant disorders can include prostate cancer and breast cancer. Prostate cancer can include castration resistant prostate cancer and castration sensitive prostate cancer. In some embodiments, the sex hormone-dependent benign or malignant disorders can include various cancers such as ovarian cancer, bladder cancer, hepatocellular carcinoma, lung cancer, etc. Inhibition of CYP17A1 is expected to reduce androgen and glucocorticoid (e.g., cortisole) overproduction. The abiraterone prodrug formulation herein is not limited to the treatment of oncologic conditions described herein, but can also be used for the treatment of non-oncologic syndromes due to androgen and glucocorticoid (e.g., cortisole) excess. In one aspect, the formulation is suitable for treatment of non-oncologic syndromes due to androgen excess, such as endometriosis, polycystic ovary syndrome, congenital adrenal hyperplasia (e.g., classical or nonclassical congenital adrenal hyperplasia), precocious puberty, hirsutism, etc., and/or syndromes due to glucocorticoid (e.g., cortisole) excess such as Cushing's syndrome or Cushing's disease.

The parenteral formulations fulfill a long-felt and unmet need by providing an alternative to oral formulations that suffer from (1) low bioavailability, (2) interactions with ingested food, (3) delivery of highly variable blood levels of parent drug with the possibility of reduced efficacy and increased side effects, (4) requirement of daily dosing and high pill burden, and (5) poor patient compliance due to required abstinence from food within hours of administration, high pill burden, and the need for complementary daily administration of prednisone or prednisolone with a conflicting dosing schedule as it is to be taken with food.

One object of the present disclosure is to provide a method for inhibiting CYP17A1 activity such as inhibiting 17α-hydroxylase activity and 17,20-lyase activity, by parenterally administering to a subject in need thereof an effective dose of at least one abiraterone prodrug formulation. In some embodiments, the subject suffers from a sex hormone-dependent benign or malignant disorder, a syndrome due to androgen excess, and/or a syndrome due to glucocorticoid excess such as hypercortisolemia as described herein.

One object of the present disclosure is to provide a method for reducing the level of glucocorticoids (e.g., cortisol) by parenterally administering to a subject in need thereof an effective dose of at least one abiraterone prodrug formulation. In some embodiments, the subject suffers from a syndrome due to glucocorticoid excess, such as due to hypercortisolemia as described herein. In some embodiments, the subject suffers from Cushing's syndrome disorders or Cushing's disease.

One object of the present disclosure is to provide a method for reducing the level of androgens (e.g., testosterone and/or dihydrotestosterone) and/or estrogens by parenterally administering to a subject in need thereof an effective dose of at least one abiraterone prodrug formulation. In some embodiments, the subject suffers from a syndrome due to androgen excess, such as classical or nonclassical congenital adrenal hyperplasia, endometriosis, polycystic ovary syndrome precocious puberty, hirsutism, etc. In some embodiments, the subject suffers from an androgen and/or estrogen associated cancer, such as prostate cancer or breast cancer.

Another object is to provide a method for treating a sex hormone-dependent benign or malignant disorder, a syndrome due to androgen excess, and/or a syndrome due to glucocorticoid excess such as hypercortisolemia, by parenterally administering to a subject in need of such treatment an effective dose of at least one abiraterone prodrug formulation. In one representative embodiment, the method is for treating a sex hormone-dependent benign or malignant disorder, which is an androgen-dependent disorder or an estrogen-dependent disorder, such as an androgen-dependent cancer or an estrogen-dependent cancer. The sex hormone-dependent benign or malignant disorder can include prostate cancer or breast cancer. Prostate cancer can include castration resistant prostate cancer and castration sensitive prostate cancer. In some embodiments, the sex hormone-dependent benign or malignant disorder can also include ovarian cancer, bladder cancer, hepatocellular carcinoma, lung cancer, etc. In one representative embodiment, the method is for treating a non-oncologic syndrome due to androgen excess, such as endometriosis, polycystic ovary syndrome, congenital adrenal hyperplasia (e.g., classical or nonclassical congenital adrenal hyperplasia), precocious puberty, hirsutism, etc., and/or a syndrome due to glucocorticoid (e.g., cortisole) excess such as Cushing's syndrome or Cushing's disease.

In some embodiments, the abiraterone prodrug formulation can include at least one compound of Formula I or II, or a pharmaceutically acceptable salt thereof. In one aspect, the formulation includes a lipophilic-ester form of abiraterone and one or more pharmaceutically acceptable carriers, diluents, or excipients. In certain representative embodiments, the lipophilic-ester form of abiraterone can be, for example, an acetate, propionate, butanoate, valerate, caproate, enanthate, cypionate, isocaproate, buciclate, cyclohexanecarboxylate, phenyl propionate, decanoate or undecanoate. Upon administration of a formulation to a subject in need thereof, a therapeutic blood plasma concentration of abiraterone is achieved and persists for at least one week, e.g., at least two weeks and up to four or more weeks. In one aspect, the therapeutic blood plasma concentration of abiraterone is at least 1 ng/ml, e.g., at least 1 ng/ml, at least 2 ng/ml, at least 4 ng/ml, or at least 8 ng/ml, following parenteral administration of the prodrug formulation. In some embodiments, the therapeutic blood plasma concentration of abiraterone can also be about 0.5 ng/ml or higher. Parenteral administration can be via IM injection, intradermal injection, or subcutaneous injection. In certain embodiments, the method can include once-monthly administration of at least one abiraterone prodrug formulation. In one aspect, at least one abiraterone prodrug formulation can be administered in a divided dose. In another representative embodiment, at least one abiraterone prodrug formulation can be administered simultaneously with one or more different prodrug formulations and/or at least one other drug or agent (for example, another cancer chemotherapeutic drug, hormone replacement drug, or hormone ablation drug). In certain aspects, at least one abiraterone prodrug formulation can be administered before at least one other drug or agent. Alternatively, at least one abiraterone prodrug formulation can be administered after at least one other drug or agent. In other representative embodiments, more than one administration of one or more formulations can be performed over the course of several days, weeks, months, or years to provide initial and continual treatment of a sex hormone-dependent benign or malignant disorder (such as prostate cancer), a syndrome due to androgen excess, and/or a syndrome due to glucocorticoid excess such as hypercortisolemia. In other representative embodiments, at least one abiraterone prodrug formulation can contain at least two different lipophilic-ester forms of abiraterone and the formulation can be administered simultaneously with one or more different prodrug formulations and/or at least one other drug or agent (for example, another cancer chemotherapeutic drug, hormone replacement drug, or hormone ablation drug). In certain aspects, at least one abiraterone prodrug formulation can contain at least two different lipophilic-ester forms of abiraterone and the formulation can be administered before at least one other drug or agent. Alternatively, at least one abiraterone prodrug formulation can contain at least two different lipophilic-ester forms of abiraterone and the formulation can be administered after at least one other drug or agent. In other representative embodiments, more than one administration of one or more formulations containing at least two different lipophilic-ester forms of abiraterone can be performed over the course of several days, weeks, months, or years to provide initial and continual treatment of a sex hormone-dependent benign or malignant disorder (such as prostate cancer), a syndrome due to androgen excess, and/or a syndrome due to glucocorticoid excess such as hypercortisolemia. The lipophilic-ester forms of abiraterone can be chosen from among, for example, an acetate, propionate, butanoate, valerate, caproate, enanthate, cypionate, isocaproate, buciclate, cyclohexanecarboxylate, phenyl propionate, decanoate or undecanoate.

Another object is to provide a kit for treating a subject with a sex hormone-dependent benign or malignant disorder (such as prostate cancer), a syndrome due to androgen excess, and/or a syndrome due to glucocorticoid excess such as hypercortisolemia. In a representative embodiment, the kit includes a container such as a vial, an ampule, or a preloaded syringe, containing one or more formulations. In another representative embodiment, the kit includes a container such as a vial, an ampule, or a preloaded syringe, containing one or more formulations and at least one other drug or agent capable of enhancing the efficacy of the formulation(s) or decreasing an undesirable side effect(s) of the formulation(s). In other representative embodiments, the kit includes a container such as a vial, an ampule, or a preloaded syringe containing one or more formulations and at least one other drug or agent capable of enhancing the efficacy of the formulation(s) or decreasing an undesirable side effect(s) of the formulations. It is understood that the formulations can contain one lipophilic-ester form of abiraterone or two or more different lipophilic-ester forms of abiraterone. A person skilled in the art would understand that kits and packages can be prepared including one, all, or any combination of a formulation, diluent, buffer, adjuvant, pharmaceutically-acceptable carrier, and at least one other drug or agent capable of enhancing the efficacy of a formulation or decreasing an undesirable side effect of a formulation.

Another object is to provide a method for preparing an abiraterone decanoate formulation suitable for parenteral administration to a subject having a sex hormone-dependent benign or malignant disorder, a syndrome due to androgen excess, and/or a syndrome due to glucocorticoid excess such as hypercortisolemia.

These and other objects can be achieved in certain embodiments.

In some embodiments, the disclosure provides:

[1] a compound of Formula I, or a pharmaceutically acceptable salt thereof,

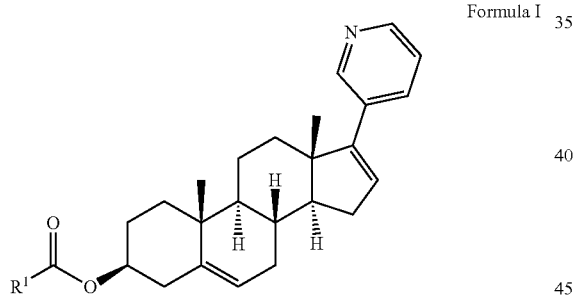

Formula I wherein $R^1$ is $R^{10}$, $O—R^{10}$, or $NHR^{10}$,
wherein $R^{10}$ is selected from:
a $C_{7-30}$ alkyl; a $C_{7-30}$ alkenyl; a $C_{7-30}$ alkynyl; an alkyl substituted with a cycloalkyl, which has a total number of carbons between 5 and 16; an alkyl substituted with a phenyl, which has a total number of carbons between 7 and 16; a cycloalkyl optionally substituted with one or more alkyl, which has a total number of carbons between 5 and 16; and

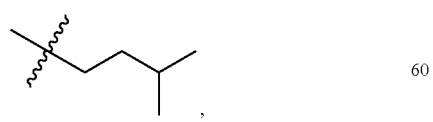

,

[2] the compound of [1], or a pharmaceutically acceptable salt thereof, wherein $R^1$ is a $C_{7-16}$ alkyl,

[3] the compound of [1] or [2], or a pharmaceutically acceptable salt thereof, wherein $R^1$ is an alkyl having the formula $—(CH_2)_n—CH_3$, wherein n is an integer selected from 6, 7, 8, 9, 10, 11, or 12,

[4] the compound of [1], or a pharmaceutically acceptable salt thereof, wherein $R^1$ is an alkyl having the formula $—(CH_2)_8—CH_3$ or

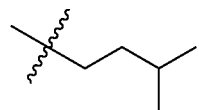

;

[5] a pharmaceutical composition comprising the compound of any one of [1]-[4], or a pharmaceutically acceptable salt thereof, and a pharmaceutically acceptable carrier;

[6] a pharmaceutical composition comprising abiraterone decanoate having the formula of:

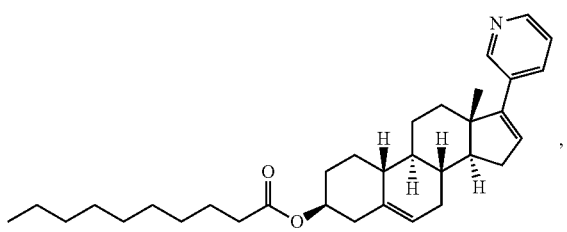

, or a pharmaceutically acceptable salt thereof, and a pharmaceutically acceptable carrier,

[7] the pharmaceutical composition of [5] or [6], formulated for intramuscular injection, intradermal injection, or subcutaneous injection,

[8] the pharmaceutical composition of any one of [5]-[7], wherein the pharmaceutically acceptable carrier comprises a pharmaceutically acceptable oil and optionally a further pharmaceutically acceptable solvent,

[9] the pharmaceutical composition of [8], wherein the pharmaceutically acceptable oil comprises a triglyceride (e.g., long and/or medium chain triglycerides), and the further pharmaceutically acceptable solvent, if present, comprises an alcohol, ester, and/or acid solvent,

[10] the pharmaceutical composition of any one of [8]-[9], wherein the pharmaceutically acceptable oil is selected from vegetable oil, castor oil, corn oil, sesame oil, cottonseed oil, peanut oil (arachis oil), poppy seed oil, tea seed oil, and soybean oil, and the further pharmaceutically acceptable solvent, if present, comprises benzyl alcohol, benzyl benzoate, or a combination thereof,

[11] the pharmaceutical composition of any one of [6]-[10], which comprises the abiraterone decanoate or pharmaceutically acceptable salt thereof in an amount sufficient to provide a therapeutically effective blood plasma concentration of abiraterone, or a blood plasma concentration of abiraterone of about 1 ng/ml or higher, for a period of at least two weeks (e.g., at least three weeks, at least four weeks, and up to six or eight weeks or more), after a single administration to a subject having one or more disorders selected from a sex hormone-dependent benign or malignant disorder, a syndrome due to androgen excess, and a syndrome to glucocorticoid excess such as hypercortisolemia,

[12] a method of treating one or more disorders selected from a sex hormone-dependent benign or malignant disorder, a syndrome due to androgen excess, and a syndrome to glucocorticoid excess such as hypercortisolemia, comprising administering to a subject in need thereof a therapeutically effective amount of the pharmaceutical composition of any one of [5]-[11],

[13] the method of [12], wherein the administering is an intramuscular injection, intradermal injection, or subcutaneous injection,

[14] the method of any one of [12]-[13], wherein the pharmaceutical composition is administered to the subject with or without food,

[15] the method of any one of [12]-[14], wherein the one or more disorders are selected from prostate cancer, breast cancer, ovarian cancer, bladder cancer, hepatocellular carcinoma, lung cancer, endometriosis, polycystic ovary syndrome, Cushing's syndrome, Cushing's disease, classical congenital adrenal hyperplasia, nonclassical congenital adrenal hyperplasia, precocious puberty, hirsutism, and combinations thereof.

[16] the method of any one of [12]-[14], wherein the one or more disorders is a sex hormone-dependent benign or malignant disorder selected from castration resistant prostate cancer and castration sensitive prostate cancer,

[17] the method of any one of [12]-[14], wherein the one or more disorders is a sex hormone-dependent benign or malignant disorder selected from metastatic castration resistant prostate cancer and metastatic castration sensitive prostate cancer,

[18] the method of any one of [12]-[17], wherein the subject is treated with a gonadotropin-releasing hormone analog and/or bilateral orchiectomy,

[19] the method of any one of [12]-[18], further comprising administering to the subject a corticosteroid,

[20] the method of any one of [12]-[19], further comprising administering to the subject prednisone, prednisolone, and/or methylprednisolone,

[21] the method of any one of [12]-[20], wherein the pharmaceutical composition is administered to the subject once a week or once in more than a week, e.g., the dosing frequency ranges from once a week to once every few months, such as from once a week to once every eight weeks, or once a week to once every three months,

[22] the method of any one of [12]-[21], wherein the administering provides (a) a blood plasma concentration of abiraterone above 1.0 ng/ml for a period of at least two weeks; (b) a single dose or steady state $C_{max}$ of abiraterone between about 10 ng/ml and about 400 ng/ml; or (c) both (a) and (b),

[23] a pharmaceutical composition, e.g., a unit dosage form, comprising a therapeutically effective amount of abiraterone decanoate having the formula of:

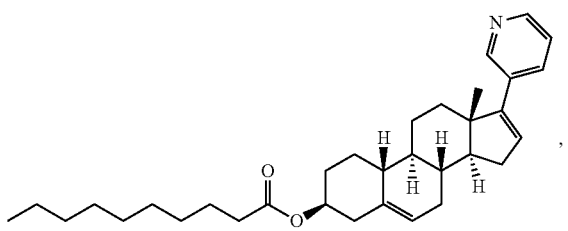

a pharmaceutically acceptable oil, and a pharmaceutically acceptable solvent, wherein the abiraterone decanoate is in its basic form, which is present at a concentration of about 25 mg/ml to about 500 mg/ml, wherein the pharmaceutical composition, e.g., unit dosage form, is formulated for intramuscular injection, intradermal injection, or subcutaneous injection, wherein the pharmaceutical composition, e.g., unit dosage form, comprises the abiraterone decanoate in an amount of about 50 mg to about 2,000 mg,

[24] the pharmaceutical composition, e.g., unit dosage form, of [23], wherein the pharmaceutically acceptable oil comprises a triglyceride, and the pharmaceutically acceptable solvent comprises an alcohol, ester, and/or acid solvent,

[25] the pharmaceutical composition, e.g., unit dosage form, of [23] or [24], wherein pharmaceutically acceptable oil comprises a vegetable oil, castor oil, corn oil, sesame oil, cottonseed oil, peanut oil, poppy seed oil, tea seed oil, or soybean oil, the pharmaceutically acceptable solvent comprises benzyl alcohol and/or benzyl benzoate, and wherein the abiraterone decanoate is present at a concentration of about 50 mg/mL to about 300 mg/mL, such as about 100 mg/mL to about 300 mg/mL,

[26] a method of treating prostate cancer, comprising administering to a subject in need thereof the pharmaceutical composition, e.g., unit dosage form, of any one of [23]-[25] via intramuscular injection, intradermal injection, or subcutaneous injection, once a month or once in more than a month, e.g., the dosing frequency ranges from once a month to once every few months, such as from once a month to once every two months, or from once a month to once every three months, etc.,

[27] the method of [26], wherein the pharmaceutical composition, e.g., unit dosage form, is administered via intramuscular injection,

[28] a method for preparing an abiraterone decanoate formulation, e.g., suitable for parenteral administration to a subject having a sex hormone-dependent benign or malignant disorder, a syndrome due to androgen excess, and/or a syndrome due to glucocorticoid excess such as hypercortisolemia, comprising:

a) mixing abiraterone decanoate, which has the formula of:

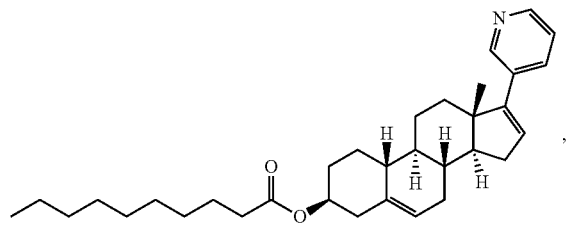

a pharmaceutically acceptable carrier to form a mixture; and optionally b) sterilizing the mixture formed in a),

[29] the method of [28], wherein the mixing comprises mixing a crystalline form of abiraterone decanoate in the pharmaceutically acceptable carrier, wherein the crystalline form is characterized by an X-Ray Powder Diffraction (XRPD) spectrum having one or more (e.g., 1, 2, 3, 4, 5, 6, 7, 8, or 9) of the following peaks: 4.6, 6.9, 8.7, 17.5, 18.3, 18.6, 19.1, 19.6, and 20.8, degrees 2 theta, ±0.2°; a Differential Scanning Calorimetry (DSC) pattern having an endothermic peak with an onset temperature at about 69.0° C.; or a combination thereof,

[30] the method of [28] or [29], wherein the pharmaceutically acceptable carrier comprises a pharmaceutically acceptable oil and a pharmaceutically acceptable solvent, wherein the pharmaceutically acceptable oil comprises a vegetable oil, castor oil, corn oil, sesame oil, cottonseed oil, peanut oil, poppy seed oil, tea seed oil, or soybean oil, the pharmaceutically acceptable solvent comprises benzyl alcohol or benzyl benzoate, and wherein the abiraterone decanoate is present at a concentration of about 50 mg/mL to about 300 mg/mL, such as about 100 mg/mL to about 300 mg/mL.

Embodiments of the present disclosure can fulfill a long felt need in the field of sex hormone-dependent disorders and oncology including the chemotherapy of prostate cancer. Embodiments of the present disclosure can also fulfill a long felt need in the field of treating syndromes due to androgen excess syndrome and/or due to glucocorticoid excess such as hypercortisolemia. Embodiments of the present disclosure can overcome major disadvantages and deficiencies of prior art formulations (including commercially-available oral dosage forms) of abiraterone acetate, by providing long-acting, sustained release depot-based parenteral formulations of abiraterone prodrugs, methods of producing the same, methods of treatment using the same, and kits for convenient administration of the formulations to subjects in need of therapy for various disorders including prostate cancer.

There has thus been outlined, rather broadly, features in order that the detailed description thereof that follows may be better understood, and in order that the present contribution to the art may be better appreciated. There are, of course, additional features that will be described further hereinafter. Indeed, it is to be understood that both the foregoing general description and the following detailed description are exemplary and explanatory and are intended to provide further explanation of the disclosure.

In this respect, before explaining at least one embodiment in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those persons skilled in the art will appreciate that the conception upon which this disclosure is based can readily be utilized as a basis for the designing of other formulations, methods, systems, kits, and compositions for carrying out the several purposes of the present disclosure. It is important, therefore, that equivalent constructions insofar as they do not depart from the spirit and scope of the present disclosure, are included in the present disclosure.

The accompanying drawings are included to provide a further understanding and are incorporated in and constitute a part of this specification, illustrate several embodiments, and together with the description serve to explain the principles.

BRIEF DESCRIPTION OF THE DRAWINGS

FIG. 1 shows the profile obtained with abiraterone acetate solution in castor oil (70 mg/ml); the profile obtained with abiraterone acetate suspension, sodium phosphate buffer, 0.1% Tween (70 mg/ml); the profile obtained with abiraterone suspension in castor oil (62.5 mg/ml) and the profile obtained with abiraterone suspension, sodium phosphate buffer, 0.1% Tween (62.5 mg/ml).

FIG. 2 shows the profile obtained with IV administration of abiraterone acetate solution (33% aq HP-beta-cyclodextrin) dosed at 10 mg/kg; the profile obtained with IM administration of abiraterone acetate solution in castor oil (66 mg/ml) dosed at 21 mg/kg; the profile obtained with IM administration of abiraterone acetate solution in castor oil with 10% benzyl alcohol (91 mg/ml) dosed at 30 mg/kg and the profile obtained with IM administration of abiraterone acetate solution in castor oil with 50% benzyl benzoate (124 mg/ml) dosed at 42 mg/kg.

FIG. 11A shows a computer modeling prediction following an IM dose of 120 mg abiraterone decanoate every two weeks and FIG. 11B shows a computer modeling prediction following an IM dose of 350 mg abiraterone decanoate every four weeks. FIG. 11C shows a computer modeling prediction following an IM dose of 1000 mg abiraterone decanoate every six weeks. FIG. 11D shows a computer modeling prediction following an IM dose of 1700 mg abiraterone decanoate every two months. The horizontal lines in FIG. 11A, FIG. 11B, FIG. 11C, and FIG. 11D represent a targeted $C_{min}$ value of abiraterone of about 8 ng/ml.

As shown in FIG. 14C, following the single dose IM injection, a long duration of CYP17A1 inhibition was achieved as evidenced by the sustained increase of progesterone level and reduction of glucocorticoid (cortisol) and sex hormone (testosterone) level. As shown in FIG. 14D, inhibition of CYP17A1 17α-hydroxylase and C17,20-lyase activities will lead to (1) increases in levels of progesterone and the mineralocorticoids; (2) reductions in levels of glucocorticoids such as cortisol; and (3) reductions in levels of sex hormones, e.g., androgens such as testosterone and dihydrotestosterone, and estrogens such as estradiol.

DETAILED DESCRIPTION

Figure 1:
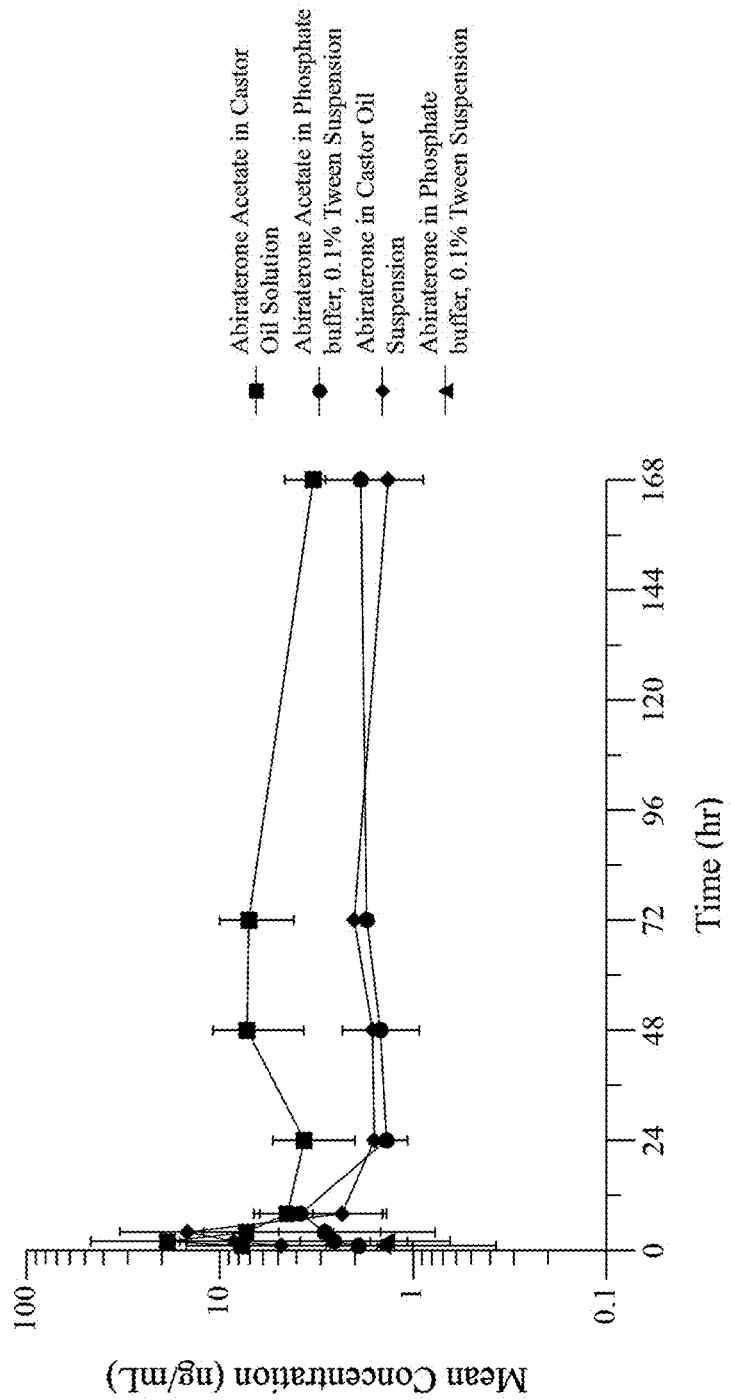
FIG. 1 shows the mean blood plasma concentrations of abiraterone (ng/ml) in rats at different times (hours) after IM administration of various abiraterone or abiraterone acetate formulations.

The present disclosure relates to compounds and compositions that deliver therapeutic blood plasma levels of the active drug abiraterone over an extended period of time to subjects. Initial experiments in the rat determined that injecting suspensions of the active drug abiraterone intramuscularly did not achieve the desired therapeutic blood plasma levels. However, as detailed herein, it was found that representative novel abiraterone prodrugs and formulations, when administered parenterally (e.g., intramuscularly), achieved desired therapeutic blood plasma levels for a prolonged period of time.

Accordingly, various embodiments of the present disclosure are directed to such novel abiraterone prodrugs and formulations, which can have various advantages over existing abiraterone formulations, such as the marketed oral abiraterone acetate formulation. Such advantages include, but are not limited to, improved bioavailability, elimination of the food effect associated with oral abiraterone acetate formulation, reduced pill burden, better patient compliance, decreased dosing frequency, sustained stable blood levels of active drug, reduced $C_{max}$, which can reduce associated side effects, etc. In some embodiments, methods of using the novel abiraterone prodrugs and formulations are also provided, for example, for treating sex hormone-dependent benign or malignant disorders (such as prostate cancer), syndromes due to androgen excess, and/or syndromes due to glucocorticoid excess such as hypercortisolemia.

Compounds of Formula I

In some embodiments, the present disclosure provides a novel abiraterone prodrug. In some embodiments, the novel abiraterone prodrug is a compound of Formula I, or a pharmaceutically acceptable salt thereof:

Formula I

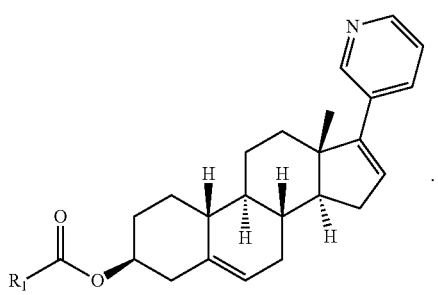

Various groups are suitable as $R^1$ in Formula I. In some embodiments, $R^1$ can be selected such that the compound of Formula I is an ester (e.g., a lipophilic ester), a carbamate, or a carbonate of abiraterone. In some embodiments, $R^1$ is $R^{10}$, O—$R^{10}$, or NHR$^{10}$, wherein $R^{10}$ is selected from: a $C_{7-30}$ alkyl; $C_{7-30}$ alkenyl; $C_{7-30}$ alkynyl; an alkyl substituted with a cycloalkyl, which typically has a total number of carbons between 5 and 16; an alkyl substituted with a phenyl, which typically has a total number of carbons between 7 and 16; a cycloalkyl optionally substituted with one or more alkyl, which typically has a total number of carbons between 5 and 16; and a branched C5 or C6 alkyl such as

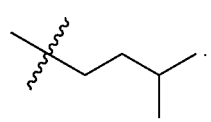

In some preferred embodiments, $R^{10}$ is a $C_{7-30}$ alkyl. As used herein, unless expressly stated to be substituted, an alkyl should be understood as unsubstituted. However, an alkyl can be either linear or branched. In some embodiments, $R^{10}$ can be a linear $C_{7-30}$ alkyl. In some embodiments, $R^{10}$ can be a branched $C_{7-30}$ alkyl. In some embodiments, $R^{10}$ is a linear $C_{7-16}$ alkyl, for example, $R^{10}$ can have a formula —(CH$_2$)$_n$—CH$_3$, wherein n is an integer between 6 and 15 (e.g., between 6 and 12, such as 6, 7, 8, 9, 10, 11, or 12). In some embodiments, $R^{10}$ can be a branched $C_{7-16}$ alkyl.

In some embodiments, $R^{10}$ can also be an alkyl substituted with a cycloalkyl. Typically, in such embodiments, $R^{10}$ has a total number of carbons between 5 and 16, i.e., the total number of carbons from the alkyl moiety and the cycloalkyl moiety are between 5 and 16. The cycloalkyl typically is unsubstituted. However, in some embodiments, the cycloalkyl can be optionally substituted, e.g., with one or two lower alkyl (e.g, a $C_{1-4}$ alkyl). In some embodiments, $R^{10}$ can be an alkyl substituted with a $C_{3-6}$ cycloalkyl, which typically has a total number of carbons between 6 and 12. In some embodiments, $R^{10}$ can be a linear alkyl substituted with a $C_{3-6}$ cycloalkyl, for example, $R^{10}$ can have a formula —(CH$_2$)$_n$-Cy, wherein n is an integer of 1-6 (e.g., 1, 2, 3, 4, 5, or 6), and Cy is a $C_{3-6}$ cycloalkyl (such as cyclopropyl, cyclobutyl, cyclopentyl, or cyclohexyl). In some embodiments, $R^{10}$ can have a formula —(CH$_2$)$_n$-Cy, wherein n is 1 or 2, and Cy is cyclopentyl or cyclohexyl. In some embodiments, $R^{10}$ can also be a branched alkyl (e.g., branched $C_{2-6}$) substituted with a $C_{3-6}$ cycloalkyl. As used herein, a branched $C_2$ alkyl should be understood as a 1,1-disubstituted ethyl group, for example, —CH(CH$_3$)-Cy.

In some embodiments, $R^{10}$ can also be an alkyl substituted with a phenyl. Typically, in such embodiments, $R^{10}$ has a total number of carbons between 7 and 16, i.e., the total number of carbons from the alkyl moiety and the phenyl moiety are between 5 and 16. In some embodiments, $R^{10}$ can be a linear alkyl substituted with a phenyl, for example, $R^{10}$ can have a formula —(CH$_2$)$_n$-Cy, wherein n is an integer of 1-6 (e.g., 1, 2, 3, 4, 5, or 6), and Cy is a phenyl. In some embodiments, $R^{10}$ can have a formula —(CH$_2$)$_n$-Cy, wherein n is 1 or 2, and Cy is phenyl. In some embodiments, $R^{10}$ can also be a branched alkyl (e.g., branched $C_{2-6}$) substituted with a phenyl. The phenyl typically is unsubstituted. However, in some embodiments, the phenyl can be optionally substituted, e.g., with one or two lower alkyl (e.g, a $C_{1-4}$ alkyl).

In some embodiments, $R^{10}$ can be a cycloalkyl optionally substituted with one or more alkyl. In such embodiments, $R^{10}$ typically has a total number of carbons between 5 and 16, i.e., the total number of carbons of the cycloalkyl and its optional substituents are between 5 and 16. In some embodiments, $R^{10}$ can be a $C_{3-6}$ cycloalkyl, either unsubstituted or substituted with a $C_{1-4}$ alkyl. In some specific embodiments, $R^{10}$ can be or

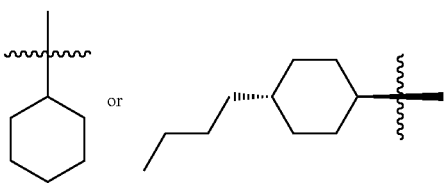

In some embodiments, $R^{10}$ can be a branched C5 or C6 alkyl. In some embodiments, $R^{10}$ can be

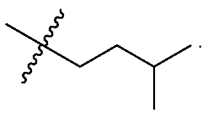 [SMILES: *CCC(C)C]

Other branched C5 or C6 alkyls are also suitable.

In some embodiments, $R^{10}$ can be an unsaturated aliphatic group such as a $C_{7\text{-}30}$ alkenyl or a $C_{7\text{-}30}$ alkynyl.

In some preferred embodiments, the compound of Formula I is an ester of abiraterone, e.g., $R^1$ is $R^{10}$, wherein $R^{10}$ is defined herein. In some embodiments, $R^1$ in Formula I can be a $C_{7\text{-}16}$ alkyl, e.g., an alkyl having a formula of —$(CH_2)_n$—$CH_3$, wherein n is an integer between 6 and 12 (e.g., 6, 7, 8, 9, 10, 11, or 12). In some embodiments, $R^1$ in Formula I can be represented by the formula —$(CH_2)_n$-Cy, wherein n is an integer of 1-6, and Cy is a $C_{3\text{-}6}$ cycloalkyl or phenyl, for example, in more specific embodiments, n can be 1 or 2, and Cy is cyclopentyl, cyclohexyl, or phenyl. In some specific embodiments, $R^1$ in Formula I can be

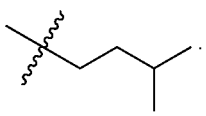

In some specific embodiments, $R^1$ in Formula I can be or

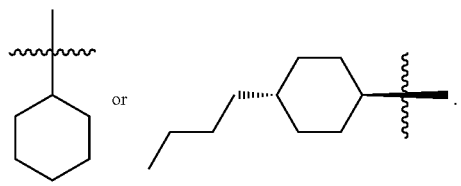

Other suitable groups for $R^1$ include any of the $R^{10}$ defined herein.

In some embodiments, $R^1$ in Formula I can also be O—$R^{10}$ or $NHR^{10}$, wherein $R^{10}$ is defined herein.

Typically, compounds of Formula I can be present in a formulation in the basic form, for example, in a non-aqueous formulation. However, in some embodiments, pharmaceutically acceptable salts of compounds of Formula I are also useful. Unless specifically referred to as in its salt form or otherwise contradictory from context, the compound of Formula I can be in its basic form in the abiraterone prodrug formulations described herein.

Compounds of Formula I can be readily synthesized by those skilled in the art in view of the present disclosure. Exemplary synthesis of representative compounds are described in the Examples section. For example, typically, esters of Formula I can be prepared by reacting abiraterone with a corresponding carboxylic acid, or an activated form thereof, such as the corresponding acyl chloride, anhydride, etc. Exemplary reaction conditions using an activated form such as acyl chloride are shown in the Examples section.

Abiraterone Prodrug Formulations

Abiraterone prodrugs herein, including compounds of Formula I, are useful for delivering abiraterone to a subject in need thereof, for example, to a subject having a sex hormone-dependent benign or malignant disorder, a syndrome due to androgen excess, and/or a syndrome due to glucocorticoid excess such as hypercortisolemia herein. Typically, the abiraterone prodrugs can be formulated as a parenteral formulation, such as an intramuscular, intradermal, or subcutaneous formulation, and can in some embodiments be formulated to deliver a therapeutically effective plasma concentration of abiraterone over an extended period of time, e.g., for at least 1 week, at least 2 weeks, at least 3 weeks, at least 4 weeks, and up to six or eight weeks or more, etc.

Various abiraterone prodrugs, such as abiraterone esters, carbamates, or carbonates are suitable for compositions and methods of the present disclosure. In some embodiments, the present disclosure provides a pharmaceutical composition (alternatively sometimes referred to as abiraterone prodrug formulation herein) comprising a compound of Formula I (e.g., any one or more as defined herein), or a pharmaceutically acceptable salt thereof. In some embodiments, the pharmaceutical composition can be formulated for parenteral administration, such as intramuscular injection, intradermal injection, or subcutaneous injection. The pharmaceutical composition typically includes a pharmaceutically acceptable carrier. Suitable carriers include those known in the art, for example, those described in "Remington: The Science and Practice of Pharmacy" (formerly "Remington's Pharmaceutical Sciences," University of the Sciences in Philadelphia, Lippincott, Williams & Wilkins, Philadelphia, Pa. (2005)) and the U.S. Food and Drug Administration's Center for Drug Evaluation and Research's database of inactive ingredients present in FDA-approved drugs. In some embodiments, the pharmaceutically acceptable carrier can be a carrier that is approved for use by the FDA for an intramuscular, intradermal, or subcutaneous drug product, e.g., those listed in the FDA's database of inactive ingredients. In some embodiments, the pharmaceutically acceptable carrier can be any suitable nonaqueous vehicle suitable for injection, such as those described in U.S. Pharmacopeia. In some embodiments, the pharmaceutically acceptable carrier can be a pharmaceutically acceptable oil, e.g., a vegetable oil, castor oil, corn oil, sesame oil, cottonseed oil, peanut oil, poppy seed oil, tea seed oil, or soybean oil. In some embodiments, the pharmaceutically acceptable oil can be oils (e.g., described herein) suitable for use as vehicles for injection, e.g., meeting the criteria as described in the corresponding U.S. Pharmacopeia monograph. In some embodiments, the pharmaceutically acceptable oil can be an oil of vegetable origin suitable for use as vehicles for injection. In some embodiments, the pharmaceutically acceptable oil can be a synthetic oil suitable for use as vehicles for injection, such as a synthetic mono- or diglycerides of fatty acids, e.g., those that are liquid and remain clear when cooled to 10° C. and have an Iodine Value of not more than 140. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. In some embodiments, two or more different pharmaceutically acceptable oil can be used. In some embodiments, the pharmaceutical composition is a non-aqueous solution or suspension. In some embodiments, the pharmaceutical composition further comprises a pharmaceutically acceptable solvent, such as benzyl alcohol. In some embodiments, the compound of Formula I or pharmaceutically acceptable salt thereof can be present in the pharmaceutical composition at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any range between the recited values).

In some embodiments, the present disclosure also provides a pharmaceutical composition (alternatively sometimes referred to as abiraterone prodrug formulation herein) comprising a compound of Formula II, or a pharmaceutically acceptable salt thereof.

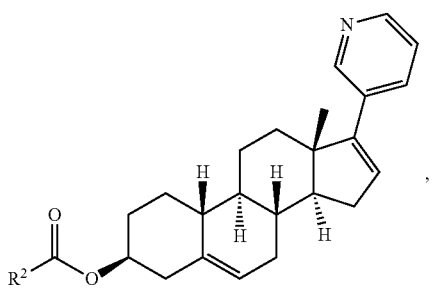

Formula II wherein $R^2$ is defined herein. In some embodiments, the pharmaceutical composition can be formulated for intramuscular injection, intradermal injection, or subcutaneous injection. In some embodiments, the compound of Formula II or pharmaceutically acceptable salt thereof can be present in the pharmaceutical composition at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any range between the recited values). In some embodiments, the pharmaceutical composition is a non-aqueous solution or suspension. In some embodiments, the compound of Formula II or pharmaceutically acceptable salt thereof is dissolved or suspended in a pharmaceutically acceptable oil (e.g., described herein), such as a vegetable oil, castor oil, corn oil, sesame oil, cottonseed oil, peanut oil, poppy seed oil, tea seed oil, or soybean oil. In some embodiments, the pharmaceutical composition further comprises a pharmaceutically acceptable solvent, such as benzyl alcohol.

Various groups are suitable as $R^2$ in Formula II. In some embodiments, $R^2$ can be selected such that the compound of Formula II is an ester, a carbamate, or a carbonate of abiraterone. In some embodiments, $R^2$ is $R^{20}$, O—$R^{20}$, or NH$R^{20}$, and $R^{20}$ is selected from: a $C_{1-30}$ alkyl; a $C_{2-30}$ alkenyl; a $C_{2-30}$ alkynyl; an alkyl substituted with a cycloalkyl, which typically has a total number of carbons between 4 and 30; an alkyl substituted with a phenyl, which typically has a total number of carbons between 7 and 30; and a cycloalkyl optionally substituted with one or more alkyl, which typically has a total number of carbons between 3 and 30.

In some preferred embodiments, $R^{20}$ is a $C_{1-16}$ alkyl. In some embodiments, $R^{20}$ can be a linear $C_{1-16}$ alkyl. In some embodiments, $R^{20}$ can be a branched $C_{3-16}$ alkyl. In some embodiments, $R^{20}$ can be a branched C5 or C6 alkyl. In some embodiments, $R^{20}$ can be

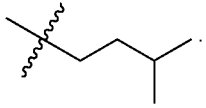 [SMILES: *CCC(C)C]

In some embodiments, $R^{20}$ can have a formula —$(CH_2)_n$—$CH_3$, wherein n is an integer between 0 and 12 (e.g., between 6 and 12, such as 6, 7, 8, 9, 10, 11, or 12).

In some embodiments, $R^{20}$ can also be an alkyl substituted with a cycloalkyl. Typically, in such embodiments, $R^{20}$ has a total number of carbons between 4 and 30, such as between 5 and 16 (i.e., the total number of carbons from the alkyl moiety and the cycloalkyl moiety are between 5 and 16). The cycloalkyl typically is unsubstituted. However, in some embodiments, the cycloalkyl can be optionally substituted, e.g., with one or two lower alkyl (e.g, a $C_{1-4}$ alkyl). In some embodiments, $R^{20}$ can be an alkyl substituted with a $C_{3-6}$ cycloalkyl, which typically has a total number of carbons between 6 and 12. In some embodiments, $R^{20}$ can be a linear alkyl substituted with a $C_{3-6}$ cycloalkyl, for example, $R^{20}$ can have a formula —$(CH_2)_n$-Cy, wherein n is an integer of 1-6 (e.g., 1, 2, 3, 4, 5, or 6), and Cy is a $C_{3-6}$ cycloalkyl (such as cyclopropyl, cyclobutyl, cyclopentyl, or cyclohexyl). In some embodiments, $R^{20}$ can have a formula —$(CH_2)_n$-Cy, wherein n is 1 or 2, and Cy is cyclopentyl or cyclohexyl. In some embodiments, $R^{20}$ can also be a branched alkyl (e.g., branched $C_{2-6}$) substituted with a $C_{3-6}$ cycloalkyl.

In some embodiments, $R^{20}$ can also be an alkyl substituted with a phenyl. Typically, in such embodiments, $R^{20}$ has a total number of carbons between 7 and 30, e.g., between 7 and 16 (i.e., the total number of carbons from the alkyl moiety and the phenyl moiety are between 7 and 16). In some embodiments, $R^{20}$ can be a linear alkyl substituted with a phenyl, for example, $R^{20}$ can have a formula —$(CH_2)_n$-Cy, wherein n is an integer of 1-6 (e.g., 1, 2, 3, 4, 5, or 6), and Cy is a phenyl. In some embodiments, $R^{20}$ can have a formula —$(CH_2)_n$-Cy, wherein n is 1 or 2, and Cy is phenyl. In some embodiments, $R^{20}$ can also be a branched alkyl (e.g., branched $C_{2-6}$) substituted with a phenyl. The phenyl typically is unsubstituted. However, in some embodiments, the phenyl can be optionally substituted, e.g., with one or two lower alkyl (e.g, a $C_{1-4}$ alkyl).

In some embodiments, $R^{20}$ can be a cycloalkyl optionally substituted with one or more alkyl. In such embodiments, $R^{20}$ typically has a total number of carbons between 3 and 30, e.g., 5 and 16 (i.e., the total number of carbons of the cycloalkyl and its optional substituents are between 5 and 16). In some embodiments, $R^{20}$ can be a $C_{3-6}$ cycloalkyl, either unsubstituted or substituted with a $C_{1-4}$ alkyl. In some specific embodiments, $R^{20}$ can be

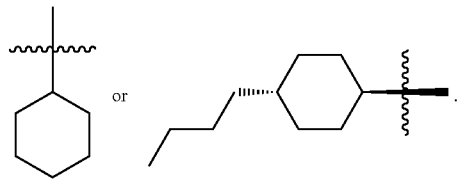

In some embodiments, $R^{20}$ can be an unsaturated aliphatic group such as a $C_{2-30}$ alkenyl or a $C_{2-30}$ alkynyl.

In some preferred embodiments, the compound of Formula II is an abiraterone ester, e.g., $R^2$ is $R^{20}$, wherein $R^{20}$ is defined herein. In some embodiments, $R^2$ in Formula II can be a $C_{1-16}$ alkyl, e.g., an alkyl having a formula of —$(CH_2)_n$—$CH_3$, wherein n is an integer between 0 and 12. In some embodiments, $R^2$ in Formula II can be represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl. In some specific embodiments, $R^2$ in Formula II can be

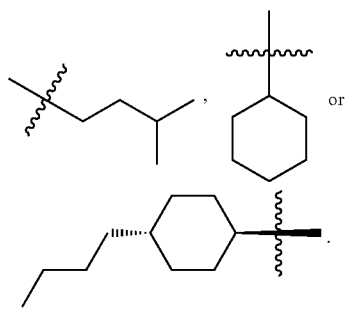

Other suitable groups for $R^2$ include any of the $R^{20}$ defined herein. In some embodiments, the abiraterone ester can be an acetate, a propionate, a butanoate, a (vaterate) pentanoate, an isocaproate, a buciclate, a cyclohexanecarboxylate, a phenyl propionate, caproate (hexanoate), a enanthate (heptanoate), a cypionate, an octanoate, a noncanoate, a decanoate, an undecanoate, a dodecanoate, a tridecanoate, a tetradecanoate, a pentadecanoates, or a hexadecanoate of abiraterone. In some embodiments, the abiraterone ester can be abiraterone acetate, abiraterone propionate, and abiraterone decanoate. In some specific embodiments, the abiraterone ester can be abiraterone pentanoate, abiraterone hexanoate, abiraterone heptanoate, abiraterone decanoate, abiraterone isocaproate, or abiraterone cypionate.

In some embodiments, $R^2$ in Formula II can also be O—$R^{20}$ or NH$R^{20}$, wherein $R^{20}$ is defined herein.

Typically, compounds of Formula II can be present in a formulation in the basic form, for example, in a non-aqueous formulation. However, in some embodiments, pharmaceutically acceptable salts of compounds of Formula II are also useful. Unless specifically referred to as in its salt form or otherwise contradictory from context, the compound of Formula II can be in its basic form in the abiraterone prodrug formulations described herein.

Compounds of Formula II can be readily synthesized by those skilled in the art in view of the present disclosure. Exemplary synthesis of representative compounds are described in the Examples section. For example, typically, esters of Formula II can be prepared by reacting abiraterone with a corresponding carboxylic acid, or an activated form thereof, such as the corresponding acyl chloride, anhydride, etc. Exemplary reaction conditions using an activated form such as acyl chloride are shown in the Examples section.

Typically, the abiraterone prodrugs of the present disclosure are formulated as a non-aqueous solution or suspension. In some embodiments, the non-aqueous solution or suspension provides higher levels of abiraterone in the plasma for a longer duration, when compared to an aqueous solution or suspension. For example, as detailed herein, IM injections of an aqueous suspension and a vegetable oil solution of the abiraterone acetate prodrug were evaluated in rats. Surprisingly, it was determined that the vegetable oil solution (but not the aqueous suspension) of abiraterone acetate prodrug gave the highest blood plasma levels and also the longest duration of exposure of active drug abiraterone (see FIG. 1). Accordingly, in some embodiments, the abiraterone prodrug formulations herein can include an abiraterone prodrug of the present disclosure (e.g., compound of Formula I or II) dissolved or dispersed in a pharmaceutically acceptable carrier. In some embodiments, the pharmaceutically acceptable carrier can be any suitable nonaqueous vehicle suitable for injection, such as those described in U.S. Pharmacopeia. In some embodiments, the pharmaceutically acceptable carrier can be a pharmaceutically acceptable oil, e.g., a vegetable oil, castor oil, corn oil, sesame oil, cottonseed oil, peanut oil, poppy seed oil, tea seed oil, or soybean oil. In some embodiments, the pharmaceutically acceptable oil can be oils (e.g., described herein), suitable for use as vehicles for injection, e.g., meeting the criteria as described in the corresponding U.S. Pharmacopeia monograph. In some embodiments, the pharmaceutically acceptable oil can be an oil of vegetable origin suitable for use as vehicles for injection. In some embodiments, the pharmaceutically acceptable oil can be a synthetic oil suitable for use as vehicles for injection, such as synthetic mono- or diglycerides of fatty acids, e.g., those that are liquid and remain clear when cooled to 10° C. and have an Iodine Value of not more than 140. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. In some embodiments, the pharmaceutically acceptable oil can be any of those that are approved for use by the FDA for an intramuscular, intradermal, or subcutaneous drug product, e.g., those listed in the FDA's database of inactive ingredients. In some specific embodiments, the pharmaceutically acceptable oil is castor oil or corn oil. In some embodiments, two or more different pharmaceutically acceptable oil can be used.

Other ingredients can also be optionally included in the abiraterone prodrug formulations herein. In some embodiments, the abiraterone prodrug formulation can further comprise a pharmaceutically acceptable solvent, such as benzyl alcohol, benzyl benzoate, ethanol, glycerol, polyethylene glycol, polysorbate 80, acetic acid, and ethyl acetate. It was determined that the additives/co-solvents benzyl alcohol and benzyl benzoate had the advantage of increasing the solubility of the prodrugs as well as reducing the viscosity and/or glide force of the solution, see e.g., FIGS. 13A-13E and Tables 2A-2D, which provided a more concentrated solution that was easier to inject through an acceptable gauge needle for IM injection (e.g., 20-27 gauge such as 22-25 gauge). The co-solvent can be selected based on its ability to reduce the viscosity of the vehicle to allow injection through suitable injection needles or cannula. Benzyl alcohol as an additive in IM or subcutaneous injections also has the advantage that it can act as a local anesthetic at the injection site (Wilson et al. Ann. Emer. Med. 33(5), 495, 1999). In some embodiments, the abiraterone prodrug formulation further comprises benzyl alcohol. In some embodiments, the cosolvent, if present, can be included at a level (e.g., about 0-50% of the solvent, such as about 10%) such that it does not cause irritation (or only minimal or tolerable irritation) at the injection site.

In some embodiments, the abiraterone prodrug formulation can comprise benzyl benzoate as a cosolvent, for example, about 0-50% of the solvent, typically 0-35% or 0-30%, or about 20%. In some embodiments, the abiraterone prodrug formulation can comprise a combination of benzyl alcohol and benzyl benzoate as cosolvents. In some embodiments, the benzyl alcohol can be present in an amount of about 0-20% (e.g., 0-15% or 0-10%, such as about 10%) of the solvent, and benzyl benzoate can be present in an amount of about 0-50% (e.g., 0-35% or 0-30%, such as about 20%) of the solvent, wherein the balance of the solvent can be any one or more of the pharmaceutically acceptable oil described herein, such as corn oil, castor oil, sesame oil, peanut oil, cottonseed oil, and/or Miglyol 812, etc. As discussed in more detail in the Examples section, the inclusion of benzyl benzoate in various oil vehicles was found to be advantageous in various aspects. See e.g., FIGS. 13A-13E and Tables 2A-2D. For example, the combination of benzyl alcohol and benzyl benzoate were shown to achieve a lower viscosity and glide force, when compared with using just benzyl alcohol or benzyl benzoate. Further, it was unexpectedly found that a representative abiraterone prodrug (abiraterone decanoate) formulation comprising an oil (corn oil, 70%) and benzyl alcohol (10%) and benzyl benzoate (20%) achieved a much higher abiraterone plasma exposure in monkeys when compared with a formulation comprising the same oil vehicle without benzyl benzoate, i.e., corn oil, at 90%, and benzyl alcohol at 10%, which has substantially the same concentration of abiraterone decanoate, and dosed at the same amount.

While the oil vehicles described herein are typically used for the abiraterone prodrugs of the present disclosure, it is also contemplated that such oil vehicles can be used for formulating other active ingredients. In some embodiments, the present disclosure also provides an oil vehicle comprising benzyl alcohol in an amount of about 0-20% (e.g., 0-15% or 0-10%, such as about 10%) of the oil vehicle, and benzyl benzoate in an amount of about 0-50% (e.g., 0-35% or 0-30%, such as about 20%) of the oil vehicle, wherein the balance of the oil vehicle can be any one or more of the pharmaceutically acceptable oil described herein, such as corn oil, castor oil, sesame oil, peanut oil, cottonseed oil, and/or Miglyol 812, etc.

The solubility of the abiraterone esters can be affected upon adding a co-solvent to the vegetable oil vehicle. In some embodiments, the abiraterone ester is completely dissolved in the composition, and in other embodiments the abiraterone ester is partly dispersed in the composition. In one embodiment, the abiraterone esters are fully dissolved in the vehicle.

The abiraterone prodrug formulations can also contain pharmaceutically acceptable preservatives, polymers, antioxidants, antimicrobials, chelating agents, and other excipients such as citric acid, dextrose, ascorbic acid, benzalkonium chloride, benzoic acid, sodium betadex sulfobutyl ether, calcium chloride, sodium carbomethoxycellulose, chlorobutanol, creatine, croscarmellose, dibasic potassium phosphate, sodium docusate, sodium edetate, glycerin, sodium hyaluronate, hydroxypropyl betadex, lactic acid, lactose, lecithin, maleic acid, mannitol, meglumine, methylcellulose, methylparaben, microcrystalline cellulose, miripitium chloride, monothioglycerol, phenol, poloxamer 188, polyglactin, polysorbate 20, polysorbate 40, polysorbate 80, propylparaben, sodium acetate, sodium benzoate, sodium citrate, sorbitan monolaurate, sorbitol, sucrose, tartaric acid, trisodium citrate, tromantadine, tromethamine, and urea.

The abiraterone prodrug formulations can be sterilized by methods known by persons skilled in the art (for example, gamma irradiation, micron filtration, and autoclaving).

Long-Acting Release of Abiraterone

The abiraterone prodrugs and abiraterone prodrug formulations (e.g., those containing compounds of Formula I or II as described herein) of the present disclosure are typically formulated to provide a long-acting release of abiraterone to a subject in need thereof, such as those having a sex hormone-dependent benign or malignant disorder, a syndrome due to androgen excess, and/or a syndrome due to glucocorticoid excess such as hypercortisolemia, preferably as a parenteral formulation such as intramuscular, intradermal, or subcutaneous formulation. In some embodiments, the abiraterone prodrugs and abiraterone prodrug formulations (e.g., those containing compounds of Formula I or II as described herein) of the present disclosure can be formulated to deliver therapeutic blood plasma levels of abiraterone over an extended period of time (e.g., at least 1 week, e.g., at least two weeks, at least 3 weeks, at least 4 weeks, and up to six or eight weeks or more, etc.) to subjects having a hormone-dependent benign or malignant disorder, a syndrome due to androgen excess, and/or a syndrome due to glucocorticoid excess such as hypercortisolemia, following a single administration. In some embodiments, the therapeutic blood plasma concentration of abiraterone can be a concentration of at least 1 ng/ml, e.g., at least 2 ng/ml, at least 4 ng/ml, at least 8 ng/ml. In some embodiments, the therapeutic blood plasma concentration of abiraterone can also be about 0.5 ng/ml or higher.

As shown herein, abiraterone acetate vegetable oil IM injections were evaluated in dogs. Abiraterone acetate solutions in castor oil and the co-solvents benzyl alcohol and benzyl benzoate were prepared at various strengths (66-124 mg/ml) and injected intramuscularly into dogs, and the parent abiraterone drug blood plasma levels were measured over three weeks (see FIG. 2). The data from the dog study indicate that abiraterone acetate given as a solution in castor oil (with or without benzyl alcohol) produced measurable blood levels out to 504 hours. The absolute bioavailabilities for these formulations were found to range between 61.7 and 86.2%. This represents the first showing that it is possible to deliver abiraterone to a subject for a prolonged period of time with a single injection, which therefore allows a less frequent dosing, such as once a week or once in more than a week, e.g., the dosing frequency ranges from once a week to once every few months, such as from once a week to once every eight weeks or from once a week to once every three months.

Without wishing to be bound by theories, it is believed that the duration of action of the prodrug is dependent on the selection of the prodrug (e.g., the ester moiety) and the selection of the oil vehicle since it is controlled by both the release rate of the prodrug from the oil vehicle into the aqueous tissue and the bioconversion rate of the ester prodrug to the parent drug abiraterone. Unlike the case where abiraterone acetate is dosed orally and the bioconversion occurs prior to the drug being absorbed (and thus the prodrug is not observed in blood plasma), when abiraterone prodrug is dosed parenterally in dogs (either IV or IM) the prodrug is observed in blood plasma (see e.g., FIGS. 3-10) where it is converted into parent drug abiraterone. Therefore, an aspect of this disclosure is the selection of the ester prodrug and the vegetable oil/co-solvent vehicle so as to allow adequate solubility of the ester prodrug in the vehicle to allow injection, controlled release of the ester prodrug from the oil depot (dependent on the partition coefficient of the drug between oil and aqueous phases), and then bioconversion of the ester prodrug to the abiraterone parent drug. A selection of abiraterone pro-drugs were prepared (acetate, propionate, butanoate, pentanoate, hexanoate, heptanoate, isocaproate, cypionate, and decanoate) and their solubilities in several vegetable oils and co-solvents determined (see Table 2).

Unit Dosage Forms

In some embodiments, the abiraterone prodrugs and abiraterone prodrug formulations (e.g., those containing compounds of Formula I or II as described herein) of the present disclosure can be formulated as a unit dosage form. In some embodiments, the unit dosage form can include a sufficient amount of the respective prodrug such that after a single administration (e.g., intramuscular injection) to a subject, e.g., a subject having a sex hormone-dependent benign or malignant disorder (e.g., metastatic castration resistant prostate cancer or metastatic castration sensitive prostate cancer), a syndrome due to androgen excess, and/or a syndrome due to glucocorticoid excess such as hypercortisolemia, the unit dosage form provides a therapeutically effective blood plasma concentration of abiraterone in the subject for a period of at least two weeks, such as at least 3 weeks, at least 4 weeks, at least 5 weeks, and up to six or eight weeks or more, etc. In some embodiments, the therapeutic blood plasma concentration of abiraterone can be a concentration of at least 1 ng/ml, e.g., at least 2 ng/ml, at least 4 ng/ml, at least 8 ng/ml. In some embodiments, the therapeutic blood plasma concentration of abiraterone can also be about 0.5 ng/ml or higher. In some embodiments, the unit dosage form is a parenteral formulation such as intramuscular, intradermal, or subcutaneous formulation. In some embodiments, the unit dosage form is a non-aqueous solution or suspension. In some embodiments, the unit dosage form comprises the abiraterone prodrug (e.g., compound of Formula I or II) dissolved or suspended in a pharmaceutically acceptable oil, e.g., a vegetable oil such as castor oil, corn oil, sesame oil, cottonseed oil, peanut oil, poppy seed oil, tea seed oil, or soybean oil. In some embodiments, two or more different pharmaceutically acceptable oil can be used in the unit dosage forms. In some embodiments, the unit dosage form can further comprise a pharmaceutically acceptable solvent, e.g., an alcohol, an ester, and/or an acid, such as benzyl alcohol, benzyl benzoate, or a combination thereof. Other suitable ingredients for the unit dosage forms include those described herein.

The abiraterone prodrug (e.g., compound of Formula I or II) is typically present in the unit dosage form at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any range between the recited values). The amount of abiraterone prodrug in the unit dosage forms can vary, depending on various factors such as the clearance rate of the respective abiraterone prodrug, the intended dosing frequency and the desired plasma levels, etc. Typically, the amount of the abiraterone prodrug can be in the range of about 50 mg to about 2000 mg, which if expressed as equivalent of abiraterone, can typically range from about 25 mg to about 1750 mg. In some embodiments, to achieve a less frequent dosing frequency, such as a once a month dosing frequency, the prodrug can be included in the unit dosage form at a concentration as high as safely tolerable to a subject user. Typically, the unit dosage form is formulated to have a viscosity suitable for parenteral injection, such as suitable for intramuscular, intradermal, or subcutaneous injection.

In some embodiments, the unit dosage form can be formulated to achieve certain pharmacokinetic (PK) profiles, e.g., a PK profile with a substantially flat curve after an initial rising period. Typically, after the unit dosage form is administered to a subject, during the initial few hours and up to a few days (e.g., 5 days or a week) post administration, the plasma concentration of abiraterone in the subject can be increased, which is then gradually plateaued, see e.g., FIGS. 2-4. In some embodiments, after this initial rising period, the plasma concentration of abiraterone in the subject can be plateaued and can be substantially constant for an extended period of time, for example, for at least a few days (e.g., 2, 3, 4, 5, or 6 days), or for at least 1 week, at least 2 weeks, etc.

In some embodiments, the unit dosage form is suitable for once a month (or once in more than a month) dosing, and upon a single administration (e.g., intramuscularly) to a subject in need thereof, the unit dosage form achieves a PK profile characterized by one or more of the following: (a) the unit dosage form provides a therapeutically effective blood plasma concentration of abiraterone in the subject for at least 4 weeks; (b) a single dose $C_{max}$ of abiraterone of between about 10 ng/ml and about 400 ng/ml (e.g., between about 50 ng/ml and about 100 ng/ml, or between about 15 ng/ml and about 160 ng/ml); (c) no food effect; (d) a single dose $C_{max}$ of abiraterone reduced by at least 30% compared to the $C_{max}$ of abiraterone observed at steady state for a once daily oral dose of Zytiga® at 1000 mg without food; (e) a single dose $C_{min}$ of abiraterone at day 28 post administration between about 1 ng/ml and about 8 ng/ml, or above about 8 ng/ml; (f) the blood plasma concentration of abiraterone remains substantially constant, e.g., for at least 1 week, e.g., between 1 week and 3 weeks post administration. In some embodiments, substantially constant for a period of time can mean that the highest concentration observed for any day (i.e., 24 hours) during that time period is no greater than 4 fold, for example, no greater than 2 fold, of the lowest concentration observed for the same day. No food effect should be generally understood as that no significant differences in PK are observed when the unit dosage form is administered to subjects with food or without food, for example, in some embodiments, no food effect can mean that the $C_{max}$ and AUC of abiraterone are substantially the same (e.g., between 80% to 125%) between subjects dosed at a fed state or fasted state. A single dose $C_{max}$ as used herein should be understood as the $C_{max}$ achieved following a single administration to a treatment naïve subject (generally refers to a subject who has not received any abiraterone medication within at least 3 days, such as at least 1 week, prior to the administration and with no observable plasma abiraterone prior to the administration). A single dose $C_{min}$ used herein refers to the minimum concentration observed for a given day following a single administration to a treatment naïve subject, e.g., at day 28 post administration.

In some embodiments, the unit dosage form is suitable for once a month (or once in more than a month) dosing, and upon administration (e.g., intramuscularly) of the unit dosage form once in a month to a subject in need thereof, the unit dosage form achieves (a) a steady state $C_{max}$ of abiraterone of between about 10 ng/ml and about 400 ng/ml (e.g., between about 50 ng/ml and about 100 ng/ml, or between about 15 ng/ml and about 160 ng/ml); (b) no food effect; (c) a steady state $C_{max}$ of abiraterone reduced by at least 30% compared to the $C_{max}$ of abiraterone observed at steady state for a once daily oral dose of Zytiga® at 1000 mg without food; (d) a steady state $C_{min}$ of abiraterone between about 1 ng/ml and about 8 ng/ml, or above about 8 ng/ml; and (g) the blood plasma concentration of abiraterone remains substantially constant, e.g., for at least 1 week, e.g., between 1 week and 3 weeks post each administration. A steady state $C_{max}$ or $C_{min}$ as used herein should be understood as the $C_{max}$ or $C_{min}$ observed after a steady state is reached, typically following several administrations to a subject.

In some embodiments, the unit dosage form can be packaged in a container such as a vial or ampule. In some embodiments, the unit dosage form can be included in a pre-filled syringe or in a kit with a syringe, such as a disposable syringe. Other packaging and/or containers are also useful, which are known to those skilled in the art. In some embodiments, a kit comprising multiple unit dosage forms described herein is also provided. In some embodiments, the kit can further comprise a syringe. While in some embodiments, it is advantageous to prepare the abiraterone prodrug formulations in unit dosage forms, in some embodiments, the present disclosure also provides abiraterone prodrug formulations that allow multiple single uses, or abiraterone prodrug formulations that can be subdivided into multiple unit dosage forms.

Exemplary Specific Formulations

In some embodiments, the present disclosure also provides some specific abiraterone prodrug formulations, which can in some embodiments be in a unit dosage form or a multiple unit dosage form. For example, the tables below (Table A and B) show some representative abiraterone ester prodrug formulation in an oil vehicle. All numeric values in the tables should be understood as preceded by the term "about." The concentration of abiraterone prodrug refers to the amount of abiraterone prodrug in mg per ml of the final formulation, which can be a solution or suspension. The amount of oil (the primary solvent) and co-solvent in the tables is expressed as volume percentage of solvent, which includes both the oil and co-solvent. Suitable oil include any of the pharmaceutically acceptable oil as described herein. Suitable co-solvents also include any of those described herein, e.g., an alcohol, an ester, and/or an acid, such as benzyl alcohol, benzyl benzoate, or a combination thereof, see e.g., Table B. One example of suitable co-solvents is benzyl alcohol. One example of suitable co-solvents is a combination of benzyl alcohol and benzyl benzoate. In some embodiments, no co-solvent is included in the formulation. In some embodiments, the co-solvent does not include benzyl benzoate. Other optionally ingredients are described herein.

TABLE A

Exemplary Formulations

| Ingredients | Amount/Concentration | | |
|---|---|---|---|
| | Typical | Exemplary range | More Exemplary Range |
| Abiraterone prodrug (e.g., abiraterone acetate, abiraterone decanoate, abiraterone pentanoate, abiraterone hexanoate, abiraterone heptanoate, abiraterone isocaproate, or abiraterone cypionate) | 25 mg/ml to 500 mg/ml | 50 mg/ml to 300 mg/ml; 100 mg/ml to 300 mg/ml | 75 mg/ml to 300 mg/ml |
| Oil (e.g., castor oil, corn oil) | 50% to 100% of solvent | 70% to 100% of solvent | 80% to 100% of solvent, such as 90% |
| Co-solvent (e.g., benzyl alcohol, benzyl benzoate, or combination thereof) | 0% to 50% of solvent | 0% to 40% or 0% to 30% of solvent | 0% to 30% or 0% to 20% of solvent, such as 10%, or 30% |
| Other optional ingredients | | | |

As shown in FIGS. 13A-13E and the Examples section, benzyl alcohol and/or benzyl benzoate can enhance solubilities of abiraterone prodrugs of the present disclosure in oil vehicles, such as corn oil, and can lower viscosities and glide force of various oil vehicles, including corn oil, sesame oil, peanut oil, cottonseed oil, and Miglyol 812 (a mixture of medium chain triglycerides, mainly caprylic/capric triglycerides). In some embodiments, the present disclosure provides an abiraterone prodrug formulation comprising abiraterone prodrug and a pharmaceutically acceptable carrier, wherein the pharmaceutically acceptable carrier comprises a pharmaceutically acceptable oil (e.g., described herein), benzyl alcohol, and benzyl benzoate. In some embodiments, the abiraterone prodrug can be abiraterone decanoate. In some embodiments, the abiraterone prodrug can be abiraterone isocaproate. The pharmaceutically acceptable oil typically comprises a triglyceride derived from fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable oil can be selected from vegetable oil, castor oil, corn oil, sesame oil, cottonseed oil, peanut oil (arachis oil), poppy seed oil, tea seed oil, and soybean oil. In some embodiments, the present disclosure provides certain exemplary formulations shown in Table B.

TABLE B

Further Exemplary Formulations

| Ingredients | Amount/Concentration | | |
|---|---|---|---|
| | Typical | Exemplary range | More Exemplary Range |
| Abiraterone prodrug (e.g., abiraterone decanoate or abiraterone isocaproate) | 25 mg/ml to 500 mg/ml | 50 mg/ml to 300 mg/ml; 100 mg/ml to 300 mg/ml | 75 mg/ml to 300 mg/ml, such as 150 mg/ml to about 250 mg/ml |
| Oil (e.g., corn oil, sesame oil, peanut oil, cottonseed oil, and/or Miglyol 812) | 30% to 100% of solvent | 50% to 90% of solvent | 60% to 90% of solvent, such as 70% |
| Co-solvent 1 (e.g., benzyl alcohol) | 0% to 20% of solvent | 0% to 15% of solvent | 0% to 10% of solvent, such as 10% |
| benzyl benzoate | 0% to 50% of solvent | 0% to 35% of solvent | 0% to 30% of solvent, such as 20% |
| Other optional ingredients | | | |

In some embodiments, the present disclosure also provides the following specific formulations: abiraterone acetate solution in Castor oil with a concentration of about 50 mg/mL to about 200 mg/mL (such as 70 mg/mL); abiraterone acetate solution in 10% Benzyl alcohol/90% Castor oil with a concentration of about 50 mg/mL to about 200 mg/mL (such as about 90 mg/mL); abiraterone acetate solution in 500% Benzyl benzoate/50% Castor oil with a concentration of about 50 mg/mL to about 200 mg/mL (such as about 125 mg/mL); abiraterone propionate solution in 1000 Benzyl alcohol/90% Castor oil with a concentration of about 50 mg/mL to about 300 mg/mL (such as about 200 mg/mL); abiraterone propionate solution in 1000 Benzyl alcohol/90% Corn oil with a concentration of about 50 mg/mL to about 300 mg/mL (such as about 168 mg/mL); abiraterone decanoate solution in Castor oil with a concentration of about 100 mg/mL to about 300 mg/mL (such as 160 mg/mL or 170 mg/mL); abiraterone decanoate solution in Corn oil with a concentration of about 100 mg/mL to about 300 mg/mL (such as 160 mg/mL or 170 mg/mL); abiraterone decanoate solution in 10% Benzyl alcohol/90% Castor oil with a concentration of about 100 mg/mL to about 300 mg/mL (such as 160 mg/mL or 170 mg/mL); abiraterone decanoate solution in 10% Benzyl alcohol/90% Corn oil with a concentration of about 100 mg/mL to about 300 mg/mL (such as 160 mg/mL or 170 mg/mL); abiraterone decanoate solution in 70% Corn Oil, 10% Benzyl Alcohol, 20% Benzyl Benzoate with a concentration of about 150 mg/mL to about 300 mg/mL (such as about 200 mg/ml or about 240 mg/ml); abiraterone isocaproate 90% in Corn Oil, 10% Benzyl Alcohol Solution with a concentration of about 120 mg/mL to about 200 mg/mL (such as about 150 mg/ml or about 160 mg/ml). In some embodiments, the present disclosure also provides any of the specific formulations prepared herein such as in Examples 3A-3J. In some embodiments, the present disclosure also provides a formulation described herein in Example 1.

Method of Treatment

Some embodiments of the present disclosure are directed to methods of delivering abiraterone to a subject in need thereof. In various embodiments, the present disclosure also provides methods of treating or prevent diseases or disorders for which administering abiraterone is beneficial.

In some embodiments, the present disclosure provides a method of delivering abiraterone to a subject in need thereof, the method comprising administering to the subject any of the abiraterone prodrugs or abiraterone prodrug formulations of the present disclosure. In some embodiments, the subject suffers from a sex hormone-dependent benign or malignant disorder, e.g., an androgen-dependent or an estrogen-dependent disorder as described herein. In some embodiments, the subject suffers from a syndrome due to androgen excess and/or a syndrome due to glucocorticoid excess such as hypercortisolemia, e.g., as described herein. In any of the embodiments described herein, unless directly contradictory, the subject can be a human subject, e.g., a human patient having a hormone-dependent benign or malignant disorder, a syndrome due to androgen excess, and/or a syndrome due to glucocorticoid excess such as hypercortisolemia, e.g., as described herein. Hormone-dependent benign or malignant disorder as used herein, whether preceded with the term "sex" should be understood as sex hormone-dependent benign or malignant disorder, such as androgen-dependent or estrogen-dependent disorders.

Figure 14A:
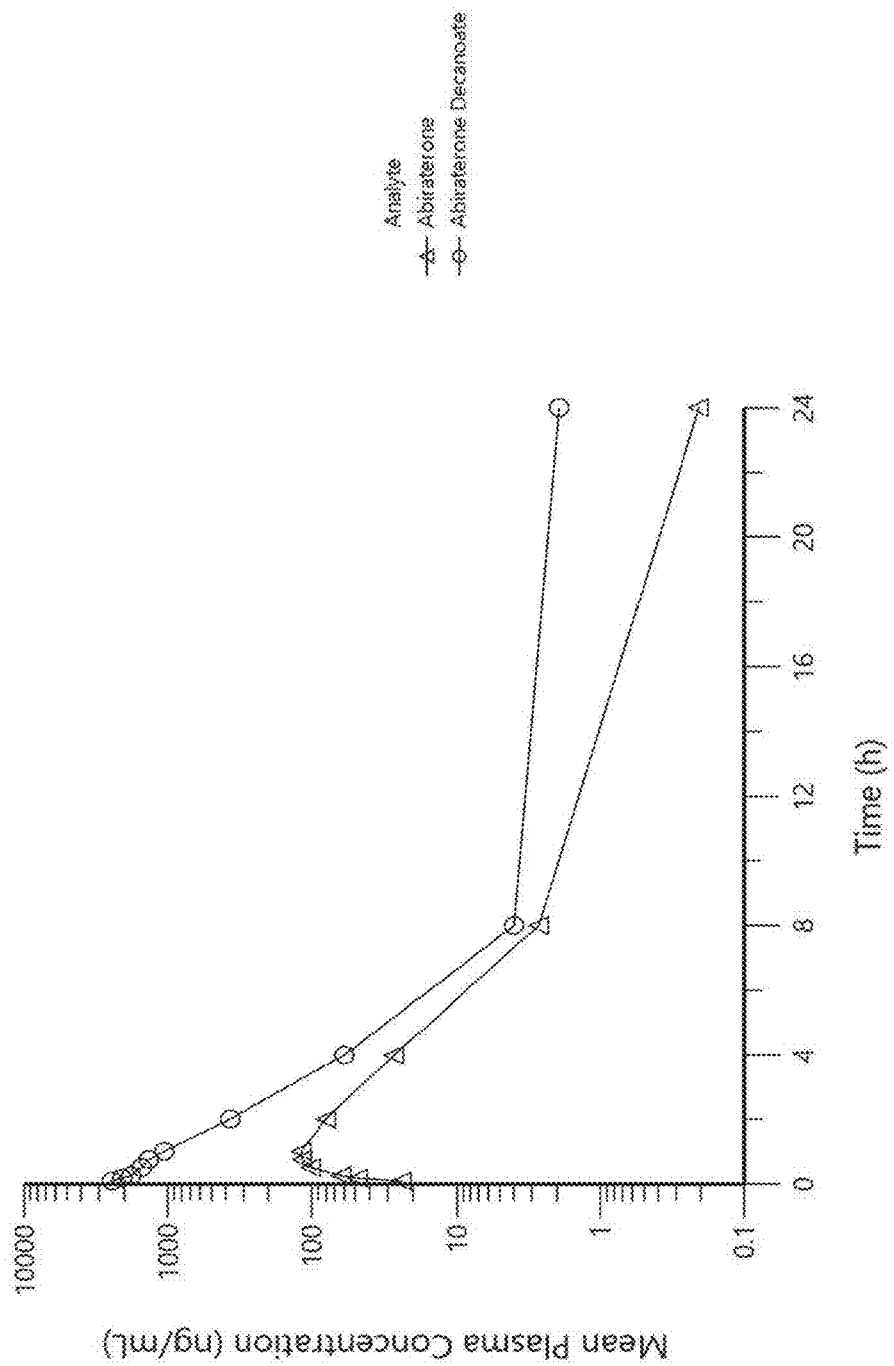
FIG. 14A shows mean abiraterone and abiraterone decanoate plasma concentration versus time profile data following IV administration of 1.2 mg/kg abiraterone decanoate (0.4 mg/ml solution in 40% HP-beta-cyclodextrin 25 mM Na phosphate buffer (pH 7.4)) in Male Cynomolgus Monkeys (n=3).
Figure 14B:
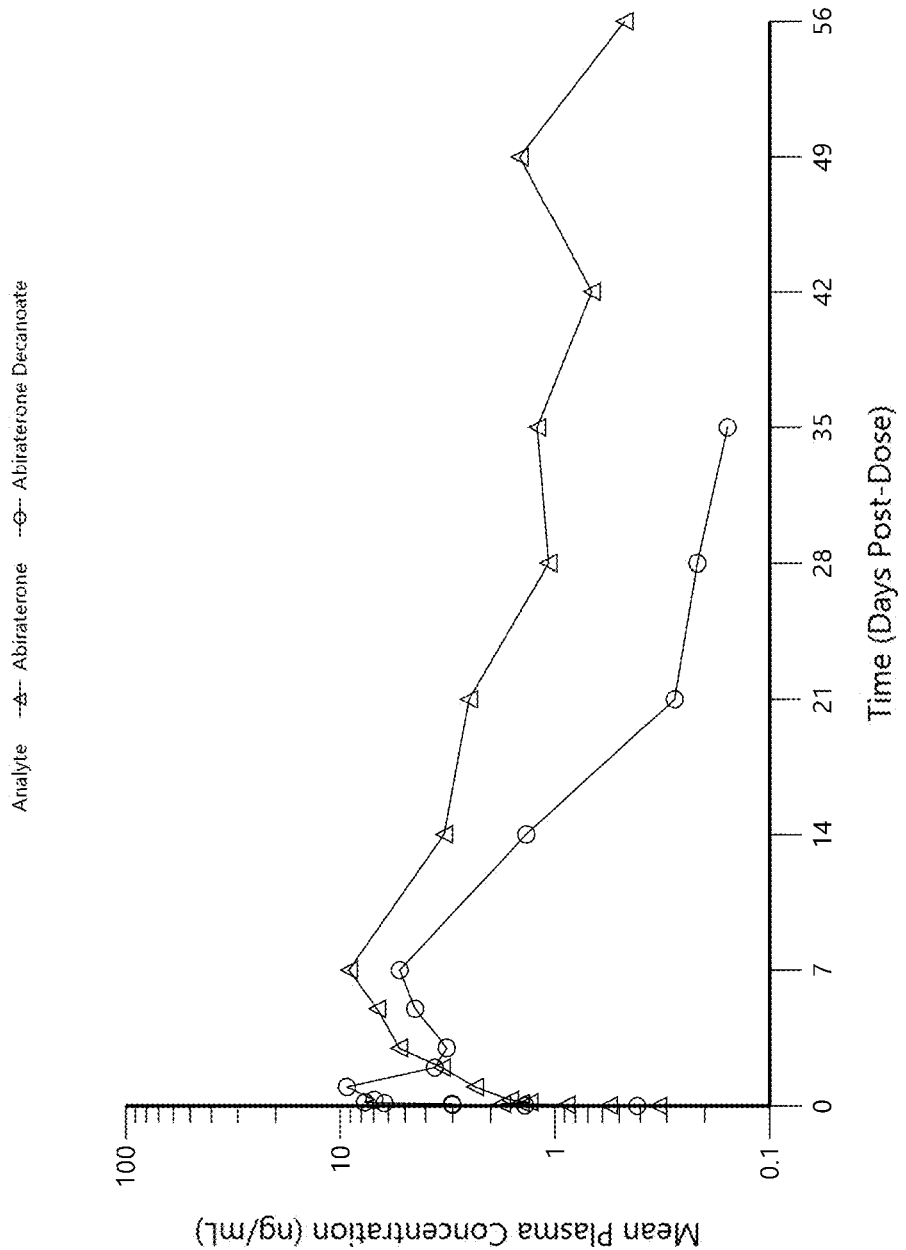
FIG. 14B shows mean abiraterone and abiraterone decanoate plasma concentration versus time profile data following a single IM administration of abiraterone decanoate formulation (90% Corn Oil, 10% Benzyl Alcohol, 192 mg/ml abiraterone decanoate) at a dose of 90 mg/kg abiraterone decanoate in Male Cynomolgus Monkeys (n=3).
Figure 14C:
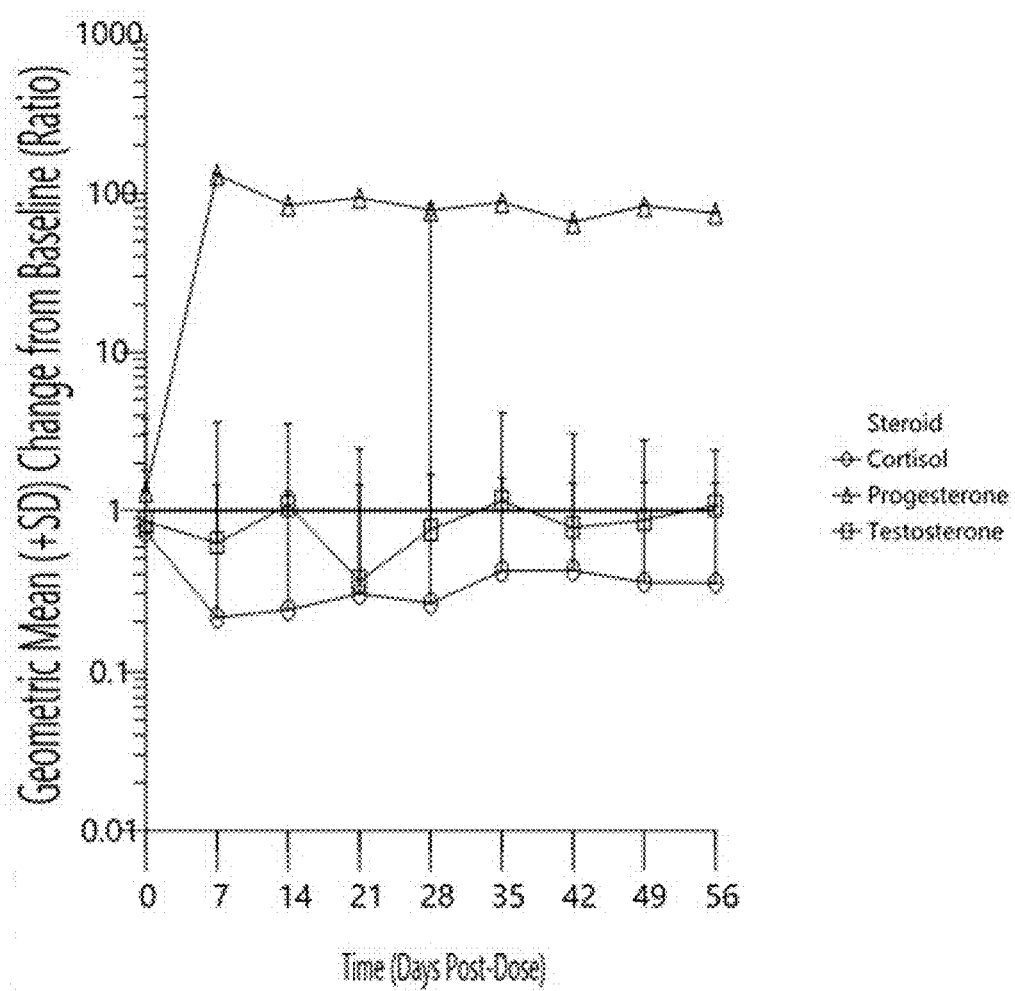
FIG. 14C shows the observed steroid levels (progesterone, cortisol and testosterone levels) versus time profile data following this single dose IM administration.
Figure 14D:
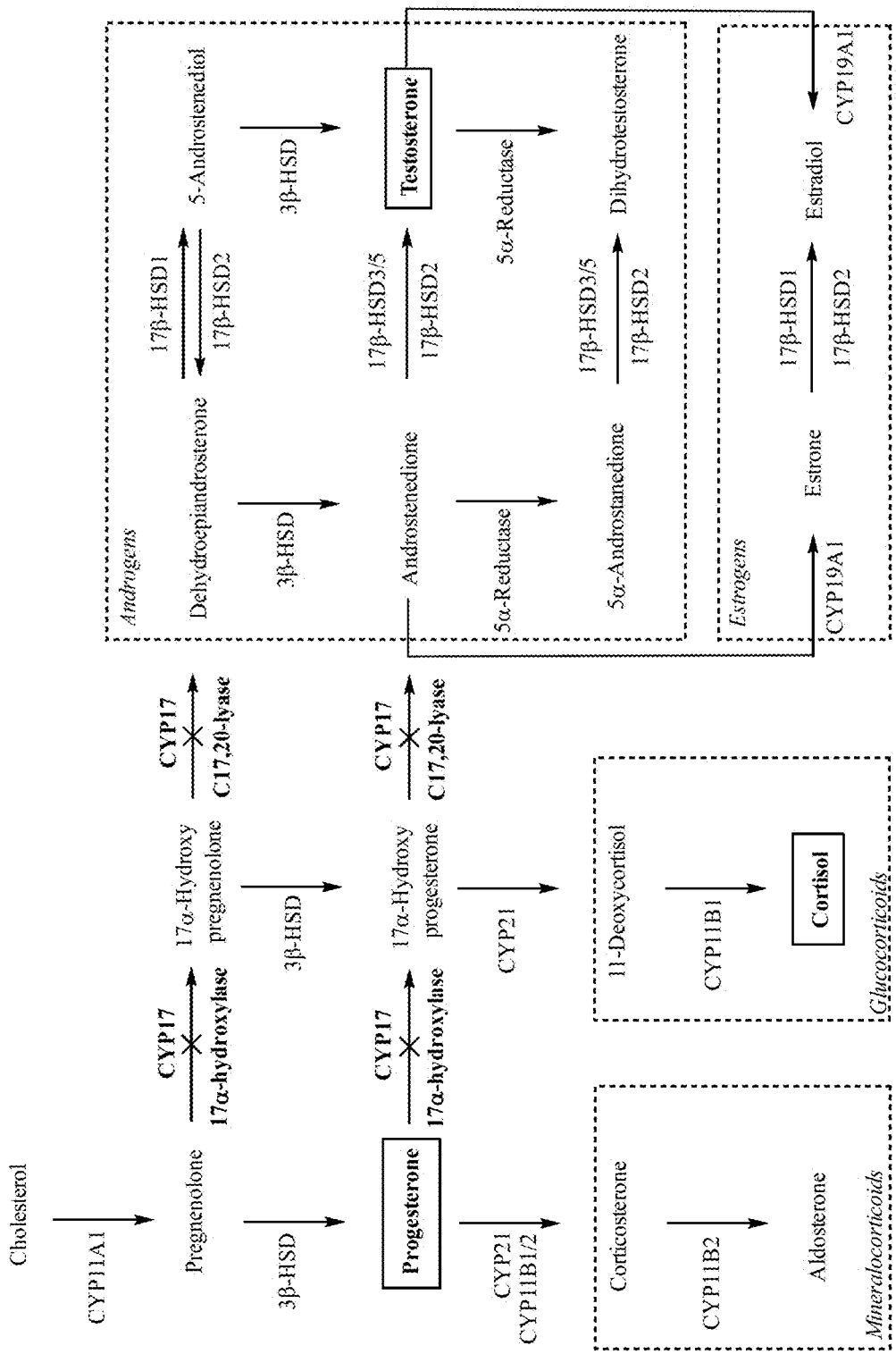
FIG. 14D presents biochemical pathways showing the effects of CYP17A1 inhibition on the synthesis of androgens, estrogens, glucocorticoids, progesterone and mineralocorticoids.

As detailed herein, in a monkey PK study, it was shown that a single intramuscular injection of a representative abiraterone prodrug, abiraterone decanoate, can achieve a prolonged CYP17A1 inhibition, with sustained increase of progesterone level and reduction of cortisol and testosterone level up to eight weeks. As shown in FIG. 14D, it is expected that inhibition of CYP17A1 17α-hydroxylase and C17,20-lyase activities will lead to (1) increases in levels of progesterone and the mineralocorticoids; (2) reductions in levels of glucocorticoids such as cortisol; and (3) reductions in levels of sex hormones, e.g., androgens such as testosterone and dihydrotestosterone, and estrogens such as estradiol. Thus, the abiraterone prodrugs and prodrug formulations of the present disclosure can be advantageously used for inhibiting CYP17A1 activity, reducing glucocorticoids levels, such as cortisol levels, reducing sex hormone levels such as androgen and/or estrogen levels, and/or treating disorders associated with high glucocorticoids levels, such as cortisol levels, and/or treating disorders due to high sex hormone levels such as androgen and/or estrogen levels.

In some embodiments, the present disclosure provides a method of inhibiting CYP17A1 activity such as inhibiting 17α-hydroxylase activity and 17,20-lyase activity, the method comprising administering to the subject any of the abiraterone prodrugs or abiraterone prodrug formulations of the present disclosure. In some embodiments, the subject suffers from a sex hormone-dependent benign or malignant disorder, e.g., as described herein. In some embodiments, the subject suffers from a syndrome due to androgen excess and/or a syndrome due to glucocorticoid excess such as hypercortisolemia, e.g., as described herein.

In some embodiments, the present disclosure provides a method of reducing the level of glucocorticoids (e.g., cortisol) in a subject in need thereof, the method comprising administering to the subject any of the abiraterone prodrugs or abiraterone prodrug formulations of the present disclosure. In some embodiments, the subject suffers from a syndrome due to glucocorticoid excess such as hypercortisolemia as described herein, such as Cushing's syndrome or Cushing's disease.

In some embodiments, the present disclosure provides a method of reducing the level of androgens (e.g., testosterone and/or dihydrotestosterone) and/or estrogens in a subject in need thereof, the method comprising administering to the subject any of the abiraterone prodrugs or abiraterone prodrug formulations of the present disclosure. In some embodiments, the subject suffers from a syndrome due to androgen excess, such as congenital adrenal hyperplasia (e.g., classical or nonclassical congenital adrenal hyperplasia), endometriosis, polycystic ovary syndrome precocious puberty, hirsutism, etc. In some embodiments, the subject suffers from an androgen and/or estrogen associated cancer, such as prostate cancer or breast cancer.

In some embodiments, a method of treating a sex hormone-dependent benign or malignant disorder, a syndrome due to androgen excess and/or a syndrome due to glucocorticoid excess such as hypercortisolemia is provided. Typically, the method comprises administering to a subject in need thereof a therapeutically effective amount of any of the abiraterone prodrugs or abiraterone prodrug formulations of the present disclosure. In any of the embodiments described herein, unless directly contradictory, the subject can be a human subject, e.g., a human patient having a hormone-dependent benign or malignant disorder, a syndrome due to androgen excess and/or a syndrome due to glucocorticoid excess such as hypercortisolemia, e.g., as described herein.

The administering in the methods herein is not limited to any particular route. However, in some preferred embodiments, the administering can be a parenteral administration, such as an intramuscular injection, intradermal injection, or subcutaneous injection. Parenteral administration can in some embodiments be advantageous. For example, in some embodiments, the administering can be a parenteral administration, such as an intramuscular injection, which can be carried out without regard to whether the subject has food. In other words, the fed or fasted status of the subject is not important. This removes the restriction associated with the currently marketed Zytiga® formulation, which states that the medication "must be taken on an empty stomach with water at least 1 hour before or 2 hours after a meal." Therefore, among other advantages, the methods herein can improve patient compliance.

Various sex hormone-dependent benign or malignant disorders can be treated with the methods herein. In some embodiments, the hormone-dependent benign or malignant disorders can be androgen-dependent disorders and estrogen-dependent disorders such as androgen or estrogen-dependent cancers. In some embodiments, the sex hormone-dependent benign or malignant disorder can be prostate cancer or breast cancer. In some embodiments, the sex hormone-dependent benign or malignant disorder is castration resistant prostate cancer or castration sensitive prostate cancer. In some embodiments, the sex hormone-dependent benign or malignant disorder can be metastatic castration resistant prostate cancer or metastatic castration sensitive prostate cancer. In some embodiments, the sex hormone-dependent benign or malignant disorder can also be ovarian cancer, bladder cancer, hepatocellular carcinoma, or lung cancer. Various non-oncologic syndromes due to androgen excess and/or due to glucocorticoid excess such as hypercortisolemia can also be treated with the methods herein, for example, syndromes due to androgen excess such as endometriosis, polycystic ovary syndrome, classical or nonclassical congenital adrenal hyperplasia, precocious puberty, hirsutism, etc., and/or syndromes due to cortisole excess such as Cushing's syndrome, Cushing's disease, etc.

The methods herein can be used in conjunction with one or more additional therapies for the respective disease or disorder. For example, the Zytiga® label (abiraterone acetate) states that patients receiving Zytiga® should also receive a gonadotropin-releasing hormone (GnRH) analog concurrently or should have had bilateral orchiectomy. Accordingly, in some embodiments of methods of the present disclosure, the subject can also be treated with a gonadotropin-releasing hormone analog and/or bilateral orchiectomy. In some embodiments, the method also comprises administering to the subject an effective amount of prednisone or prednisolone, either concurrently or sequentially. However, in some embodiments, the methods herein can also achieve the desired therapeutic effect without causing adrenocortical insufficiency, which thus can avoid co-administering prednisone or prednisolone. In some embodiments, the subject is not treated with a gonadotropin-releasing hormone analog and/or bilateral orchiectomy. In some embodiments, the subject is not administered with prednisone or prednisolone.

In some embodiments, the method can comprise administering one or more other drug or agent (for example, another cancer chemotherapeutic drug, hormone replacement drug, or hormone ablation drug) to the subject, either concurrently or sequentially, through the same route or a different route of administration. In some embodiments, the other drug or agent can be a steroid, such as prednisone, prednisolone, and/or methylprednisolone. In some embodiments, the other drug or agent can be a chemotherapy drug, such as paclitaxel, mitoxantrone, and/or docetaxel. In some embodiments, the other agent or drug can be a GnRH agonist, such as Leuprolide, deslorelin, goserelin, or triptorelin, e.g., leuprolide acetate (e.g., a long acting IM injectable formulation). In some embodiments, the other agent or drug can be seocalcitol, bicalutamide, flutamide, a glucocorticoid including, but not limited to, hydrocortisone, prednisone, prednisolone, or dexamethasone. The amount of the other drugs or agents to be administered can vary, typically can be an amount that is effective in treating the respective disease or disorder (e.g., prostate cancer) either alone or in combination with the abiraterone prodrug or abiraterone prodrug formulation of the present disclosure.

Additional suitable other drugs or agents include those described herein. For example, useful other drugs or agents include, but are not limited to, anticancer agents, hormone ablation agents, anti-androgen agents, differentiating agents, anti-neoplastic agents, kinase inhibitors, anti-metabolite agents, alkylating agents, antibiotic agents, immunological agents, interferon-type agents, intercalating agents, growth factor inhibitors, cell cycle inhibitors, enzymes, topoisomerase inhibitors, biological response modifiers, mitotic inhibitors, matrix metalloprotease inhibitors, genetic therapeutics, and anti-androgens.

For example, suitable anti-cancer agents, including but not limited to, acemannan, aclarubicin, aldesleukin, alemtuzumab, alitretinoin, altretamine, amifostine, amsacrine, anagrelide, anastrozole, ancestim, bexarotene, broxuridine, capecitabine, celmoleukin, cetrorelix, cladribine, clotrimazole, daclizumab, dexrazoxane, dilazep, docosanol, doxifluridine, bromocriptine, carmustine, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, metoclopramide, mifepristone, miltefosine, mirimostim, mitoguazone, mitolactol, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, raloxifene, raltitrexed, rasburicase, rituximab, romurtide, sargramostim, sizofiran, sobuzoxane, sonermin, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vinorelbine. Suitable anti-androgen agents include but are not limited to bicalutamide, flutamide and nilutamide. Suitable differentiating agents include, but are not limited to, polyamine inhibitors; vitamin D and its analogs, such as, calcitriol, doxercalciferol and seocalcitol; metabolites of vitamin A, such as, ATRA, retinoic acid, retinoids; short-chain fatty acids; phenylbutyrate; and nonsteroidal anti-inflammatory agents. anti-neoplastic agent, including, but not limited to, tubulin interacting agents, topoisomerase inhibitors and agents, acitretin, alstonine, amonafide, amphethinile, amsacrine, ankinomycin, anti-neoplaston, aphidicolin glycinate, asparaginase, baccharin, batracylin, benfluron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, epothilones, ergotamine, etoposide, etretinate, fenretinide, gallium nitrate, genkwadaphnin, hexadecylphosphocholine, homoharringtonine, hydroxyurea, ilmofosine, isoglutamine, isotretinoin, leukoregulin, lonidamine, merbarone, merocyanine derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, ocreotide, oquizanocinc, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, and withanolides. a kinase inhibitor including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, SOD mimics or $\alpha_v\beta_3$ inhibitors. Suitable anti-metabolite agents may be selected from, but not limited to, 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, isopropyl pyrrolizine, methobenzaprim, methotrexate, norspermidine, pentostatin, piritrexim, plicamycin, thioguanine, tiazofurin, trimetrexate, tyrosine kinase inhibitors, and uricytin. Suitable alkylating agents may be selected from, but not limited to, aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol. Suitable antibiotic agents may be selected from, but not limited to, aclarubicin, actinomycin D, actinoplanone, adriamycin, aeroplysinin derivative, amrubicin, anthracycline, azino-mycin-A, bisucaberin, bleomycin sulfate, bryostatin-1, calichemycin, chromoximycin, dactinomycin, daunorubicin, ditrisarubicin B, dexamethasone, doxorubicin, doxorubicin-fibrinogen, elsamicin-A, epirubicin, erbstatin, esorubicin, esperamicin-A1, esperamicin-Alb, fostriecin, glidobactin, gregatin-A, grincamycin, herbimycin, corticosteroids such as hydrocortisone, idarubicin, illudins, kazusamycin, kesarirhodins, menogaril, mitomycin, neoenactin, oxalysine, oxaunomycin, peplomycin, pilatin, pirarubicin, porothramycin, prednisone, prednisolone, pyrindanycin A, rapamycin, rhizoxin, rodorubicin, sibanomicin, siwenmycin, sorangicin-A, sparsomycin, talisomycin, terpentecin, thrazine, tricrozarin A, and zorubicin. Non-limiting examples of suitable steroids include hydrocortisone, prednisone, prednisolone, or dexamethasone.

Dosing Regimen

The abiraterone prodrugs and formulations of the present disclosure can generally provide a long-acting release of abiraterone to a subject user. This long-acting release profile allows administering abiraterone to a subject user at a low dosing frequency, such as once a week or even less frequently, which can improve patient compliance and reduce pill burdens.

In some embodiments, the methods herein can have a dosing regimen of once a week or once in more than a week. Typically, the dosing frequency can range from once a week to once every few months, such as from once a week to once every eight weeks, or from once a week to once every three months. In some embodiments, the dosing amount for each dose is about 50 mg to about 2000 mg (e.g., about 500 mg, about 1000 mg, about 1500 mg, or any ranges between the recited values) of abiraterone prodrug. In some embodiments, the dosing amount of abiraterone prodrug for each dose is about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of a subject. In some embodiments, the methods herein can comprise administering to the subject in need thereof an abiraterone prodrug or abiraterone prodrug formulation of the present disclosure, once a week, or once in more than a week, such as once in two weeks, once in a month, wherein the administering provides a therapeutically effective plasma concentration (e.g., as described herein, such as 0.5 ng/ml and above, 1 ng/ml and above, 8 ng/ml and above, or 8.4 ng/ml and above) of abiraterone in the subject for a prolong period of time, such as more than 1 week, more than 2 weeks, more than 3 weeks, more than 4 weeks, and up to six or eight weeks or more, etc. In some embodiments, the administering can provide a single dose $C_{max}$ of abiraterone between about 10 ng/ml and about 400 ng/ml (e.g., between about 50 ng/ml and about 100 ng/ml, or between about 15 ng/ml and about 160 ng/ml). In some embodiments, the administering can provide a steady state $C_{max}$ of abiraterone between about 10 ng/ml and about 400 ng/ml (e.g., between about 50 ng/ml and about 100 ng/ml, or between about 15 ng/ml and about 160 ng/ml). In some embodiments, the administering can provide a single dose $C_{min}$ of abiraterone between about 1 ng/ml and about 8 ng/ml, or above about 8 ng/ml such as above 8.4 ng/ml, at each day from day 1 to day 7, or day 1 to day 14, or day 1 to day 21, or day 1 to day 28 post administration. In some embodiments, the administering can provide a steady state $C_{min}$ of abiraterone between about 1 ng/ml and about 8 ng/ml, or above about 8 ng/ml such as above 8.4 ng/ml.

Abiraterone prodrugs suitable for use for a once a week or once in more than a week dosing methods above include those described herein. In some embodiments, the abiraterone prodrug can be a lipophilic ester of abiraterone described herein, for example, an acetate, a propionate, a butanoate, a (vaterate) pentanoate, an isocaproate, a buciclate, a cyclohexanecarboxylate, a phenyl propionate, caproate (hexanoate), a enanthate (heptanoate), a cypionate, an octanoate, a noncanoate, a decanoate, an undecanoate, a dodecanoate, a tridecanoate, a tetradecanoate, a pentadecanoates, and a hexadecanoate. In some preferred embodiments, the abiraterone prodrug can be a compound of Formula I, for example, a compound of Formula I, wherein $R^1$ is a $C_{7-16}$ alkyl, e.g., an alkyl having a formula of —$(CH_2)_n$—$CH_3$, wherein n is an integer between 6 and 12 (e.g., n is 6, 7, 8, 9, 10); or $R^1$ is represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl; or $R^1$ is

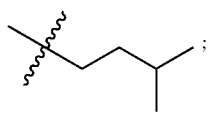 [SMILES: *CCC(C)C]

or $R^1$ is

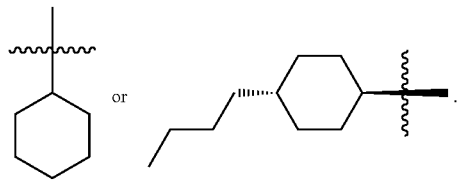

In some embodiments, the abiraterone prodrug can be a compound of Formula II, wherein $R^2$ in Formula II can be a $C_{1-16}$ alkyl, e.g., an alkyl having a formula of —$(CH_2)_n$—$CH_3$, wherein n is an integer between 0 and 12; or $R^2$ in Formula II can be represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl; or $R^2$ in Formula II can be

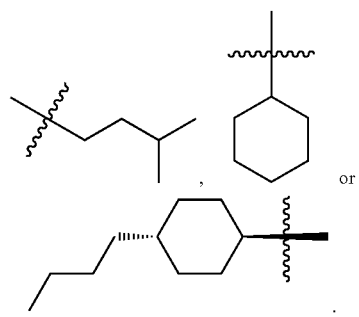

In some embodiments, the abiraterone prodrug can also be abiraterone acetate or any of the Examples 2A-2H. In some embodiments, the abiraterone prodrug can be abiraterone acetate, abiraterone propionate, or abiraterone decanoate. In some specific embodiments, the abiraterone ester can be abiraterone pentanoate, abiraterone hexanoate, abiraterone heptanoate, abiraterone decanoate, abiraterone isocaproate, or abiraterone cypionate. In any of the embodiments described herein, unless otherwise specified or directly contradictory from context, the abiraterone prodrug can be abiraterone decanoate.

In some embodiments, a once a month or once in more than a month dosing is desired, e.g., the dosing frequency ranges from once a month to once every few months, such as from once a month to once every two months, or from once a month to once every three months. In such embodiments, the abiraterone prodrug needs to not only release abiraterone slowly but also to release abiraterone in a sufficient plasma concentration such that it can be beneficial to the subject user. The once a month or once in more than a month dosing is typically a parenteral administration, such as intramuscularly, intradermally, or subcutaneously. In any of the embodiments herein, unless directly contradictory, the administration can be an intramuscular administration.

As detailed herein, a single intramuscular administration of abiraterone acetate was found to provide extended release of abiraterone. However, the dog PK study shows that similar administration of abiraterone propionate did not improve the extend release of abiraterone acetate, and in fact, the abiraterone release observed from the propionate was below that observed for the acetate at all time points measured. Further, it was also unexpectedly found that elongation of the alkyl chain to abiraterone butanoate led to a sharp reduction of solubility in various oil vehicle. Despite of this unexpected trend, the present inventors found that certain abiraterone prodrugs or abiraterone prodrug formulations of the present disclosure, for example, compounds of Formula I, such as abiraterone decanoate, can be superior for use in a once a month or once in more than a month dosing than the acetate, propionate, or butanoate. It was also found that the PK profile, such as $t_{1/2}$, of certain abiraterone prodrugs or abiraterone prodrug formulations of the present disclosure, for example, compounds of Formula I, such as abiraterone decanoate, does not vary significantly when a different oil vehicle is used. In contrast, as detailed in Example 5B, some variabilities of PK profiles for abiraterone propionate were observed, depending on whether it was formulated in castor oil or corn oil.

In some specific embodiments, the present disclosure provides a method of treating a sex hormone-dependent benign or malignant disorder (e.g., as described herein), a syndrome due to androgen excess, and/or a syndrome due to glucocorticoid excess such as hypercortisolemia, in a subject in need thereof, the method comprising parenterally administering to the subject a therapeutically effective amount of a compound of Formula I (e.g., described herein), or a pharmaceutical composition comprising the compound of Formula I (e.g., described herein), once a month or once in more than a month. In some embodiments, the parenterally administering is intramuscularly, intradermally, or subcutaneously administering. In some preferred embodiments, in the compound of Formula I, $R^1$ is a $C_{7-16}$ alkyl, e.g., an alkyl having a formula of $-(CH_2)_n-CH_3$, wherein n is an integer between 6 and 12 (e.g., n is 6, 7, 8, 9, or 10); or $R^1$ is represented by the formula $-(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl; or $R^1$ is

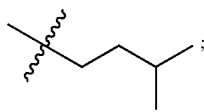 [SMILES: *CCC(C)C]

or $R^1$ is

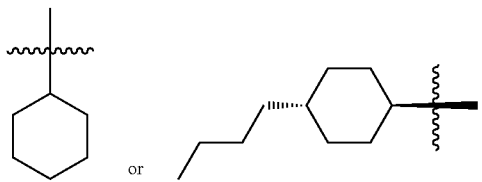

In some embodiments, the administering provides a therapeutically effective blood plasma concentration of abiraterone in the subject for a period of at least 4 weeks, such as at least 5 weeks, and up to six or eight weeks or more, etc. In some embodiments, the therapeutic blood plasma concentration of abiraterone can be a concentration of at least 1 ng/ml, e.g., at least 2 ng/ml, at least 4 ng/ml, at least 8 ng/ml. In some embodiments, the therapeutically effective blood plasma concentration of abiraterone can also be about 0.5 ng/ml or higher. In some embodiments, the administering can provide a single dose $C_{max}$ of abiraterone between about 10 ng/ml and about 400 ng/ml (e.g., between about 50 ng/ml and about 100 ng/ml, or about 15 ng/ml and about 160 ng/ml). In some embodiments, the administering can provide a steady state $C_{max}$ of abiraterone between about 10 ng/ml and about 400 ng/ml (e.g., between about 50 ng/ml and about 100 ng/ml, or between about 15 ng/ml and about 160 ng/ml). In some embodiments, the administering can provide a single dose $C_{min}$ of abiraterone at day 28 post administration between about 1 ng/ml and about 8 ng/ml, or above about 8 ng/ml, e.g., above about 8.4 ng/ml. In some embodiments, the administering can provide a steady state $C_{min}$ of abiraterone between about 1 ng/ml and about 8 ng/ml, or above about 8 ng/ml, e.g., above about 8.4 ng/ml. In some embodiments, the blood plasma concentration of abiraterone in the subject can remain substantially constant, e.g., for at least 1 week, e.g., between 1 week and 3 weeks post administration. In some embodiments, the administering is carried out without regard to whether the subject has food. In some embodiments, the administering provides a single dose $C_{max}$ of abiraterone reduced by at least 30% compared to the $C_{max}$ of abiraterone observed at steady state for a once daily oral dose of Zytiga® at 1000 mg without food. In some embodiments, the administering provides a steady state $C_{max}$ of abiraterone reduced by at least 30% compared to the $C_{max}$ of abiraterone observed at steady state for a once daily oral dose of Zytiga® at 1000 mg without food. In some embodiments, the pharmaceutical composition comprising the compound of Formula I can be formulated as a unit dosage form described herein. Suitable carriers, oil vehicles, excipients for such pharmaceutical compositions include those described herein.

The abiraterone prodrugs and abiraterone prodrug formulations of the present disclosure can be administered to a subject in need thereof as the only source of abiraterone. However, in some embodiments, other abiraterone medications/formulations are not excluded. For example, in some embodiments, the administering herein can be combined, either concurrently or sequentially in any order, with an oral administration of abiraterone acetate, such as the Zytiga® formulation. In some embodiments, the subject can use the abiraterone prodrugs and abiraterone prodrug formulations as a supplement to an existing abiraterone therapy. Moreover, the administering herein is not limited to administering a single abiraterone prodrug or abiraterone prodrug formulation of the present disclosure. In some embodiments, two or more abiraterone prodrugs and abiraterone prodrug formulations of the present disclosure can be administered to the subject.

In some embodiments, prior to a once a month or once in more than a month dosing, the methods herein can include an initial treatment period with a higher dosing frequency, such as a once a week or once in two weeks dosing. The initial treatment period can include administering the same abiraterone prodrug or a different abiraterone medication such as a different abiraterone prodrug. Typically, the initial treatment period can be used to achieve a blood plasma concentration of abiraterone of about 1 ng/ml to about 8 ng/ml or above about 8 ng/ml, prior to the once a month or once in more than a month dosing described herein. However, in some embodiments, the methods herein do not include such initial treatment period.

As discussed herein, the abiraterone prodrugs and abiraterone prodrug formulations of the present disclosure have many advantages over the currently marketed Zytiga® product. For example, administering the abiraterone prodrugs and abiraterone prodrug formulations of the present disclosure to a subject typically results in reduced $C_{max}$ of abiraterone (e.g., reduced by at least 30% compared to the $C_{max}$ of abiraterone observed at steady state for a once daily oral dose of Zytiga® at 1000 mg without food).

Thus, in some embodiments, the present disclosure provides a method of treating subjects having side effects related to high abiraterone exposure, such as having abiraterone $C_{max}$ related side effects, the method comprising administering abiraterone prodrugs and abiraterone prodrug formulations of the present disclosure to the subject, wherein the administering reduces the side effects when compared to administering of a once daily oral dose of Zytiga® at 1000 mg without food. Suitable routes of administration, dosing amounts, frequencies include those described herein. Various side effects or adverse effects are described in the Zytiga® prescribing information approved by the FDA, see e.g., the February 2018 or June 2019 version. In some embodiments, the present disclosure provides a method of treating subjects who are also administered a drug, the metabolism of which is inhibited by abiraterone, for example, drugs that are CYP2D6 and/or CYP2C8 substrates, the method comprising administering to the subject the abiraterone prodrugs and abiraterone prodrug formulations of the present disclosure, wherein the administering reduces the inhibition of the metabolism of the drug when compared to administering of a once daily oral dose of Zytiga® at 1000 mg without food. In some embodiments, the present disclosure provides a method of treating a subject who has, or is at risk of having, hypertension, hypokalemia, or fluid retention due to mineralocorticoid excess, the method comprising administering to the subject the abiraterone prodrugs and abiraterone prodrug formulations of the present disclosure, wherein the administering reduces hypertension, hypokalemia, and fluid retention or the risk of hypertension, hypokalemia, and fluid retention when compared to administering of a once daily oral dose of Zytiga® at 1000 mg without food. In some embodiments, the present disclosure provides a method of treating a subject who has, or is at risk of having, adrenocortical insufficiency, the method comprising administering to the subject the abiraterone prodrugs and abiraterone prodrug formulations of the present disclosure, wherein the administering reduces adrenocortical insufficiency or the risk of having adrenocortical insufficiency when compared to administering of a once daily oral dose of Zytiga® at 1000 mg without food. In some embodiments, the present disclosure provides a method of treating a subject who has severe or fatal hepatotoxicity after taking Zytiga®, the method comprising administering to the subject the abiraterone prodrugs and abiraterone prodrug formulations of the present disclosure, wherein the administering reduces hepatotoxicity. Without wishing to be bound by theories, it is believed that administering the abiraterone prodrugs and abiraterone prodrug formulations of the present disclosure typically results in a reduced, yet efficacious abiraterone exposure and therefore is beneficial for subjects who need a lower dose of abiraterone, e.g., as described above. Suitable dosing regimens, routes of administrations include those described herein.

Abiraterone Decanoate

Figure 16A:
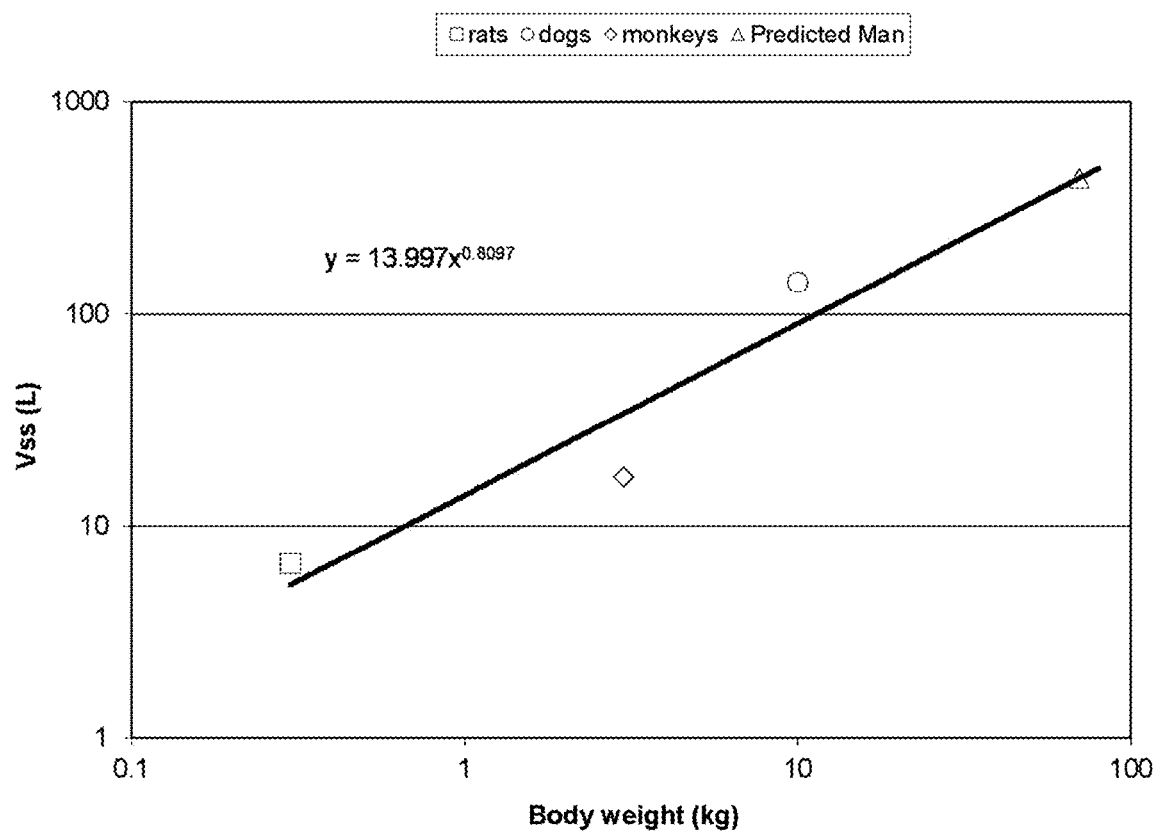
FIG. 16A shows allometric scaling of distribution volume (Vss) of abiraterone in rats, dogs and monkeys, with prediction in man.
Figure 16B:
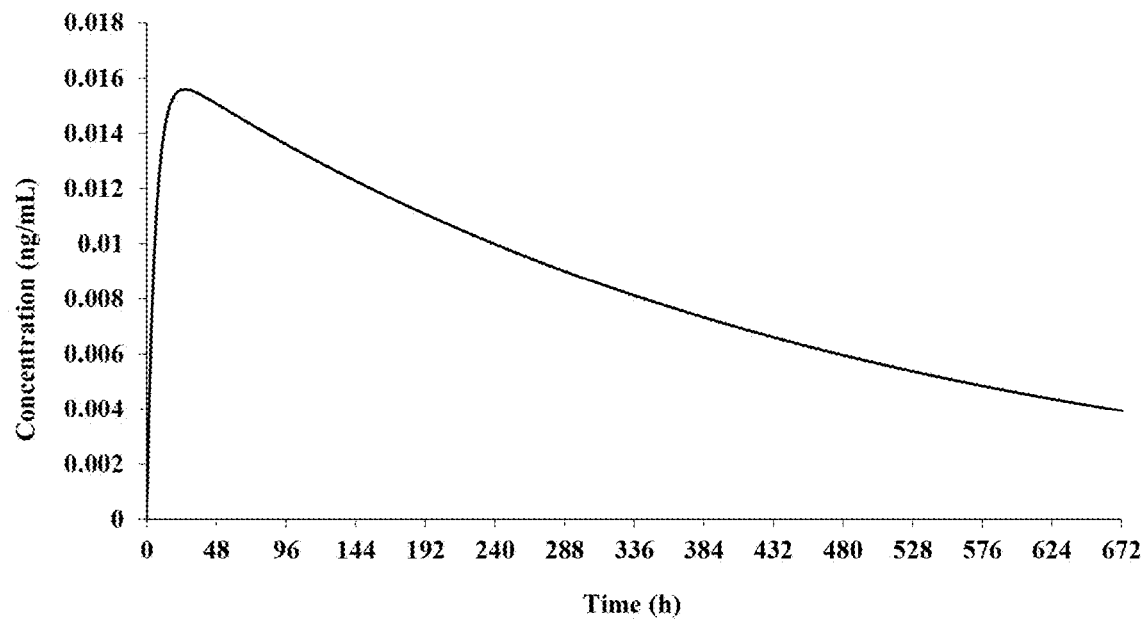
FIG. 16B shows predicted plasma profile of abiraterone in man following a single intramuscular dose of abiraterone at 1 mg based on a bioavailability of 56%.
Figure 16C:
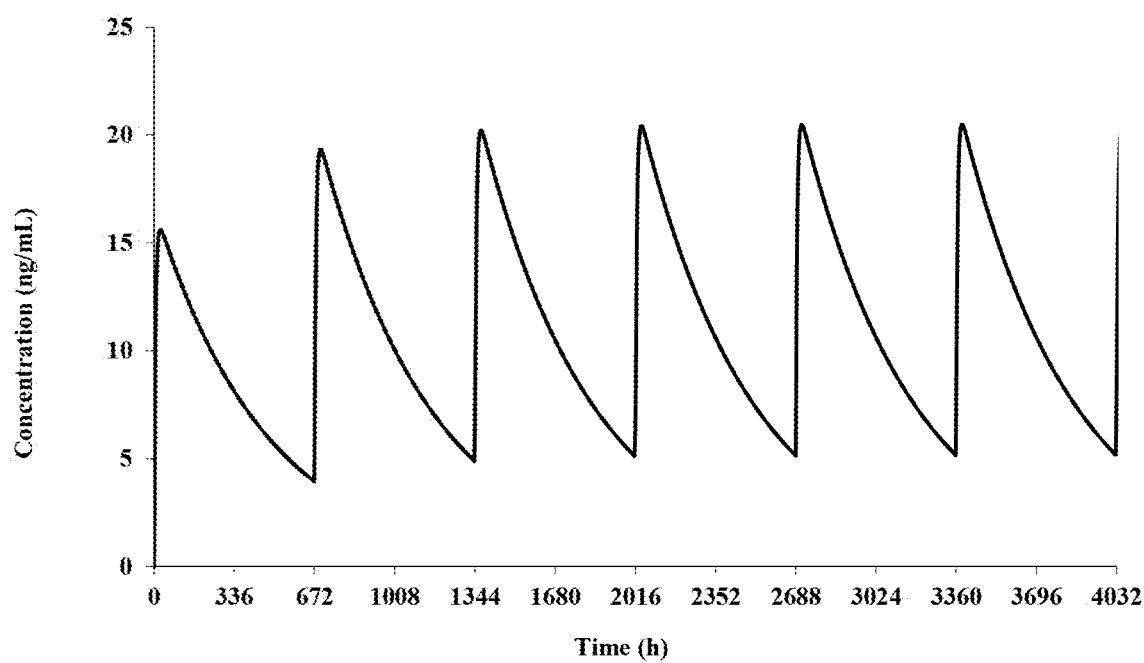
FIG. 16C shows predicted plasma profile of abiraterone in man following repeated intramuscular doses of abiraterone decanoate at 1000 mg every 4 weeks based on a bioavailability of 56%.

Some embodiments of the present disclosure are specifically directed to abiraterone decanoate. As discussed in more details in the Examples section, pharmacokinetic studies show that intramuscular injection of abiraterone decanoate formulations can provide a therapeutically effective amount of plasma abiraterone for an extended period of time in various animal models. In the monkey PK studies, it was further shown that a single intramuscular injection of abiraterone decanoate formulation can achieve a prolonged CYP17A1 inhibition, with sustained increase of progesterone level and reduction of cortisol and testosterone level. Further, based on the PK studies in rats, dogs, and monkeys, a human PK prediction was made based on allometric scaling. As shown in FIG. 16C, based on allometric scaling, it was predicted that following intramuscular doses of abiraterone decanoate, once in every 4 weeks with about 1000 mg each dose, to a human, a $C_{min}$ is expected to be at 5 ng/mL at steady state. Additionally, as detailed in the Examples section and FIG. 14F, it was unexpectedly found that abiraterone decanoate formulations with certain combination of oil and solvents can achieve significantly higher abiraterone plasma concentrations in monkeys following IM injections compared to abiraterone decanoate formulation in 90% corn oil and 10% benzyl alcohol at the same dose, with abiraterone decanoate concentration substantially the same. Thus, the dosing amount of abiraterone decanoate needed to achieve the predicted $C_{min}$ of 5 ng/mL at steady state can be lowered. Alternatively, the steady state $C_{min}$ can also be increased to above the predicted level of 5 ng/mL. These disclosures demonstrate that abiraterone can be delivered in a therapeutically effective amount to a subject (e.g., a human subject) by injection of an abiraterone prodrug, such as an abiraterone lipophilic ester prodrug, more particularly, abiraterone decanoate, with a less frequent dosing than once a week, such as once in two weeks, once a month, or once in more than a month. Typically, the dosing frequency can range from once a week to once every few months, such as from once a week to once every eight weeks, or from once a week to once every three months, such as once a month, once every eight weeks, etc.

In some specific embodiments, the present disclosure provides a compound, which is abiraterone decanoate having the formula of:

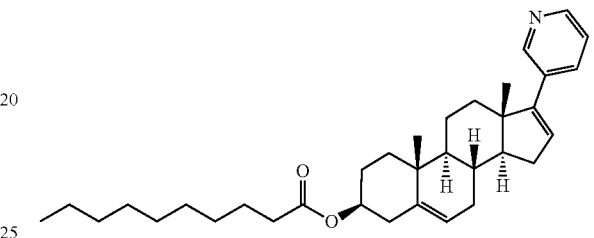

or a pharmaceutically acceptable salt thereof. In some embodiments, abiraterone decanoate can be in its basic form. In some embodiments, abiraterone decanoate can also be in a pharmaceutically acceptable salt, such as an oxalate salt, a hydrochloride salt, a benzene sulfonate salt, a p-toluene sulfonate salt, a phosphate salt, etc. In some embodiments, the salts of abiraterone decanoate can be used as a synthetic intermediate for the preparation and purification of abiraterone decanoate in its basic form. As discussed herein, abiraterone decanoate is typically present in the abiraterone prodrug formulation herein in its basic form. Unless specifically referred to as in its salt form or otherwise contradictory from context, abiraterone decanoate should be understood as in its basic form.

Abiraterone decanoate or its pharmaceutically acceptable salts can be readily prepared by those skilled in the art in view of the present disclosure. Some exemplary methods of synthesis are described herein. In some embodiments, the present disclosure provides a method of synthesizing abiraterone decanoate, which comprises reacting abiraterone with decanoic acid, or an activated form thereof, such as the corresponding acyl chloride, anhydride (e.g., mixed anhydride), etc. The reaction can be typically carried out in the presence of a coupling agent, such as a carbodiimide. As shown in the Examples section, the coupling of abiraterone and decanoic acid can be carried out in the presence of 1-Ethyl-3-(3-dimethylaminopropyl)carbodiimide, a base (such as triethyl amine) and a catalytic amount of DMAP. Salts of abiraterone decanoate can be prepared by reacting abiraterone decanoate with a suitable acid, such as oxalic acid, benzene sulfonic acid, p-toluene sulfonic acid, hydrochloric acid, or phosphoric acid, typically in an organic solvent such as isopropyl acetate, ethyl acetate, etc.

Figure 12A:
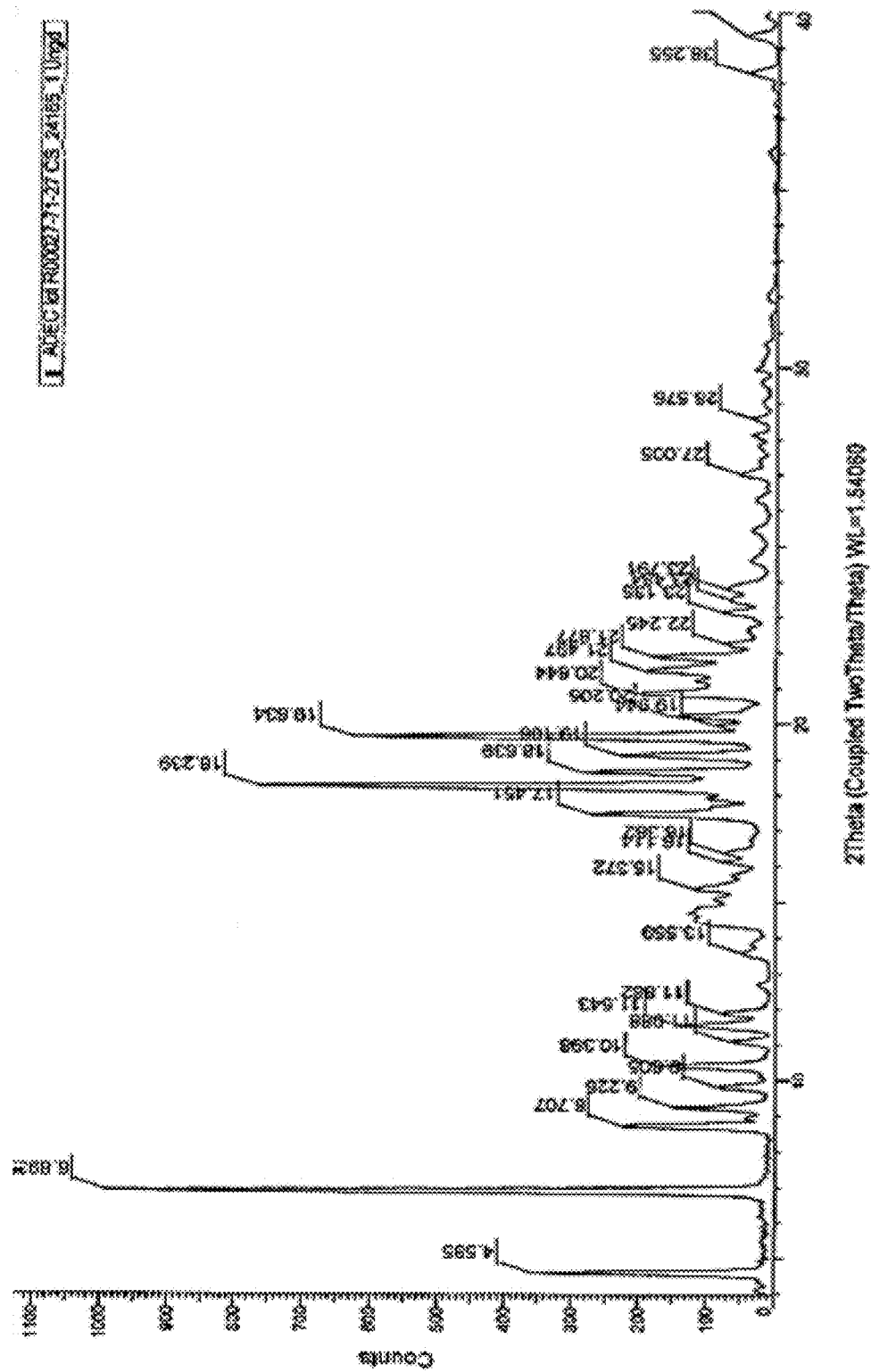
FIG. 12A presents a representative X-ray Powder Diffraction (XRPD) spectrum of the abiraterone decanoate solid form prepared in Example 6A.
Figure 12B:
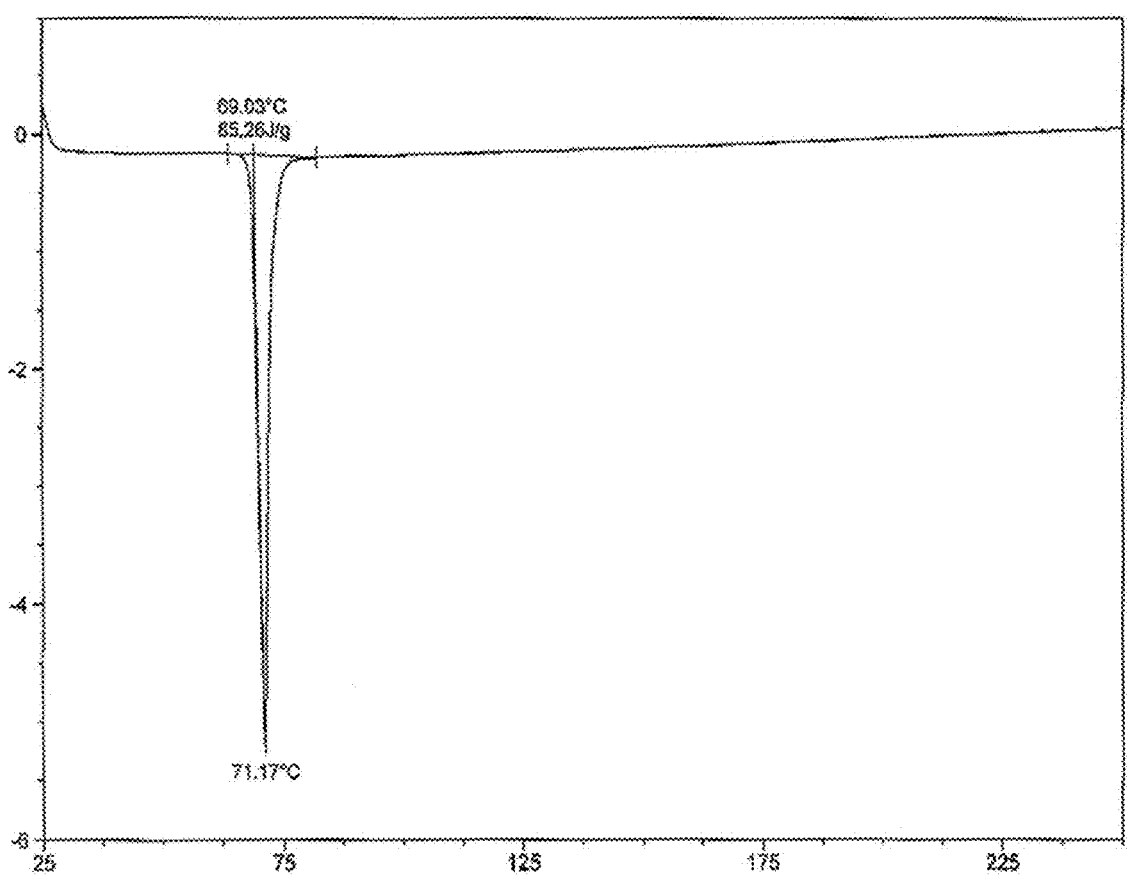
FIG. 12B shows a Differential Scanning Calorimetry (DSC) spectrum of the abiraterone decanoate solid form prepared in Example 6A.

In some embodiments, abiraterone decanoate can exist in a solid form such as a crystalline form, an amorphous form, or a combination thereof. For example, in some embodiments, the present disclosure provides abiraterone decanoate in a crystalline form. In some embodiments, the crystalline form can be characterized by an X-Ray Powder Diffraction (XRPD) spectrum having one or more (e.g., 1, 2, 3, 4, 5, 6, 7, 8, or 9) of the following peaks: 4.6, 6.9, 8.7, 17.5, 18.3, 18.6, 19.1, 19.6, and 20.8, degrees 2 theta, ±0.2°; a Differential Scanning Calorimetry (DSC) pattern having an endothermic peak with an onset temperature at about 69.0° C.; or a combination thereof. In some embodiments, the crystalline form can be characterized by an XRPD spectrum substantially the same as shown in FIG. 12A, for example, the XRPD spectrum shows peaks at the respective diffraction angels (degrees 2 theta, ±0.2°) corresponding to the peaks as shown in FIG. 12A, regardless of their relative intensities. In some embodiments, the crystalline form can be characterized by a DSC spectrum substantially the same as shown in FIG. 12B.

In some embodiments, the present disclosure also provides a method of preparing a crystalline form of abiraterone decanoate. In some embodiments, the method can include recrystallizing abiraterone decanoate in a suitable solvent, such as acetone and water. In a typical method, the abiraterone decanoate can be first dissolved in a first solvent, such as acetone, at room temperature or under heat (such as about 40° C.), to form a solution; the solution can then be cooled to form a suspension; and optionally, this can then be followed by dilution of the suspension with a second solvent (typically an antisolvent in which abiraterone decanoate has a low solubility), such as water, and stirring for a period of time (such as about 12 hours) to form the crystalline form. The amount of solvent, concentration, etc. can be adjusted by those skilled in the art in view of this disclosure. An exemplary procedure is also shown in Example 6A.

Abiraterone decanoate is typically prepared in a high purity form, e.g., suitable for pharmaceutical use. In some embodiments, the present disclosure provides abiraterone decanoate in a substantially pure form, such as having a purity of greater than 80%, preferably greater than 90% (e.g., greater than 95%, greater than 97%, greater than 98%, greater than 99%, greater than 99.5%), by weight, by IPLC area, or both. In some embodiments, the abiraterone decanoate can be characterized by a purity by weight and/or by IPLC area of about 95%, about 97%, about 99%, about 99.5%, about 99.9%, or any ranges between the specified values. For example, in some embodiments, the abiraterone decanoate can be characterized by a purity by weight of about 95%, about 97%, about 99%, about 99.5%, about 99.9%, or any ranges between the specified values. Exemplary procedures for preparing the substantially pure abiraterone decanoate are shown in the Examples section. HPLC methods suitable for measuring the purity of the abiraterone decanoate are also described in the Examples section. The substantially pure abiraterone decanoate can be in a solid form (e.g., a crystalline form described herein, amorphous form, or a combination thereof) or in a solution, suspension, or another form. For the avoidance of doubt, an abiraterone prodrug formulation comprising the substantially pure abiraterone decanoate herein and one or more other ingredients should be understood as a mixture of the substantially pure abiraterone decanoate herein and the one or more other ingredients, for example, such formulation can be obtained directly or indirectly from mixing (e.g., dissolving, suspending, or otherwise forming a mixture) the substantially pure abiraterone decanoate with the one or more other ingredients, such as pharmaceutically acceptable oil, solvent, etc.

In some specific embodiments, the present disclosure provides a pharmaceutical composition comprising abiraterone decanoate having the formula of:

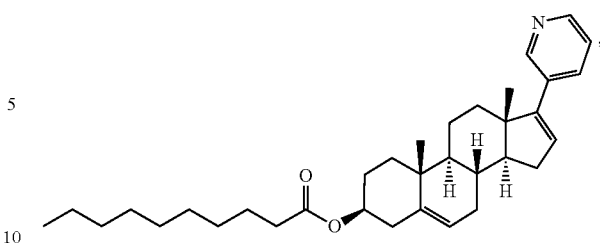

or a pharmaceutically acceptable salt thereof, and a pharmaceutically acceptable carrier. The abiraterone decanoate is typically present in the pharmaceutical composition in its basic form and should be understood as such unless otherwise obvious to the contrary from context. In some embodiments, the abiraterone decanoate can also be in a substantially pure form described herein. For example, the pharmaceutical composition can be prepared from mixing the substantially pure abiraterone decanoate with the pharmaceutically acceptable carrier and optional other ingredients. In some specific embodiments, the substantially pure abiraterone decanoate is in a crystalline form described herein, and the pharmaceutical composition can be prepared from mixing (e.g., dissolving, suspending, or otherwise forming a mixture) the crystalline form with the pharmaceutically acceptable carrier and optional other ingredients.

Typically, the pharmaceutical composition is formulated for parenteral administration. For example, in some embodiments, the pharmaceutical composition can be formulated for intramuscular injection, intradermal injection, or subcutaneous injection.

The pharmaceutical composition is generally a non-aqueous formulation, for example, an oil based formulation, and include a non-aqueous pharmaceutically acceptable carrier (e.g., described herein). For example, in some embodiments, the pharmaceutically acceptable carrier comprises a pharmaceutically acceptable oil, such as a pharmaceutically acceptable oil for injection, including oils of vegetable origin or synthetic mono- or diglycerides of fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. As understood by those skilled in the art, medium chain fatty acids typically include 6-12 carbons, such as caprioic acid, caprylic acid, capric acid, lauric acid, etc.; short chain fatty acids typically have fewer than 6 carbons; whereas long-chain fatty acids typically include 13-21 carbons. In some embodiments, the pharmaceutically acceptable carrier comprises a pharmaceutically acceptable oil, which can be selected from vegetable oil, castor oil, corn oil, sesame oil, cottonseed oil, peanut oil (arachis oil), poppy seed oil, tea seed oil, and soybean oil. In some specific embodiments, the pharmaceutically acceptable carrier can comprise corn oil, which includes a triglyceride, in which the fatty acid constituents are primarily linoleic acid, oleic acid, palmitic acid, and stearic acid.

In some embodiments, in addition to the pharmaceutically acceptable oil, the pharmaceutically acceptable carrier can further comprise a pharmaceutically acceptable solvent (or co-solvent if the oil is counted as a solvent), such as an alcohol, ester, acid, etc. In some embodiments, the pharmaceutically acceptable solvent can include benzyl alcohol, benzyl benzoate, ethanol, glycerol, polyethylene glycol, polysorbate 80, acetic acid, and/or ethyl acetate. In some embodiments, the pharmaceutically acceptable solvent can be benzyl alcohol and/or benzyl benzoate. In some embodiments, the pharmaceutically acceptable solvent can be benzyl alcohol. In some embodiments, the pharmaceutically acceptable solvent can be a combination of benzyl alcohol and benzyl benzoate. As discussed herein, the solubility of abiraterone decanoate in a pharmaceutically acceptable oil can be significantly enhanced by a combination of benzyl alcohol and benzyl benzoate.

In some specific embodiments, the present disclosure provides a pharmaceutical composition comprising abiraterone decanoate, a pharmaceutically acceptable oil (e.g., described herein), benzyl alcohol, and benzyl benzoate. In some embodiments, the pharmaceutically acceptable oil is corn oil. In some embodiments, the benzyl alcohol is present in an amount of about 5-10% by volume, the benzyl benzoate is present in an amount of about 10-20% by volume, and corn oil is present in an amount of about 70-85% by volume, with the combined volume of benzyl alcohol, benzyl benzoate, and corn oil being 100%.

The pharmaceutical composition typically include abiraterone decanoate at a concentration of about 25 mg/ml to about 500 mg/ml. In some embodiments, the abiraterone decanoate can be present in a concentration of about 50 mg/ml, about 100 mg/ml, about 150 mg/ml, about 200 mg/ml, about 250 mg/ml, about 300 mg/ml, about 350 mg/ml, about 400 mg/ml, about 500 mg/ml, or any ranges between the recited values. In some embodiments, the abiraterone decanoate can be present in a concentration of about 100 mg/ml to about 300 mg/ml, such as about 150 mg/ml to about 250 mg/ml, about 200 mg/ml to about 300 mg/ml, etc.

The abiraterone decanoate in the pharmaceutical composition is typically included in a therapeutically effective amount for treating a disease or disorder described herein, such as prostate cancer. In some embodiments, the abiraterone decanoate can be present in the pharmaceutical composition in an amount sufficient to provide a therapeutically effective blood plasma concentration of abiraterone for a period of at least one week, e.g., at least two weeks, at least four weeks, and up to six or eight weeks or more, after a single administration to a subject having a sex hormone-dependent benign or malignant disorder, a syndrome due to androgen excess, and/or a syndrome due to glucocorticoid excess such as hypercortisolemia. In some embodiments, the abiraterone decanoate can be present in the pharmaceutical composition in an amount sufficient to provide a therapeutically effective blood plasma concentration of abiraterone at about 1 ng/ml or higher, such as about 2 ng/ml or higher, about 4 ng/ml or higher, about 5 ng/ml or higher, about 8 ng/ml or higher, etc. for a period of at least one week, e.g., at least two weeks, at least four weeks, and up to six or eight weeks or more, after a single administration to a subject having a sex hormone-dependent benign or malignant disorder, a syndrome due to androgen excess, and/or a syndrome due to glucocorticoid excess such as hypercortisolemia. In some embodiments, the abiraterone decanoate can be present in the pharmaceutical composition in an amount sufficient to provide a therapeutically effective blood plasma concentration of abiraterone at about 0.5 ng/ml or higher for a period of at least four weeks, e.g., at least six weeks and up to eight weeks or more, after a single administration to a subject having a sex hormone-dependent benign or malignant disorder, a syndrome due to androgen excess, and/or a syndrome due to glucocorticoid excess such as hypercortisolemia.

In some specific embodiments, the present disclosure provides a pharmaceutical composition, e.g., unit dosage form, comprising a therapeutically effective amount of abiraterone decanoate having the formula of:

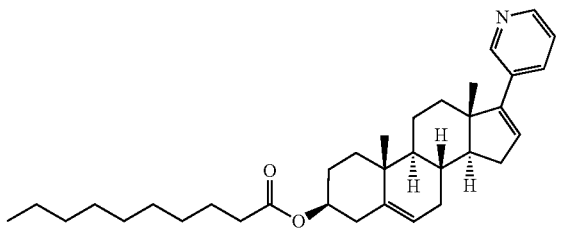

a pharmaceutically acceptable oil, and a pharmaceutically acceptable solvent, wherein the abiraterone decanoate is in its basic form, which is present at a concentration of about 25 mg/ml to about 500 mg/ml, such as about 50 mg/ml, about 100 mg/ml, about 150 mg/ml, about 200 mg/ml, about 250 mg/ml, about 300 mg/ml, about 350 mg/ml, about 400 mg/ml, about 500 mg/ml, or any ranges between the recited values, wherein the pharmaceutical composition, e.g., unit dosage form, is formulated for parenteral injection, such as intramuscular injection, intradermal injection, or subcutaneous injection, wherein the pharmaceutical composition, e.g., unit dosage form, comprises the abiraterone decanoate in an amount of about 50 mg to about 2,000 mg, such as about 100 mg, about 350 mg, about 500 mg, about 1000 mg, about 1500 mg, about 2000 mg, or any ranges between the recited values. In some embodiments, the pharmaceutical composition can be in a unit dosage form. Typically, depending on the dosing amount, one or more (e.g., 1) of the unit dosage forms can be administered to a subject in need thereof. The pharmaceutically acceptable oil in the pharmaceutical composition, e.g., unit dosage form, can be any of those described herein. For example, in some embodiments, the pharmaceutically acceptable oil is a pharmaceutically acceptable oil for injection, including oils of vegetable origin or synthetic mono- or diglycerides of fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable oil can comprise a triglyceride derived from fatty acids. In some embodiments, the pharmaceutically acceptable oil can comprise a triglyceride derived from long and/or medium chain fatty acids, which can be independently poly-unsaturated, mono-unsaturated, or saturated. In some embodiments, the pharmaceutically acceptable oil can be selected from vegetable oil, castor oil, corn oil, sesame oil, cottonseed oil, peanut oil (arachis oil), poppy seed oil, tea seed oil, and soybean oil. In some specific embodiments, the pharmaceutically acceptable oil can comprise corn oil, which includes a triglyceride, in which the fatty acid constituents are primarily linoleic acid, oleic acid, palmitic acid, and stearic acid. The pharmaceutically acceptable solvent in the pharmaceutical composition, e.g., unit dosage form, also include any of those described herein. In some embodiments, the pharmaceutically acceptable solvent (or co-solvent if the oil is counted as a solvent), such as an alcohol, ester, acid, etc. In some embodiments, the pharmaceutically acceptable solvent can include benzyl alcohol, benzyl benzoate, ethanol, glycerol, polyethylene glycol, polysorbate 80, acetic acid, and/or ethyl acetate. In some embodiments, the pharmaceutically acceptable solvent can be benzyl alcohol and/or benzyl benzoate. In some embodiments, the pharmaceutical composition, e.g., unit dosage form, comprises abiraterone decanoate, a pharmaceutically acceptable oil (e.g., described herein), benzyl alcohol, and benzyl benzoate. In some embodiments, the pharmaceutically acceptable oil is corn oil. In some embodiments, the benzyl alcohol is present in an amount of about 5-10% by volume, the benzyl benzoate is present in an amount of about 10-20% by volume, and corn oil is present in an amount of about 70-85% by volume, with the combined volume of benzyl alcohol, benzyl benzoate, and corn oil being 100%.

In some embodiments, the present disclosure provides exemplary abiraterone decanoate formulations as shown in Table C. All numeric values in the table should be understood as preceded by the term "about." The concentration of abiraterone decanoate refers to the amount of abiraterone decanoate in mg per ml of the final formulation, which can be a solution or suspension. The amount of oil (the primary solvent) and co-solvent (benzyl alcohol and/or benzyl benzoate) in the tables is expressed as volume percentage of solvent, which includes both the oil and co-solvent. Suitable oil include any of the pharmaceutically acceptable oil as described herein, such as corn oil. Optional additional ingredients are not shown in Table C. Examples 3F-3H herein show procedures of preparing representative abiraterone decanoate formulations of Table C.

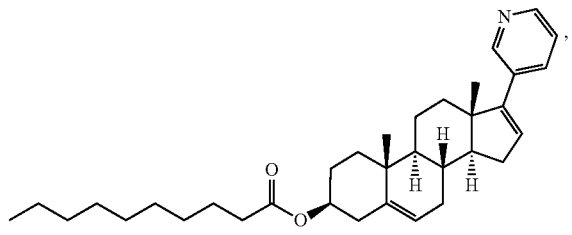

in a pharmaceutically acceptable carrier to form a mixture (such as a solution or suspension). In some embodiments, the method further comprises sterilizing the mixture (e.g., solution or suspension). In some embodiments, the dissolving or suspending can comprise mixing (e.g., dissolving or suspending) the crystalline form of abiraterone decanoate described herein in the pharmaceutically acceptable carrier. In some embodiments, the mixing (such as dissolving or suspending) can comprise mixing (e.g., dissolving or suspending) the substantially pure abiraterone decanoate described herein in the pharmaceutically acceptable carrier. Suitable pharmaceutically acceptable carriers and amounts, amount of abiraterone decanoate, concentration of abiraterone decanoate, include any of those described herein. For example, in some embodiments, the pharmaceutically acceptable carrier comprises a pharmaceutically acceptable oil and a pharmaceutically acceptable solvent, wherein the pharmaceutically acceptable oil comprises a vegetable oil, castor oil, corn oil, sesame oil, cottonseed oil, peanut oil,

TABLE C

Exemplary Abiraterone Decanoate Formulations

| Ingredients | Amount/Concentration | | |
|---|---|---|---|
| | Typical | Exemplary range | More Exemplary Range |
| Abiraterone decanoate | 25 mg/ml to 500 mg/ml | 50 mg/ml to 300 mg/ml; 100 mg/ml to 300 mg/ml | 75 mg/ml to 300 mg/ml, such as 150 mg/ml to about 250 mg/ml |
| Oil (e.g., corn oil, castor oil, sesame oil, peanut oil, cottonseed oil, and/or Miglyol 812) | 30% to 100% of solvent | 50% to 90% of solvent | 60% to 90% of solvent, such as 70% |
| benzyl alcohol | 0% to 20% of solvent | 0% to 15% of solvent | 0% to 10% of solvent, such as 10% |
| benzyl benzoate | 0% to 50% of solvent | 0% to 35% of solvent | 0% to 30% of solvent, such as 20% |

The pharmaceutical composition or unit dosage form herein can be prepared by those skilled in the art in view of the methods disclosed herein. In some embodiments, the present disclosure provides a method for preparing an abiraterone decanoate formulation suitable for parenteral administration to a subject having a sex hormone-dependent benign or malignant disorder, a syndrome due to androgen excess, and/or a syndrome due to glucocorticoid excess such as hypercortisolemia. In some embodiments, the method comprises mixing (such as dissolving or suspending) abiraterone decanoate, which has the formula of:

poppy seed oil, tea seed oil, or soybean oil, the pharmaceutically acceptable solvent comprises benzyl alcohol and/or benzyl benzoate, and wherein the abiraterone decanoate is present at a concentration of about 50 mg/mL to about 300 mg/mL such as about 100 mg/mL to about 300 mg/mL.

In some specific embodiments, the present disclosure also provides a method of treating a sex hormone-dependent benign or malignant disorder, a syndrome due to androgen excess, and/or a syndrome due to glucocorticoid excess such as hypercortisolemia, comprising administering to a subject in need thereof a therapeutically effective amount of the pharmaceutical composition comprising abiraterone decanoate described herein (e.g., the unit dosage form described herein). The administering is not limited to any particular route. However, the abiraterone decanoate is typically administered parenterally, for example, via an intramuscular injection, intradermal injection, or subcutaneous injection. In some embodiments, the administering is through intramuscular injection. Unlike oral administration of abiraterone acetate, the pharmaceutical composition comprising abiraterone decanoate described herein (e.g., the unit dosage form described herein) can be administered to the subject in need with or without food.

Sex hormone-dependent benign or malignant disorder that can be treated with the methods include any of those described herein. In some embodiments, the sex hormone-dependent benign or malignant disorders can be selected from androgen-dependent disorders and estrogen-dependent disorders such as androgen-dependent or estrogen-dependent cancers. In some embodiments, the sex hormone-dependent benign or malignant disorders can be selected from prostate cancer, breast cancer, ovarian cancer, bladder cancer, hepatocellular carcinoma, and lung cancer, etc. In some embodiments, the sex hormone-dependent benign or malignant disorder can be prostate cancer or breast cancer. In some embodiments, the sex hormone-dependent benign or malignant disorder is castration resistant prostate cancer or castration sensitive prostate cancer. In some embodiments, the sex hormone-dependent benign or malignant disorder can be metastatic castration resistant prostate cancer or metastatic castration sensitive prostate cancer. Syndromes due to androgen excess and/or syndromes due to glucocorticoid excess such as hypercortisolemia that can be treated with the methods include any of those described herein. In some embodiments, the method herein can be a method for treating a non-oncologic syndrome in the subject due to androgen excess, such as endometriosis, polycystic ovary syndrome, congenital adrenal hyperplasia (e.g., classical or nonclassical congenital adrenal hyperplasia), precocious puberty, hirsutism, etc. In some embodiments, the method herein can be a method for treating a non-oncologic syndrome due to glucocorticoid (e.g., cortisole) excess, such as Cushing's syndrome or Cushing's disease.

The methods herein can be used in conjunction with one or more additional therapies for the respective disease or disorder. For example, the method can comprise administering one or more other drug or agent (for example, as described herein, such as another cancer chemotherapeutic drug, hormone replacement drug, or hormone ablation drug) to the subject, either concurrently or sequentially, through the same route or a different route of administration. In some embodiments, the subject can also be treated with a gonadotropin-releasing hormone analog and/or bilateral orchiectomy.

As discussed herein, abiraterone is a 17α-hydroxylase/C17,20-lyase (CYP17) inhibitor, which can lead to reduction in biosynthesis of androgens (such as testosterone), reduction in glucocorticoids (such as cortisol), and an mineralocorticoid excess (e.g., increase in progesterone). Adrenal insufficiency has also been noted to be associated with abiraterone therapy, such as Zytiga®. Intramuscular administration of a pharmaceutical composition comprising abiraterone decanoate herein was shown to provide an effective plasma level of abiraterone and inhibit CYP17A1 in vivo for a prolonged period of time, with an increase in progesterone level and a reduction in cortisol level.

In some embodiments, the method herein (e.g., treating a prostate cancer, or treating classical or nonclassical congenital adrenal hyperplasia) can comprise administering to the subject an agent that offsets the reduction of glucocorticoid(s) associated with the administration of abiraterone decanoate as described herein. In some embodiments, the method can comprise administering to the subject in need an agent effective in treating one or more symptoms associated with adrenal insufficiency, such as acute stress, fatigue, etc. In some specific embodiments, the method can comprise administering to the subject a steroid, such as a corticosteroid. In some embodiments, the method can comprise administering to the subject a glucocorticoid. In some specific embodiments, the method also comprises administering to the subject prednisone, prednisolone, and/or methylprednisolone. In some embodiments, the method also comprises administering to the subject an agent effective in treating cortisol deficiency, for example, hydrocortisone, prednisone, prednisolone, methylprednisolone, and/or dexamethasone. In any such embodiments, the agent can be administered to the subject either concurrently or sequentially in any order, via a same or different route of administration.

In some embodiments, the methods herein can be characterized by a dosing frequency of once a week or even less frequent. Typically, the dosing frequency can range from once a week to once every few months, such as from once a week to once every three months, or from once a week to once every eight weeks, such as once a month. In some embodiments, the method comprises administering to the subject the pharmaceutical composition comprising abiraterone decanoate (e.g., the unit dosage form described herein) once a week, once in two weeks, once in three weeks, once a month, or once in more than a month. In some embodiments, the method comprises administering to the subject the pharmaceutical composition comprising abiraterone decanoate (e.g., the unit dosage form described herein) once in two weeks, once a month, or once in more than a month. In some embodiments, the dosing amount for each dose is about 50 mg to about 2000 mg (e.g., about 100 mg, about 350 mg, about 500 mg, about 1000 mg, about 1500 mg, or any ranges between the recited values) of abiraterone decanoate. In some embodiments, the dosing amount of abiraterone decanoate for each dose is about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of a subject. In some embodiments, the administering is via intramuscular injection. In some embodiments, the administering provides a therapeutically effective blood plasma concentration of abiraterone a period of at least one week, e.g., at least two weeks, such as at least three weeks, at least four weeks, and up to six or eight weeks or more, etc. In some embodiments, the administering provides a blood plasma concentration of abiraterone above 1.0 ng/ml (e.g., between about 1 ng/ml and about 8 ng/ml, or about 2 ng/ml or higher, about 4 ng/ml or higher, about 5 ng/ml or higher, or about 8 ng/ml or higher) for a period of at least one week, e.g., at least two weeks, such as at least 3 weeks, at least four weeks, and up to six or eight weeks or more, etc. In some embodiments, the administering provides a steady state $C_{min}$ of abiraterone above 1.0 ng/ml (e.g., between about 1 ng/ml and about 8 ng/ml, about 2 ng/ml or higher, about 4 ng/ml or higher, about 5 ng/ml or higher, or about 8 ng/ml or higher). In some embodiments, the administering provides a single dose or steady state $C_{max}$ of abiraterone between about 10 ng/ml and about 400 ng/ml, such as about 10 ng/ml, about 15 ng/ml, about 20 ng/ml, about 30 ng/ml, about 50 ng/ml, about 60 ng/ml, about 100 ng/ml, about 150 ng/ml, about 160 ng/ml, or any ranges recited between the values, for example, about 10-30 ng/ml, about 20-60 ng/ml, about 15-160 ng/ml or about 50-100 ng/ml. In some embodiments, the abiraterone decanoate formulation can be administered to the subject in need thereof as the only source of abiraterone. However, in some embodiments, the abiraterone decanoate formulation can also be administered to the subject in need thereof as a supplement to another abiraterone therapy.

In some specific example, the present disclosure provides a method of treating prostate cancer, the method comprising administering to a subject in need thereof abiraterone decanoate via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate. In some embodiments, the abiraterone decanoate is administered via intramuscular injection. In some embodiments, the prostate cancer is castration resistant prostate cancer or castration sensitive prostate cancer. In some embodiments, the prostate cancer is metastatic castration resistant prostate cancer or metastatic castration sensitive prostate cancer.

In some specific example, the present disclosure provides a method of treating prostate cancer, the method comprising administering to a subject in need thereof the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the prostate cancer is castration resistant prostate cancer or castration sensitive prostate cancer. In some embodiments, the prostate cancer is metastatic castration resistant prostate cancer or metastatic castration sensitive prostate cancer.

In some specific example, the present disclosure provides a method of treating prostate cancer, the method comprising administering to a subject in need thereof the unit dosage form described herein via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the unit dosage form is administered via intramuscular injection. In some embodiments, the prostate cancer is castration resistant prostate cancer or castration sensitive prostate cancer. In some embodiments, the prostate cancer is metastatic castration resistant prostate cancer or metastatic castration sensitive prostate cancer.

In some specific embodiments, the present disclosure also provides a method of delivering abiraterone to a subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a hormone-dependent benign or malignant disorder, a syndrome due to androgen excess, and/or a syndrome due to glucocorticoid excess such as hypercortisolemia, e.g., as described herein.

In some specific embodiments, the present disclosure also provides a method of inhibiting CYP17A1 activity in a subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a sex hormone-dependent benign or malignant disorder, e.g., as described herein. In some embodiments, the subject suffers from a syndrome due to androgen excess and/or a syndrome due to glucocorticoid excess such as hypercortisolemia, e.g., as described herein.

In some specific embodiments, the present disclosure also provides a method of reducing the level of glucocorticoids (e.g., cortisol) in a subject in need thereof in a subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a hypercortisolemia as described herein, such as Cushing's syndrome or Cushing's disease.

In some specific embodiments, the present disclosure also provides a method of reducing the level of androgens (e.g., testosterone and/or dihydrotestosterone) and/or estrogens in a subject in need thereof in a subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone decanoate or with each dose of abiraterone decanoate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a syndrome due to androgen excess, such as congenital adrenal hyperplasia (e.g., classical or nonclassical congenital adrenal hyperplasia), endometriosis, polycystic ovary syndrome precocious puberty, hirsutism, etc. In some embodiments, the subject suffers from an androgen and/or estrogen associated cancer, such as prostate cancer or breast cancer.

Other Abiraterone Prodrugs

While the present disclosure describes embodiments relating to abiraterone decanoate in more details, those skilled in the art would understand similar embodiments are also applicable to other abiraterone prodrugs of the present disclosure in view of the descriptions herein. For example, like abiraterone decanoate, pharmacokinetics studies show that intramuscular injection of abiraterone isocaproate formulations can also provide a therapeutically effective amount of plasma abiraterone for an extended period of time. Thus, embodiments described herein specifically to abiraterone decanoate formulations and methods of treatment can also be similarly applicable to abiraterone isocaproate, with abiraterone decanoate replaced with abiraterone isocaproate.

For example, in some embodiments, the present disclosure also provides a method of treating a sex hormone-dependent benign or malignant disorder, a syndrome due to androgen excess, and/or a syndrome due to glucocorticoid excess such as hypercortisolemia, comprising administering to a subject in need thereof a therapeutically effective amount of the pharmaceutical composition comprising abiraterone isocaproate described herein (e.g., the unit dosage form described herein). In some embodiments, the pharmaceutical composition comprising abiraterone isocaproate described herein (e.g., the unit dosage form described herein) can be administered to the subject in need with or without food. Suitable sex hormone-dependent benign or malignant disorders, syndromes due to androgen excess, syndromes due to glucocorticoid excess such as hypercortisolemia, dosing regimen, combination therapies, etc. include those described herein, e.g., in connection with abiraterone decanoate.

In some specific example, the present disclosure provides a method of treating prostate cancer, the method comprising administering to a subject in need thereof the pharmaceutical composition comprising abiraterone isocaproate described herein via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the prostate cancer is castration resistant prostate cancer or castration sensitive prostate cancer. In some embodiments, the prostate cancer is metastatic castration resistant prostate cancer or metastatic castration sensitive prostate cancer.

In some specific example, the present disclosure provides a method of treating prostate cancer, the method comprising administering to a subject in need thereof the unit dosage form comprising abiraterone isocaproate described herein via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the unit dosage form is administered via intramuscular injection. In some embodiments, the prostate cancer is castration resistant prostate cancer or castration sensitive prostate cancer. In some embodiments, the prostate cancer is metastatic castration resistant prostate cancer or metastatic castration sensitive prostate cancer.

In some specific embodiments, the present disclosure also provides a method of delivering abiraterone to a subject in need thereof, the method comprising administering to the subject the pharmaceutical composition comprising abiraterone isocaproate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a hormone-dependent benign or malignant disorder, a syndrome due to androgen excess, and/or a syndrome due to glucocorticoid excess such as hypercortisolemia, e.g., as described herein.

In some specific embodiments, the present disclosure also provides a method of inhibiting CYP17A1 activity in a subject in need thereof, the method comprising administering to the subject the pharmaceutical composition comprising abiraterone isocaproate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a sex hormone-dependent benign or malignant disorder, e.g., as described herein. In some embodiments, the subject suffers from syndromes due to androgen excess and/or syndromes due to glucocorticoid excess such as hypercortisolemia, e.g., as described herein.

In some specific embodiments, the present disclosure also provides a method of reducing the level of glucocorticoids (e.g., cortisol) in a subject in need thereof in a subject in need thereof, the method comprising administering to the subject the pharmaceutical composition comprising abiraterone isocaproate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a hypercortisolemia as described herein, such as Cushing's syndrome or Cushing's disease.

In some specific embodiments, the present disclosure also provides a method of reducing the level of androgens (e.g., testosterone and/or dihydrotestosterone) and/or estrogens in a subject in need thereof in a subject in need thereof, the method comprising administering to the subject the pharmaceutical composition comprising abiraterone isocaproate described herein (e.g., the unit dosage form described herein) via intramuscular injection, intradermal injection, or subcutaneous injection, once a week or once in more than a week, such as once a month or once in more than a month, with each dose at about 50 mg to about 2000 mg (e.g., about 100 mg, about 350 mg, about 500 mg, about 1000 mg, about 1500 mg, or any ranges between the recited values) of abiraterone isocaproate or with each dose of abiraterone isocaproate at about 0.5 mg/kg to about 100 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, or any ranges between the recited values) of body weight of the subject. In some embodiments, the pharmaceutical composition is administered via intramuscular injection. In some embodiments, the subject suffers from a syndrome due to androgen excess, such as congenital adrenal hyperplasia (e.g., classical or nonclassical congenital adrenal hyperplasia), endometriosis, polycystic ovary syndrome precocious puberty, hirsutism, etc. In some embodiments, the subject suffers from an androgen and/or estrogen associated cancer, such as prostate cancer or breast cancer.

Non-Limiting Exemplary Embodiments

In some embodiments, the present disclosure also provides non-limiting exemplary Embodiments 1-66 as shown below:

Embodiment 1. An abiraterone prodrug formulation suitable for parenteral administration to a subject having a hormone-dependent benign or malignant disorder, comprising:
(a) one or more lipophilic-ester forms of abiraterone, and
(b) one or more pharmaceutically acceptable carriers, diluents, or excipients,
wherein upon said administration to said subject, said abiraterone prodrug formulation achieves a therapeutic blood plasma concentration of abiraterone.

Embodiment 2. The abiraterone prodrug formulation of Embodiment 1, wherein said therapeutic blood plasma concentration of abiraterone is at least 1.0 ng/ml.

Embodiment 3. The abiraterone prodrug formulation of Embodiment 1, wherein said therapeutic blood plasma concentration of abiraterone is at least 8 ng/ml.

Embodiment 4. The abiraterone prodrug formulation of Embodiment 1, wherein said therapeutic blood plasma concentration of abiraterone persists for at least two weeks.

Embodiment 5. The abiraterone prodrug formulation of Embodiment 1, wherein said parenteral administration is selected from the group consisting of intramuscular injection, intradermal injection, and subcutaneous injection.

Embodiment 6. The abiraterone prodrug formulation of Embodiment 1, wherein said lipophilic-ester form is selected from the group consisting of acetate, propionate, butanoate, valerate, caproate, enanthate, cypionate, isocaproate, buciclate, cyclohexanecarboxylate, phenyl propionate, decanoate and undecanoate.

Embodiment 7. The abiraterone prodrug formulation of Embodiment 1, wherein said hormone-dependent benign or malignant disorder is selected from the group consisting of androgen-dependent disorders and estrogen-dependent disorders.

Embodiment 8. The abiraterone prodrug formulation of Embodiment 1, wherein said hormone-dependent benign or malignant disorder is selected from the group consisting of prostate cancer and breast cancer.

Embodiment 9. The abiraterone prodrug formulation of Embodiment 8, wherein said prostate cancer is selected from the group consisting of castration resistant prostate cancer and castration sensitive prostate cancer.

Embodiment 10. A method for treating a hormone-dependent benign or malignant disorder comprising parenterally administering to a subject in need of such treatment an effective dose of at least one abiraterone prodrug formulation comprising:

(a) one or more lipophilic-ester forms of abiraterone, and
(b) one or more pharmaceutically acceptable carriers, diluents, or excipients, wherein upon said administration, said at least one abiraterone prodrug formulation achieves a therapeutic blood plasma concentration of abiraterone.

Embodiment 11. The method of Embodiment 10, wherein said therapeutic blood plasma concentration of abiraterone is at least 1.0 ng/ml.

Embodiment 12. The method of Embodiment 10, wherein said therapeutic blood plasma concentration of abiraterone is at least 8.0 ng/ml.

Embodiment 13. The method of Embodiment 10, wherein said therapeutic blood plasma concentration of abiraterone persists for at least two weeks.

Embodiment 14. The method of Embodiment 10, wherein said parenteral administration is selected from the group consisting of intramuscular injection, intradermal injection, and subcutaneous injection.

Embodiment 15. The method of Embodiment 10, wherein said lipophilic-ester form is selected from the group consisting of acetate, propionate, butanoate, valerate, caproate, enanthate, cypionate, isocaproate, buciclate, cyclohexanecarboxylate, phenyl propionate, decanoate and undecanoate.

Embodiment 16. The method of Embodiment 10, wherein said hormone-dependent benign or malignant disorder is selected from the group consisting of androgen-dependent disorders and estrogen-dependent disorders.

Embodiment 17. The method of Embodiment 10, wherein said hormone-dependent benign or malignant disorder is selected from the group consisting of prostate cancer and breast cancer.

Embodiment 18. The method of Embodiment 17, wherein said prostate cancer is selected from the group consisting of castration resistant prostate cancer and castration sensitive prostate cancer.

Embodiment 19. The method of Embodiment 10, wherein the method further comprises once-monthly administration of said at least one abiraterone prodrug formulation.

Embodiment 20. The method of Embodiment 10, wherein said at least one abiraterone prodrug formulation is administered in a divided dose.

Embodiment 21. The method of Embodiment 10, wherein said at least one abiraterone prodrug formulation is administered simultaneously with at least one other drug or agent.

Embodiment 22. The method of Embodiment 10, wherein said at least one abiraterone prodrug formulation is administered before at least one other drug or agent.

Embodiment 23. The method of Embodiment 10, wherein said at least one abiraterone prodrug formulation is administered after at least one other drug or agent.

Embodiment 24. A kit for treating the hormone-dependent benign or malignant disorder of Embodiment 10, comprising at least one abiraterone prodrug formulation.

Embodiment 25. A method for preparing an abiraterone decanoate formulation suitable for parenteral administration to a subject having a hormone-dependent benign or malignant disorder, comprising the steps of:
(a) preparing and purifying abiraterone decanoate,
(b) preparing an oil and co-solvent mixture,
(c) combining said prepared and purified abiraterone decanoate with one of said oil and alcohol mixture from step (b),
(d) sterilizing the mixture formed in step (c), and
(e) optionally combining the sterilized mixture of step (d) with one or more pharmaceutically acceptable carriers, diluents, or excipients.

Embodiment 26. The method of Embodiment 25, wherein said prepared and purified abiraterone decanoate has the following chemical properties: LCMS m/z 504.4 (M+H); $^1$H NMR (CDCl$_3$, 200 MHz): δH 0.877 (3H, t, J=7 Hz), 1.043 (3H, s), 1.082 (3H, s), 1.268 (16H, m), 1.643 (15H, m), 1.842 (3H, m), 2.065 (3H, m), 2.290 (5H, m), 4.602 (1H, m), 5.404 (1H, d, J=5 Hz), 5.998 (1H, q, J=5 Hz), 7.215 (1H, ddd, J=1, 5.8 Hz), 7.643 (1H, dt, J=2.8 Hz), 8.455 (1H, dd, J=2.5 Hz), 8.617 (1H, dd, J=1.2 Hz).

Embodiment 27. The method of Embodiment 25, wherein said oil and co-solvent mixture is selected from the group consisting of 90% castor oil/10% benzyl alcohol and 90% corn oil/10% benzyl alcohol.

Embodiment 28. A compound of Formula I, or a pharmaceutically acceptable salt thereof,

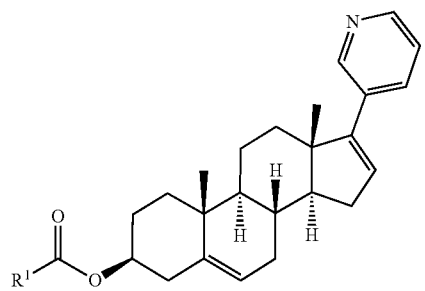

Formula I wherein $R^1$ is $R^{10}$, O—$R^{10}$, or NHR$^{10}$,
wherein $R^{10}$ is selected from:
a $C_{7-30}$ alkyl; a $C_{7-30}$ alkenyl; a $C_{7-30}$ alkynyl; an alkyl substituted with a cycloalkyl, which has a total number of carbons between 5 and 16; an alkyl substituted with a phenyl, which has a total number of carbons between 7 and 16; a cycloalkyl optionally substituted with one or more alkyl, which has a total number of carbons between 5 and 16; and

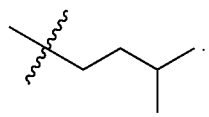 [SMILES: *CCC(C)C]

Embodiment 29. The compound of Embodiment 28, or a pharmaceutically acceptable salt thereof, wherein $R^{10}$ is a $C_{7-16}$ alkyl.

Embodiment 30. The compound of Embodiment 28, or a pharmaceutically acceptable salt thereof, wherein $R^{10}$ is an alkyl substituted with a $C_{3-6}$ cycloalkyl, which has a total number of carbons between 6 and 12.

Embodiment 31. The compound of Embodiment 28, or a pharmaceutically acceptable salt thereof, wherein $R^1$ is a $C_{7-16}$ alkyl.

Embodiment 32. The compound of Embodiment 28, or a pharmaceutically acceptable salt thereof, wherein $R^1$ is an alkyl having the formula —(CH$_2$)$_n$—CH$_3$, wherein n is an integer between 6 and 12, such as 6, 7, 8, 9, 10, 11, or 12.

Embodiment 33. The compound of Embodiment 28, or a pharmaceutically acceptable salt thereof, wherein $R^1$ is represented by the formula —$(CH_2)_n$-Cy, wherein n is an integer of 1-6, and Cy is a $C_{3-6}$ cycloalkyl or phenyl.

Embodiment 34. The compound of Embodiment 33, or a pharmaceutically acceptable salt thereof, wherein n is 1 or 2 and Cy is cyclopentyl, cyclohexyl, or phenyl.

Embodiment 35. The compound of Embodiment 28, or a pharmaceutically acceptable salt thereof, wherein $R^1$ is

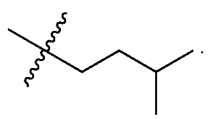 [SMILES: *CCC(C)C]

Embodiment 36. The compound of Embodiment 28, or a pharmaceutically acceptable salt thereof, wherein $R^1$ is

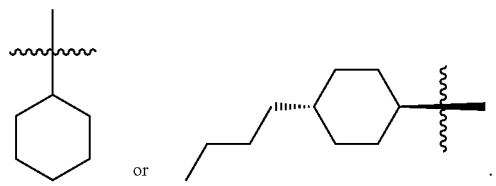

Embodiment 37. A pharmaceutical composition comprising the compound of any one of Embodiments 28-36, or a pharmaceutically acceptable salt thereof.

Embodiment 38. The pharmaceutical composition of Embodiment 37, formulated for parenteral administration.

Embodiment 39. The pharmaceutical composition of Embodiment 38, formulated for intramuscular injection, intradermal injection, or subcutaneous injection.

Embodiment 40. The pharmaceutical composition of Embodiment 37, further comprising a pharmaceutically acceptable carrier.

Embodiment 41. The pharmaceutical composition of Embodiment 40, wherein the pharmaceutically acceptable carrier comprises a pharmaceutically acceptable oil, e.g., an oil suitable for use as vehicles for injection, such as an oil of vegetable origin or synthetic mono- or di-glycerides of fatty acids, e.g., a vegetable oil, castor oil, corn oil, sesame oil, cottonseed oil, peanut oil, poppy seed oil, tea seed oil, or soybean oil.

Embodiment 42. The pharmaceutical composition of Embodiment 40 or 41, further comprising a pharmaceutically acceptable solvent, e.g., benzyl alcohol.

Embodiment 43. The pharmaceutical composition of any one of Embodiments 37-42, which is a non-aqueous solution or suspension.

Embodiment 44. A pharmaceutical composition comprising a compound of Formula II, or a pharmaceutically acceptable salt thereof,

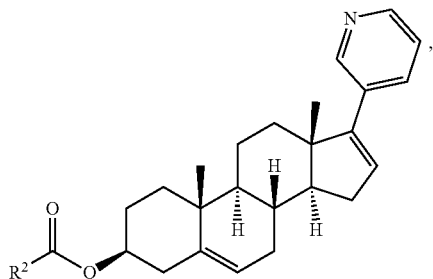

Formula II wherein $R^2$ is $R^{20}$, $OR^{20}$, or $NHR^{20}$,
wherein $R^{20}$ is selected from:
a $C_{1-30}$ alkyl; a $C_{2-30}$ alkenyl; a $C_{2-30}$ alkynyl; an alkyl substituted with a cycloalkyl, which has a total number of carbons between 4 and 30; an alkyl substituted with a phenyl, which has a total number of carbons between 7 and 30; and a cycloalkyl optionally substituted with one or more alkyl, which has a total number of carbons between 3 and 30,
wherein the pharmaceutical composition is formulated for intramuscular injection, intradermal injection, or subcutaneous injection, and the compound of Formula II or pharmaceutically acceptable salt thereof is present in the pharmaceutical composition at a concentration of about 25 mg/ml to about 500 mg/ml.

Embodiment 45. The pharmaceutical composition of Embodiment 44, wherein $R^2$ in Formula II is selected from a $C_{1-16}$ alkyl; an alkyl substituted with a cycloalkyl, which has a total number of carbons between 5 and 16; an alkyl substituted with a phenyl, which has a total number of carbons between 7 and 16; and a cycloalkyl optionally substituted with one or more alkyl, which has a total number of carbons between 5 and 16.

Embodiment 46. The pharmaceutical composition of Embodiment 44, wherein $R^2$ in Formula II is an alkyl having the formula —$(CH_2)_n$—$CH_3$, wherein n is an integer between 0 and 12.

Embodiment 47. The pharmaceutical composition of Embodiment 44, wherein $R^2$ in Formula II is represented by the formula —$(CH_2)_n$-Cy, wherein n is an integer of 1-6, and Cy is a $C_{3-6}$ cycloalkyl or phenyl.

Embodiment 48. The pharmaceutical composition of Embodiment 44, wherein $R^2$ in Formula II is

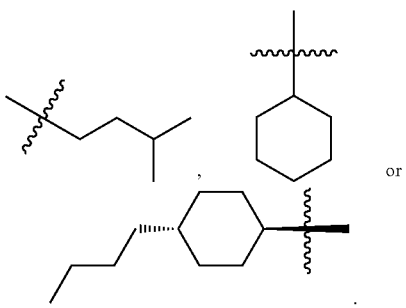

Embodiment 49. The pharmaceutical composition of any one of Embodiments 44-48, which is a non-aqueous solution or suspension.

Embodiment 50. The pharmaceutical composition of any one of Embodiments 44-49, wherein the compound of Formula II or pharmaceutically acceptable salt thereof is dissolved or suspended in a pharmaceutically acceptable oil, e.g., an oil suitable for use as vehicles for injection, such as an oil of vegetable origin or synthetic mono- or di-glycerides of fatty acids, e.g., a vegetable oil, castor oil, corn oil, sesame oil, cottonseed oil, peanut oil, poppy seed oil, tea seed oil, or soybean oil.

Embodiment 51. The pharmaceutical composition of any one of Embodiments 44-50, further comprising a pharmaceutically acceptable solvent, e.g., benzyl alcohol.

Embodiment 52. The pharmaceutical composition of any one of Embodiments 44-51, which comprises the compound of Formula II or pharmaceutically acceptable salt thereof in an amount sufficient to provide a therapeutically effective blood plasma concentration of abiraterone for a period of at least two weeks, after a single administration to a subject having a hormone-dependent benign or malignant disorder (e.g., metastatic castration resistant prostate cancer or metastatic castration sensitive prostate cancer).

Embodiment 53. The pharmaceutical composition of Embodiment 52, wherein the therapeutically effective blood plasma concentration of abiraterone is about 1 ng/ml or higher.

Embodiment 54. The pharmaceutical composition of Embodiment 53, wherein the therapeutically effective blood plasma concentration of abiraterone is about 8 ng/ml or higher.

Embodiment 55. A method of treating a hormone-dependent benign or malignant disorder comprising administering to a subject in need thereof a therapeutically effective amount of the compound of any one of Embodiments 28-36 or a pharmaceutically acceptable salt thereof, or the pharmaceutical composition of any one of Embodiments 37-54.

Embodiment 56. The method of Embodiment 55, wherein the administering is an intramuscular injection, intradermal injection, or subcutaneous injection.

Embodiment 57. The method of Embodiment 55 or 56, wherein the administering is carried out without regard to whether the subject has food, i.e., the compound or pharmaceutical composition is administered with or without food.

Embodiment 58. The method of any one of Embodiments 55-57, wherein the hormone-dependent benign or malignant disorder is prostate cancer or breast cancer.

Embodiment 59. The method of any one of Embodiments 55-57, wherein the hormone-dependent benign or malignant disorder is castration resistant prostate cancer or castration sensitive prostate cancer.

Embodiment 60. The method of any one of Embodiments 55-57, wherein the hormone-dependent benign or malignant disorder is metastatic castration resistant prostate cancer or metastatic castration sensitive prostate cancer.

Embodiment 61. The method of any one of Embodiments 55-60, wherein the subject is treated with a gonadotropin-releasing hormone analog and/or bilateral orchiectomy.

Embodiment 62. The method of any one of Embodiments 55-61, further comprising administering to the subject an effective amount of prednisone or prednisolone.

Embodiment 63. The method of any one of Embodiments 55-62, wherein the pharmaceutical composition is administered to the subject once a week or once in more than a week, e.g., the dosing frequency ranges from once a week to once every few months, such as from once a week to once every eight weeks, or once a week to once every three months.

Embodiment 64. The method of any one of Embodiments 55-63, wherein the administering provides a blood plasma concentration of abiraterone above 1.0 ng/ml for a period of at least two weeks.

Embodiment 65. The method of any one of Embodiments 55-63, wherein the administering provides a blood plasma concentration of abiraterone above 8.4 ng/ml for a period of at least two weeks.

Embodiment 66. The method of any one of Embodiments 55-65, wherein the administering provides a single dose or steady state $C_{max}$ of abiraterone between about 10 ng/ml and about 400 ng/ml (e.g., between about 50 ng/ml and about 100 ng/ml, or between about 15 ng/ml and about 160 ng/ml).

Provided herein are formulations, methods, and kits for treating a subject with a sex hormone-dependent benign or malignant disorder such as prostate cancer. Also provided are methods for preparing the formulations useful for treating a subject with a sex hormone-dependent benign or malignant disorder (such as prostate cancer), a syndrome due to androgen excess, and/or a syndrome due to glucocorticoid excess such as hypercortisolemia. Reference will now be made in detail to representative embodiments, examples of which are illustrated in the accompanying drawings.

The term "subject" as used herein means, but is not limited to, an animal or human in need of or capable of receiving chemotherapy for a sex hormone-dependent benign or malignant disorder such as, for example, an androgen-dependent disorder or an estrogen-dependent disorder (including prostate cancer and breast cancer), an animal or human in need of or capable of receiving therapy for non-oncologic syndromes due to androgen excess, such as endometriosis, polycystic ovary syndrome, congenital adrenal hyperplasia (e.g., classical or nonclassical congenital adrenal hyperplasia), precocious puberty, hirsutism, etc., and/or due to glucocorticoid excess such as hypercortisolemia, such as Cushing's syndrome or Cushing's disease. In preferred embodiments, the subject is a human subject.

The term "other drug or agent" as used herein (when, for example, referring to prior, simultaneous, and post-administration of at least one other drug or agent with at least one abiraterone prodrug formulation) means at least one other compound, formulation, molecule, biologic, or the like, capable of enhancing the efficacy of the formulation(s), decreasing an undesirable side effect(s) of the formulation(s), or improving the treatment of the particular disorder. Any suitable routes of administration of such "other drug or agent" can be used, for example, oral administration, parenteral administration, etc. A person skilled in the art of treating a subject having a sex hormone-dependent benign or malignant disorder (such as an androgen-dependent disorder or an estrogen-dependent disorder), syndromes due to androgen excess syndrome, and/or syndromes due to glucocorticoid excess such as hypercortisolemia would know and understand how to choose and use such "other drug or agent" for the intended purpose(s).

The formulations can optionally be administered via a modified-release device or method. The term "modified-release" as used herein should be understood as encompassing delayed release, prolonged or extended release, sustained release, or a targeted release, etc. For example, in some embodiments, the modified release device or method can further prolong the release of abiraterone of the prodrugs and formulations of the present disclosure. In some embodiments, the modified release device or method can also include any device or method capable of releasing an agent or product (for example, a drug or a biologic) at a time later than immediately following its administration (and can include, for example, implants). Various modified release devices have been described (Stubbe et al., *Pharm. Res.* 21:1732, 2004) and could be applicable to the representative embodiments. Modified-release devices and methods can be identified and employed without undue experimentation by a person skilled in the art after consideration of all criteria and use of best judgment on the subject's behalf.

The formulations and agents of the embodiments are administered in a pharmacologically or physiologically acceptable and effective amount to reduce or eliminate the presence, for example, of prostate tumor tissue and abnormal or malignant prostate cells in a subject presenting with prostate cancer. Similarly, the formulations and agents of the embodiments are administered alone or in combination with other therapeutic agents or therapeutic modalities (for example, radiotherapy and surgery) in prophylactically or therapeutically effective amounts, which are to be understood as amounts meeting the intended prophylactic or therapeutic objectives, and providing the benefits available from administration of such formulations and agents.

The terms "effective amount," "effective dose," and "therapeutic blood plasma concentration" as used herein mean, but are not limited to, an amount, dose, or concentration capable of treating, delaying, slowing, inhibiting or eliminating the onset, existence or progression of a disorder, disease or condition. For example, an "effective amount," "effective dose," or "therapeutic blood plasma concentration" is capable of reducing or eliminating the presence of prostate tumor tissue and abnormal or malignant prostate cells in a subject presenting with prostate cancer, which is sufficient to cure (partly or completely) illness or prevent the onset or further spread of disorder, disease or condition. For further example, an effective amount of formulation refers to the amount administered alone or in combination with other therapeutic agents or therapeutic modalities (for example, radiotherapy and surgery) to achieve clinically-significant reduction in tumor burden. A person skilled in the art would understand when a clinically-significant reduction in tumor burden (or improvement of a sex hormone-dependent benign or malignant disorder or another disorder or syndrome described herein) has occurred following administration of a formulation. An "effective amount," "effective dose," or "therapeutic blood plasma concentration" is understood to be an amount, dose, or concentration not critically harmful to the subject and, in any case, where any harmful side effects are outweighed by benefits. By way of example only, an effective amount or dose of an abiraterone prodrug formulation means an amount capable of attaining blood plasma concentrations of at least 1 ng/ml, e.g., at least 1 ng/ml, at least 2 ng/ml, at least 4 ng/ml, or at least 8 ng/ml, of abiraterone in the subject following parenteral administration of the prodrug formulation, and the efficacious blood plasma concentrations are attained for at least one week, e.g., at least two weeks (for example, four, six, eight or more weeks) following administration.

In general, the dosage ranges for administration of the formulation according to the present disclosure are those that produce the desired effect(s). The useful dosage to be administered will vary depending on the age, weight, and health of the subject treated, the mode, route, and schedule of administration, the response of the individual subject, and the type or staging of prostate cancer (or severity of a sex hormone-dependent benign or malignant disorder or another syndrome or disorder described herein) against which treatment with the formulation is sought. The dosage will also vary with the nature or the severity of the primary tumor and other underlying conditions, with epidemiologic conditions, with the concomitant use of other active compounds, and the route of administration. In addition, the dosage will be determined by the existence of any adverse side effects such as local hypersensitivity, systemic adverse effects, and immune tolerance.

An effective dose of the formulations (and other agent(s)) can be determined without undue experimentation (for example, by pharmacokinetic studies) by a person skilled in the art after consideration of all criteria and use of best judgment on the patient's behalf (and will most often be contingent upon the particular formulation utilized). The dosage to be administered will depend upon the particular case, but in any event, it is the amount sufficient to induce clinical benefit against, or improvement of, a sex hormone-dependent benign or malignant disorder (such as prostate cancer), a syndrome due to androgen excess, and/or a syndrome due to glucocorticoid excess such as hypercortisolemia.

The formulations and agents of the embodiments can, optionally, be administered in combination with (or can include) one or more pharmaceutically acceptable carriers, diluents, or excipients. Formulations, administration techniques, pharmaceutical compositions, methods of preparing pharmaceutical compositions, and pharmaceutically acceptable carriers, diluents, and excipients are known in the art and are described, for example, in "Remington: The Science and Practice of Pharmacy" (formerly "Remington's Pharmaceutical Sciences," University of the Sciences in Philadelphia, Lippincott, Williams & Wilkins, Philadelphia, Pa. (2005)), the disclosure of which is hereby incorporated by reference. A person skilled in the art can use known injectable, physiologically acceptable sterile solutions. For preparing a ready-to-use solution for parenteral injection or infusion, aqueous isotonic solutions, for example, saline, phosphate buffered saline (PBS) or corresponding plasma protein solutions, are readily available. The formulations can be present as lyophilisates or dry preparations, which can be reconstituted with a known injectable solution directly before use under sterile conditions, for example, as a kit of parts. In addition, the formulations can include one or more acceptable carriers (which can include, for example, solvents, dispersion media, coatings, adjuvants, stabilizing agents, diluents, preservatives, antibacterial and antifungal agents, isotonic agents, absorption-modifying agents, and the like. "Diluents" can include water, saline, phosphate-buffered saline (PBS), dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

Any suitable route of administration can be employed for providing a subject with an effective amount/dosage of formulation and agents according to the representative embodiments. A suitable route of administration can be determined readily by a person skilled in the art of pharmacology, immunology, medicine, oncology, or the like without undue experimentation. However, it is anticipated that the formulations are primarily suitable for parenteral administration such as via IM injection, intradermal injection, or subcutaneous injection.

The abbreviations used herein have their conventional meaning within the chemical and biological arts.

It is also meant to be understood that a specific embodiment of a variable moiety herein may be the same or different as another specific embodiment having the same identifier.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

As used herein, the term "alkyl" as used by itself or as part of another group refers to a straight- or branched-chain saturated aliphatic hydrocarbon. In some embodiments, the alkyl can include one to thirty carbon atoms (i.e., $C_{1-30}$ alkyl or alternatively expressed as $C_1$-$C_{30}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-16}$ alkyl group. In another embodiment, the alkyl group is a branched chain $C_{3-16}$ alkyl group.

As used herein, the term "cycloalkyl" as used by itself or as part of another group refers to saturated and partially unsaturated (e.g., containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl.

As used herein, the term "alkenyl" as used by itself or as part of another group refers to a straight- or branched-chain aliphatic hydrocarbon containing one or more (e.g., 1, 2, or 3) carbon-to-carbon double bonds. In one embodiment, the alkenyl group is a $C_{2-16}$ alkenyl group.

As used herein, the term "alkynyl" as used by itself or as part of another group refers to a straight- or branched-chain aliphatic hydrocarbon containing one or more (e.g., 1, 2, or 3) carbon-to-carbon triple bonds. In one embodiment, the alkynyl has one carbon-carbon triple bond. In one embodiment, the alkynyl group is a $C_{2-16}$ alkynyl group.

As used herein, the term "abiraterone prodrug(s) of the present disclosure" refers to any of the compounds described herein according to Formula I or II, a lipophilic ester of abiraterone prodrug, or any of Example Nos. 2A-2H, isotopically labeled compound(s) thereof (e.g., deuterium enriched compounds), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt). Hydrates and solvates of the prodrugs of the present disclosure are considered compositions of the present disclosure, wherein the prodrug(s) is in association with water or solvent, respectively. Some of the prodrugs of the present disclosure can also exist in various polymorphic forms or amorphous forms. The prodrugs described herein include those compounds that readily undergo chemical changes under physiological conditions to provide active abiraterone. Additionally, prodrugs can be converted by chemical or biochemical methods in an ex vivo environment. As used herein, the term "abiraterone prodrug formulation(s) of the present disclosure" refers to any of the pharmaceutical composition or formulation comprising any one or more of the abiraterone prodrugs of the present disclosure, for example, any of the formulations prepared in Examples 3A-3J. In any of the embodiments described herein, unless directly contradictory from context, the abiraterone prodrug of the present disclosure can be abiraterone decanoate. In any of the embodiments described herein, unless directly contradictory from context, the abiraterone prodrug formulation of the present disclosure can be any of the pharmaceutical composition comprising abiraterone decanoate as described herein. In any of the embodiments described herein, unless directly contradictory from context, the abiraterone prodrug of the present disclosure can also be abiraterone isocaproate. In any of the embodiments described herein, unless directly contradictory from context, the abiraterone prodrug formulation of the present disclosure can also be any of the pharmaceutical composition comprising abiraterone isocaproate as described herein.

The abiraterone prodrugs of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, oxygen, and nitrogen, include, but are not limited to $^2$H, $^3$H, $^{13}$C, $^{14}$C, $^{15}$N, and $^{18}$O. Compounds that contain other isotopes of these and/or other atoms are within the scope of this disclosure.

Solid and dashed wedge bonds indicate stereochemistry as customary in the art.

The following examples are provided for illustration purposes only, and are in no way intended to limit the scope of the claimed subject matter.

Example 1 Long-Acting Injectable Formulations of Abiraterone Prodrugs

The formulations include long acting injectable oil-based formulations of a lipophilic abiraterone prodrug such as (1) abiraterone 30-alkanoates and (2) linear, branched, cyclic, and aromatic alkanotes of C-2 to C-16 carbons (that is, aliphatic and aromatic esters made of 2 to 16 carbon atoms). The abiraterone esters can include, for example, the following esters: an acetate, a propionate, a butanoate, a (vaterate) pentanoate, an isocaproate, a buciclate, a cyclohexanecarboxylate, a phenyl propionate, caproate (hexanoate), a enanthate (heptanoate), a cypionate, an octanoate, a noncanoate, a decanoate, an undecanoate, a dodecanoate, a tridecanoate, a tetradecanoate, a pentadecanoates, and a hexadecanoate. In representative embodiments, the abiraterone esters are abiraterone acetate, abiraterone propionate, and abiraterone decanoate.

The formulations can comprise a solution or suspension of abiraterone prodrug in pharmaceutically acceptable oils, such as pharmaceutically acceptable oils for injection, including oils of vegetable origin or synthetic mono- or diglycerides of fatty acids. In some embodiments, pharmaceutically acceptable oils can include triglycerides made up of fatty acids (poly-unsaturated, mono-unsaturated, and saturated) such as the following: vegetable oil, castor oil, corn oil, sesame oil, cottonseed oil, peanut oil (arachis oil), poppy seed oil, tea seed oil, and soybean oil. Vegetable oils were selected based on the solubility of the prodrug in the oil. It was determined that abiraterone acetate was most soluble in castor oil, which includes a triglyceride, in which the fatty acid constituent is primarily rich in oleic acid (a hydroxylated monounsaturated fatty acid). Conversely, it was determined that the more lipophilic prodrugs (abiraterone propionate and abiraterone decanoate) were more soluble in corn oil, which includes a triglyceride, in which the fatty acid constituents are primarily linoleic acid (non-hydroxylated polyunsaturated fatty acid), oleic acid (non-hydroxylated unsaturated fatty acid), palmitic acid (non-hydroxylated saturated fatty acid), and stearic acid (non-hydroxylated saturated fatty acid). Surprisingly, it was determined that abiraterone butanoate has lower solubility in both castor oil and corn oil than the acetate, propionate, or decanoate prodrugs. It was also noted that there is an inverse correlation between the melting points and solubilities of the prodrugs in vegetable oils. The melting points of the various abiraterone prodrugs were determined by differential scanning calorimetry as shown in Table 1.

TABLE 1

Melting Points of Abiraterone Prodrugs.

| Abiraterone Prodrug | Melting point |
| --- | --- |
| Acetate | 127-130° C. |
| Propionate | 102° C. |
| Butanoate | 147° C. |
| Decanoate | 38° C. |

The formulations can contain pharmaceutically acceptable excipients such as co-solvents (that is, solubilizing agents) such as benzyl alcohol, benzyl benzoate, ethanol, glycerol, polyethylene glycol, polysorbate 80, acetic acid, and ethyl acetate. It was determined that the additives/co-solvents benzyl alcohol and benzyl benzoate had the advantage of increasing the solubility of the prodrugs as well as reducing the viscosity and glide force of the solution, see e.g., FIGS. 13A-13E and Tables 2A-2D, which provided a more concentrated solution that was easier to inject through an acceptable gauge needle for IM injection (e.g., 20-27 gauge such as 22-25 gauge). Indeed, the co-solvent is selected based on its ability to reduce the viscosity of the vehicle to allow injection through suitable injection needles or cannula. Benzyl alcohol as an additive in IM or subcutaneous injections also has the advantage that it can act as a local anesthetic at the injection site (Wilson et al. Ann. Emer. Med. 33(5), 495, 1999).

The solubility of the abiraterone esters can be affected upon adding a co-solvent to the vegetable oil vehicle. Thus, in some embodiments, the abiraterone ester is completely dissolved in the composition, and in other embodiments the abiraterone ester is partly dispersed in the composition. In one embodiment, the abiraterone esters are fully dissolved in the vehicle.

The formulations can also contain pharmaceutically acceptable preservatives, polymers, antioxidants, antimicrobials, chelating agents, and other excipients such as citric acid, dextrose, ascorbic acid, benzalkonium chloride, benzoic acid, sodium betadex sulfobutyl ether, calcium chloride, sodium carbomethoxycellulose, chlorobutanol, creatine, croscarmellose, dibasic potassium phosphate, sodium docusate, sodium edetate, glycerin, sodium hyaluronate, hydroxypropyl betadex, lactic acid, lactose, lecithin, maleic acid, mannitol, meglumine, methylcellulose, methylparaben, microcrystalline cellulose, miripitium chloride, monothioglycerol, phenol, poloxamer 188, polyglactin, polysorbate 20, polysorbate 40, polysorbate 80, propylparaben, sodium acetate, sodium benzoate, sodium citrate, sorbitan monolaurate, sorbitol, sucrose, tartaric acid, trisodium citrate, tromantadine, tromethamine, and urea.

The formulations can be sterilized by methods known by persons skilled in the art (for example, gamma irradiation, micron filtration, and autoclaving).

The abiraterone prodrug formulations can be prepared at various concentrations including, for example, 25 mg/ml to 500 mg/ml. In representative embodiments the concentrations are 50 mg/ml to 300 mg/ml.

The formulations, following IM or subcutaneous injection, release an effective amount of abiraterone over a period of at least one week and up to two, three, four, or more weeks. The therapeutic blood plasma levels of abiraterone achieved following administration of the abiraterone prodrug formulations can be, for example, 6-15 ng/ml between 14-28 days following parenteral administration. In representative embodiments, the therapeutic levels are 8-12 ng/ml between 14-28 days following parenteral administration. It has been demonstrated that an abiraterone $C_{min}$ of >8.4 ng/ml is associated with a favorable prostate-specific antigen response and could be a crucial predictive factor for progression-free survival in castration resistant prostate cancer patients (Carton et al., *Eur. J. Cancer,* 72:54, 2017).

Example 2. Synthesis of Abiraterone Prodrugs

Abiraterone Acetate

Abiraterone acetate was obtained from Hetero Labs Limited, India.

Other abiraterone esters can be synthesized generally by reacting abiraterone with $R^2COOH$ or an appropriate activated form thereof, such as $R^2COCl$. The reaction is typically carried out in an aprotic solvent such as $CHCl_3$ with an appropriate base such as triethyl amine. Examples of preparation of abiraterone propionate, abiraterone butanoate, abiraterone pentanoate, abiraterone hexanoate, abiraterone heptanoate, abiraterone isocaproate, abiraterone cypionate, and abiraterone decanoate are shown below.

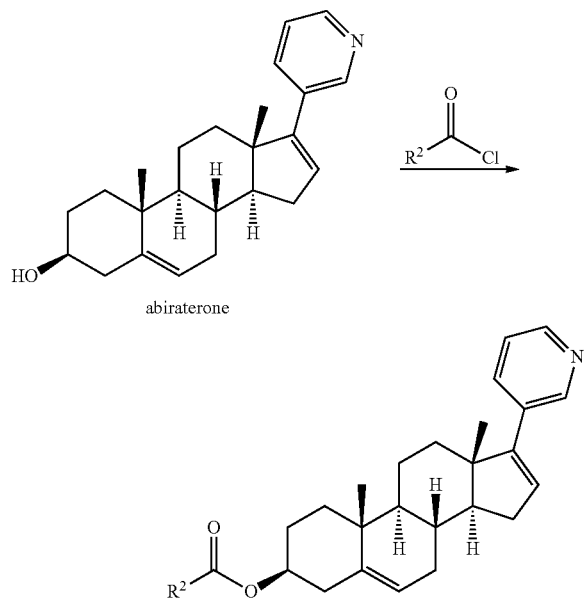

Example 2A. Preparation of Abiraterone Propionate

Abiraterone propionate was prepared as follows:

15.0 g (42.9 mmol) of abiraterone was added to a 500 ml round-bottom flask followed by 450 ml of chloroform and 11.96 ml (85.8 mmol, 2.0 equiv) of triethylamine. The flask was purged with nitrogen and the mixture was cooled to 0° C. in an ice bath. After stirring the mixture for 15 minutes, 4.12 ml (47.2 mmol, 1.1 equiv) of propanoyl chloride were added dropwise followed by addition of an additional 6.57 ml (47.2 mmol, 1.1 equiv) of triethylamine. The ice bath was removed, and the solution was stirred for an additional 2 hours. The reaction was once again cooled to 0° C., and an additional 4.12 ml of propanoyl chloride and 6.57 mL of triethylamine were added slowly. The ice bath was again removed, and the reaction stirred for another 16 hours. The solution was then washed twice with 300 ml of water and once with 300 ml of brine. The organic phase was dried over sodium sulfate, concentrated under vacuum, and loaded onto silica. The crude compound was purified by flash chromatography using an ethyl acetate/hexane solvent system. The desired compound was eluted with approximately 30% ethyl acetate. The pure fractions were combined and concentrated under vacuum to provide 8.2 g of abiraterone propionate as a yellow solid, which was 97.8% pure according to HPLC analysis. Other chemical properties were as follows: LCMS m/z 406.3 (M+H); $^1$H NMR (CDCl$_3$, 200 MHz): $\delta_H$ 1.096 (11H, m), 1.625 (11H, m), 1.846 (3H, m), 2.067 (3H, m), 2.323 (5H, m), 4.627 (1H, m), 5.415 (1H, d, J=5 Hz), 5.992 (1H, q, J=5 Hz), 7.215 (1H, ddd, J=1, 5.8 Hz), 7.677 (1H, dt, J=2.8 Hz), 8.456 (1H, dd, J=2.5 Hz), 8.619 (1H, dd, J=1.2 Hz); melting point (DSC) 101° C.

Example 2B. Preparation of Abiraterone Butanoate

Abiraterone butanoate was prepared as follows:

7.0 g (20.0 mmol) of abiraterone was added to a 500 ml round-bottom flask followed by 210 ml of chloroform and 5.58 ml (40.0 mmol, 2.0 equiv) of triethylamine. The flask was purged with nitrogen and the mixture was cooled to 0° C. in an ice bath. After stirring the mixture for 15 minutes, 2.28 ml (22.0 mmol, 1.1 equiv) of butanoyl chloride were added dropwise followed by addition of an additional 3.07 ml (22.0 mmol, 1.1 equiv) of triethylamine. The ice bath was removed, and the solution was stirred for an additional 2 hours. The reaction was once again cooled to 0° C., and an additional 2.28 ml of butanoyl chloride and 3.07 mL of triethylamine were added slowly. The ice bath was again removed, and the reaction stirred for another 16 hours. During the course of the reaction, the color changed quickly from a white mixture to a yellow solution and then slowly to a red solution. After confirmation by TLC and LCMS that the reaction was complete, the solution was then washed twice with 150 ml of water and once with 150 ml of brine. The organic phase was dried over sodium sulfate, concentrated under vacuum, and loaded onto silica. The crude compound was purified by flash chromatography using an ethyl acetate/hexane solvent system. The desired compound was eluted with approximately 25% ethyl acetate. The pure fractions were combined and concentrated under vacuum to provide 5.5 g of abiraterone butanoate as a yellow solid. Chemical properties were as follows: LCMS m/z 420.4 (M+H); $^1$H NMR (CDCl$_3$, 200 MHz): $\delta$H 0.948 (3H, t, J=7 Hz), 1.043 (3H, s), 1.090 (3H, s), 1.633 (15H, m), 1.842 (3H, m), 2.065 (3H, m), 2.297 (5H, m), 4.608 (1H, m), 5.413 (1H, d, J=5 Hz), 5.990 (1H, q, J=5 Hz), 7.215 (1H, ddd, J=1, 5.8 Hz), 7.643 (1H, dt, J=2.8 Hz), 8.455 (1H, dd, J=2.5 Hz), 8.615 (1H, dd, J=1.2 Hz); melting point (DSC) 147° C.

Example 2C. Preparation of Abiraterone Decanoate

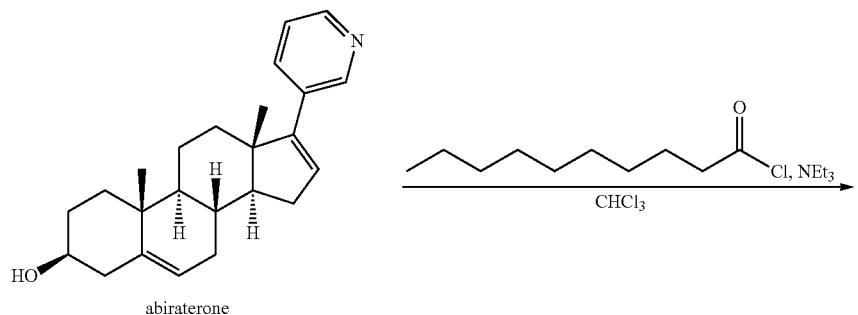

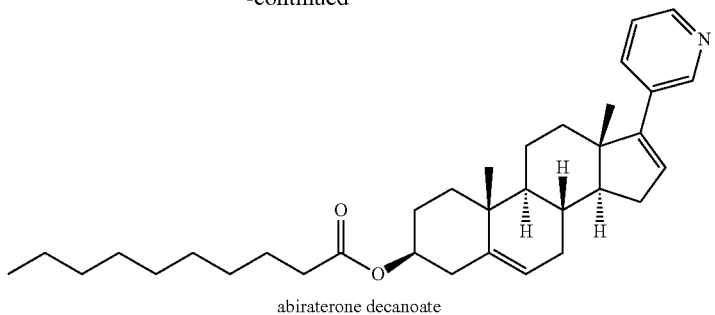

abiraterone decanoate

Abiraterone decanoate was prepared as follows:

10.0 g (28.6 mmol) of abiraterone was added to a 500 ml round-bottom flask followed by 300 ml of chloroform and 7.97 ml (57.2 mmol, 2.0 equiv) of triethylamine. The flask was purged with nitrogen and the mixture was cooled to 0° C. in an ice bath. After stirring the mixture for 15 minutes, 6.53 ml (31.5 mmol, 1.1 equiv) of decanoyl chloride were added dropwise followed by addition of an additional 4.39 ml (31.5 mmol, 1.1 equiv) of triethylamine. The ice bath was removed, and the solution was stirred for an additional 2 hours. The reaction was once again cooled to 0° C., and an additional 6.53 ml of decanoyl chloride and 4.39 mL of triethylamine were added slowly. The ice bath was again removed, and the reaction stirred for another 16 hours. During the course of the reaction, the color changed quickly from a white mixture to a yellow solution and then slowly to a red solution. After confirmation by TLC and LCMS that the reaction was complete, the solution was then washed twice with 200 ml of water and once with 200 ml of brine. The organic phase was dried over sodium sulfate, concentrated under vacuum, and loaded onto silica. The crude compound was purified by flash chromatography using an ethyl acetate/hexane solvent system. The desired compound was eluted with approximately 20% ethyl acetate. The pure fractions were combined and concentrated under vacuum to provide 8.0 g of abiraterone decanoate as a yellow solid. Chemical properties were as follows: LCMS m/z 504.4 (M+H); $^1$H NMR (CDCl$_3$, 200 MHz): δH 0.877 (3H, t, J=7 Hz), 1.043 (3H, s), 1.082 (3H, s), 1.268 (16H, m), 1.643 (15H, m), 1.842 (3H, m), 2.065 (3H, m), 2.290 (5H, m), 4.602 (1H, m), 5.404 (1H, d, J=5 Hz), 5.998 (1H, q, J=5 Hz), 7.215 (1H, ddd, J=1, 5.8 Hz), 7.643 (1H, dt, J=2.8 Hz), 8.455 (1H, dd, J=2.5 Hz), 8.617 (1H, dd, J=1.2 Hz); melting point (DSC) 38° C.

Example 2D. Preparation of Abiraterone Pentanoate

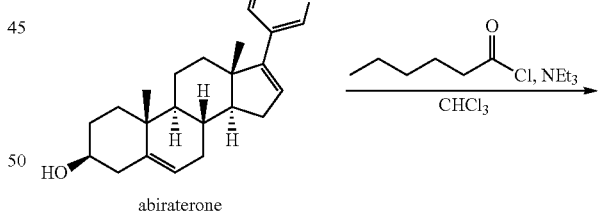

abiraterone

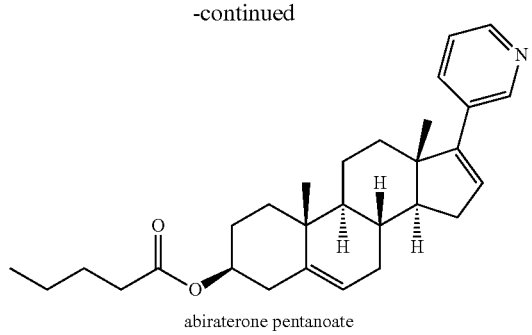

abiraterone pentanoate

Abiraterone pentanoate was prepared using a procedure similar to the procedure for preparing abiraterone decanoate (Example 2C), except that valeroyl chloride was used instead of decanoyl chloride. LCMS m/z 434.3 (M+H); $^1$H NMR (CDCl$_3$, 200 MHz): δ$_H$ 0.9-2.2 (32H, m), 4.61 (1H, m), 5.41 (1H, d, J=5 Hz), 5.99 (1H, q, J=5 Hz), 7.22 (1H, ddd, J=1, 5.8 Hz), 7.63 (1H, dt, J=2.8 Hz), 8.45 (1H, dd, J=2.5 Hz), 8.62 (1H, dd, J=1.2 Hz).

Example 2E. Preparation of Abiraterone Hexanoate

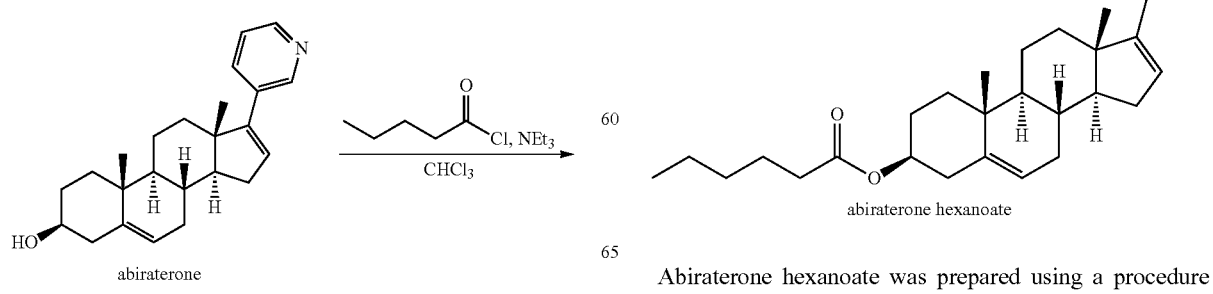

Abiraterone hexanoate was prepared using a procedure similar to the procedure for preparing abiraterone decanoate (Example 2C), except that hexanoyl chloride was used instead of decanoyl chloride. LCMS m/z 448.4 (M+H); $^1$H NMR (CDCl$_3$, 200 MHz): $\delta_H$ 0.9-2.2 (34H, m), 4.60 (1H, m), 5.40 (1H, d, J=5 Hz), 5.98 (1H, q, J=5 Hz), 7.21 (1H, ddd, J=1, 5.8 Hz), 7.62 (1H, dt, J=2.8 Hz), 8.43 (1H, dd, J=2.5 Hz), 8.60 (1H, dd, J=1.2 Hz).

Example 2F. Preparation of Abiraterone Heptanoate

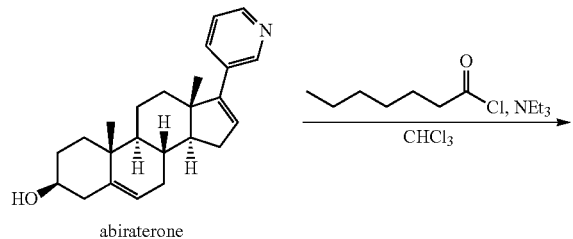

Abiraterone heptanoate was prepared using a procedure similar to the procedure for preparing abiraterone decanoate (Example 2C), except that heptanoyl chloride was used instead of decanoyl chloride. LCMS m/z 462.4 (M+H); $^1$H NMR (CDCl$_3$, 200 MHz): $\delta_H$ 0.9-2.2 (36H, m), 4.61 (1H, m), 5.40 (1H, d, J=5 Hz), 6.00 (1H, q, J=5 Hz), 7.21 (1H, ddd, J=1, 5.8 Hz), 7.64 (1H, dt, J=2.8 Hz), 8.45 (1H, dd, J=2.5 Hz), 8.61 (1H, dd, J=1.2 Hz).

Example 2G. Preparation of Abiraterone Isocaproate

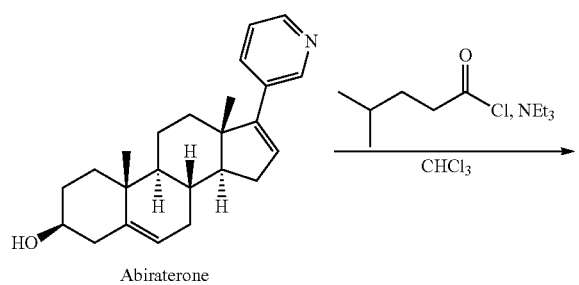

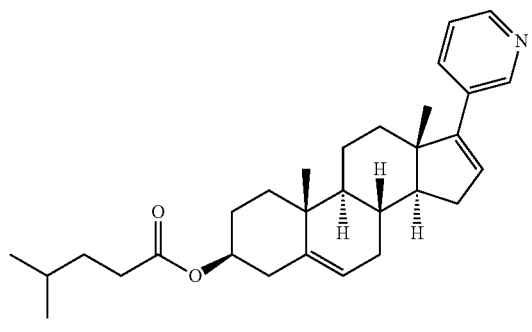

Abiraterone isocaproate was prepared using a procedure similar to the procedure for preparing abiraterone decanoate (Example 2C), except that 4-methylvaleryl chloride was used instead of decanoyl chloride. LCMS m/z 448.4 (M+H); $^1$H NMR (CDCl$_3$, 200 MHz): $\delta_H$ 0.9-2.2 (34H, m), 4.61 (1H, m), 5.40 (1H, d, J=5 Hz), 6.00 (1H, q, J=5 Hz), 7.22 (1H, ddd, J=1, 5.8 Hz), 7.64 (1H, dt, J=2.8 Hz), 8.45 (1H, dd, J=2.5 Hz), 8.62 (1H, dd, J=1.2 Hz).

Example 2H. Preparation of Abiraterone Cypionate

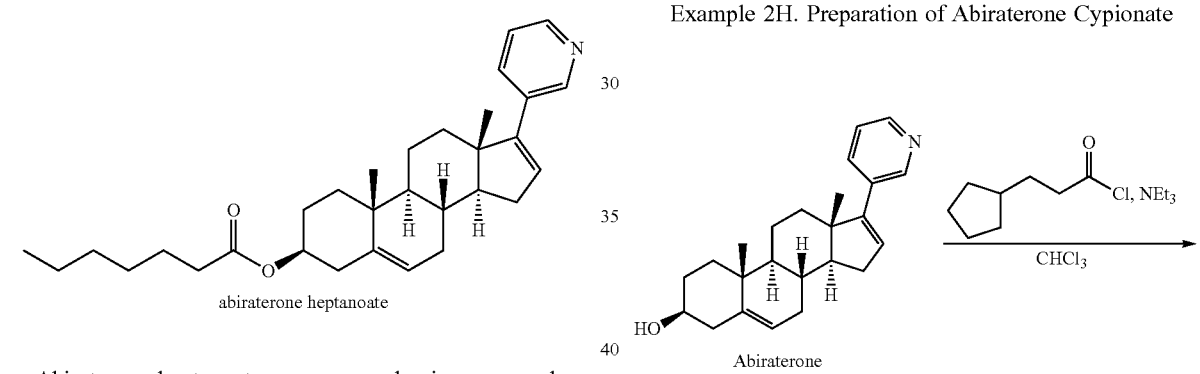

Abiraterone cypionate was prepared using a procedure similar to the procedure for preparing abiraterone decanoate (Example 2C), except that 3-cyclopentylpropanoyl chloride was used instead of decanoyl chloride. LCMS m/z 474.4 (M+H); $^1$H NMR (CDCl$_3$, 200 MHz): $\delta_H$ $^1$H NMR (CDCl$_3$, 200 MHz): $\delta_H$ 0.9-2.3 (36H, m), 4.62 (1H, m), 5.41 (1H, d, J=5 Hz), 6.00 (1H, q, J=5 Hz), 7.22 (1H, ddd, J=1, 5.8 Hz), 7.63 (1H, dt, J=2.8 Hz), 8.45 (1H, dd, J=2.5 Hz), 8.62 (1H, dd, J=1.2 Hz).

Example 3. Preparation of Formulations of Abiraterone Prodrugs

Example 3A. Preparation of Abiraterone Acetate Castor Oil Solution

An abiraterone acetate injectable (IM depot) castor oil solution was prepared as follows:

490 mg of abiraterone acetate was weighed and placed in a 10-mL serum vial with a crimped stopper. 8 mL of castor oil was placed in a separate 10-mL serum vial with a crimped stopper. The two vials were then wrapped in aluminum foil and sterilized in an autoclave using a 30-minute liquid cycle. Following sterilization, the vials were moved to a laminar flow hood. Then, 7 mL of the sterile castor oil was removed and added to the sterile abiraterone acetate and the vial was re-stoppered and crimped closed. The abiraterone acetate was then dissolved by sonicating, vortexing, and placing the vials on a rotator. The final concentration of the sterile solution of abiraterone acetate was 70 mg/ml.

Example 3B. Preparation of Abiraterone Acetate 90% Castor Oil, 10% Benzyl Alcohol Solution An abiraterone acetate injectable (IM depot) 90% castor oil, 10% benzyl alcohol solution was prepared as follows:

700 mg of abiraterone acetate was weighed and placed in a 10-mL serum vial with a crimped stopper. 8 mL of a 90% castor oil/10% benzyl alcohol mixture was placed in a separate 10-mL serum vial with a crimped stopper. The two vials were then wrapped in aluminum foil and sterilized in an autoclave using a 30-minute liquid cycle. Following sterilization, the vials were moved to a laminar flow hood. Then, 7 mL of the sterile 90% castor oil/10% benzyl alcohol solution was removed and added to the sterile abiraterone acetate and the vial was re-stoppered and crimped closed. The abiraterone acetate was then dissolved by sonicating, vortexing, and placing the vials on a rotator. The final concentration of the sterile solution of abiraterone acetate was 91 mg/ml.

Example 3C. Preparation of Abiraterone Acetate 50% Castor Oil, 50% Benzyl Benzoate Solution An abiraterone acetate injectable (IM depot) 50% castor oil, 50% benzyl benzoate solution was prepared as follows:

980 mg of abiraterone acetate was weighed and placed in a 10-mL serum vial with a crimped stopper. 8 mL of a 50% castor oil/50% benzyl benzoate mixture was placed in a separate 10-mL serum vial with a crimped stopper. The two vials were then wrapped in aluminum foil and sterilized in an autoclave using a 30-minute liquid cycle. Following sterilization, the vials were moved to a laminar flow hood. Then, 7 mL of the sterile 50% castor oil/50% benzyl benzoate mixture solution was removed and added to the sterile abiraterone acetate and the vial was re-stoppered and crimped closed. The abiraterone acetate was then dissolved by sonicating, vortexing, and placing the vials on a rotator. The final concentration of the sterile solution of abiraterone acetate was 124 mg/ml.

Example 3D. Preparation of Abiraterone Propionate 90% Castor Oil, 10% Benzyl Alcohol Solution An abiraterone propionate injectable (IM depot) 90% castor oil, 10% benzyl alcohol solution was prepared as follows:

1,050 mg of abiraterone propionate was weighed and placed in a 10-mL serum vial with a crimped stopper. 8 mL of a 90% castor oil/10% benzyl alcohol mixture was placed in a separate 10-mL serum vial with a crimped stopper. The vehicle vial was then wrapped in aluminum foil and sterilized in an autoclave using a 30-minute liquid cycle. Following sterilization, the vials were moved to a laminar flow hood. Then, 8 mL of the sterile 90% castor oil/10% benzyl alcohol solution was removed and added to the abiraterone propionate and the vial was re-stoppered and crimped closed. The abiraterone propionate was then dissolved by sonicating, vortexing, and placing the vials on a rotator. The final concentration of the sterile solution of abiraterone propionate was 197 mg/ml.

Example 3E. Preparation of Abiraterone Propionate 90% Corn Oil, 10% Benzyl Alcohol Solution An abiraterone propionate injectable (IM depot) 90% corn oil, 10% benzyl alcohol solution was prepared as follows:

1,050 mg of abiraterone propionate was weighed and placed in a 10-mL serum vial with a crimped stopper. 8 mL of a 90% corn oil/10% benzyl alcohol mixture was placed in a separate 10-mL serum vial with a crimped stopper. The vehicle vial was then wrapped in aluminum foil and sterilized in an autoclave using a 30-minute liquid cycle. Following sterilization, the vials were moved to a laminar flow hood. Then, 8 mL of the sterile 90% corn oil/10% benzyl alcohol solution was removed and added to the abiraterone propionate and the vial was re-stoppered and crimped closed. The abiraterone propionate was then dissolved by sonicating, vortexing, and placing the vials on a rotator. The final concentration of the sterile solution of abiraterone propionate was 168 mg/ml.

Example 3F. Preparation of Abiraterone Decanoate 90% Castor Oil, 10% Benzyl Alcohol Solution An abiraterone decanoate injectable (IM depot) 90% castor oil, 10% benzyl alcohol solution was prepared as follows:

1,260 mg of abiraterone decanoate was weighed and placed in a 10-mL serum vial with a crimped stopper. 8 mL of a 90% castor oil/10% benzyl alcohol mixture was placed in a separate 10-mL serum vial with a crimped stopper. The vehicle vial was then wrapped in aluminum foil and sterilized in an autoclave using a 30-minute liquid cycle. Following sterilization, the vials were moved to a laminar flow hood. Then, 8 mL of the sterile 90% castor oil/10% benzyl alcohol solution was removed and added to the abiraterone decanoate and the vial was re-stoppered and crimped closed. The abiraterone decanoate was then dissolved by sonicating, vortexing, and placing the vials on a rotator. The final concentration of the sterile solution of abiraterone decanoate was 160 mg/ml.

Example 3G. Preparation of Abiraterone Decanoate 90% Corn Oil, 10% Benzyl Alcohol Solution An abiraterone decanoate injectable (IM depot) 90% corn oil, 10% benzyl alcohol solution was prepared as follows:

1,260 mg of abiraterone decanoate was weighed and placed in a 10-mL serum vial with a crimped stopper. 8 mL of a 90% corn oil/10% benzyl alcohol mixture was placed in a separate 10-mL serum vial with a crimped stopper. The vehicle vial was then wrapped in aluminum foil and sterilized in an autoclave using a 30-minute liquid cycle. Following sterilization, the vials were moved to a laminar flow hood. Then, 8 mL of the sterile 90% corn oil/10% benzyl alcohol solution was removed and added to the abiraterone decanoate and the vial was re-stoppered and crimped closed. The abiraterone decanoate was then dissolved by sonicating, vortexing, and placing the vials on a rotator. The final concentration of the sterile solution of abiraterone decanoate was 170 mg/ml.

Example 3H. Preparation of Abiraterone Decanoate (~200 mg/ml) 70% Corn Oil, 10% Benzyl Alcohol, 20% Benzyl Benzoate Solution An abiraterone decanoate injectable (IM depot ~200 mg/ml) 70% corn oil, 10% benzyl alcohol, 20% benzyl benzoate solution was prepared as follows:

2,500 mg of abiraterone decanoate was weighed and placed in a 20-mL serum vial with a crimped stopper. 60 mL of a 70% corn oil/10% benzyl alcohol/20% benzyl benzoate mixture was placed in a separate 100-mL serum vial with a crimped stopper. The vehicle vial was then wrapped in aluminum foil and sterilized in an autoclave using a 30-minute liquid cycle. Following sterilization, the vials were moved to a laminar flow hood. Then, 10 mL of the sterile 70% corn oil/10% benzyl alcohol/20% benzyl benzoate solution was removed and added to the abiraterone decanoate and the vial was re-stoppered and crimped closed. The abiraterone decanoate was then dissolved by sonicating, vortexing, and placing the vials on a rotator. The final concentration of the sterile solution of abiraterone decanoate was 209 mg/ml.

Example 3I. Preparation of Abiraterone Decanoate (~240 mg/ml) 70% Corn Oil, 10% Benzyl Alcohol, 20% Benzyl Benzoate Solution An abiraterone decanoate injectable (IM depot ~240 mg/ml) 70% corn oil, 10% benzyl alcohol, 20% benzyl benzoate solution was prepared as follows:

3,125 mg of abiraterone decanoate was weighed and placed in a 20-mL serum vial with a crimped stopper. 60 mL of a 70% corn oil/10% benzyl alcohol/20% benzyl benzoate mixture was placed in a separate 100-mL serum vial with a crimped stopper. The vehicle vial was then wrapped in aluminum foil and sterilized in an autoclave using a 30-minute liquid cycle. Following sterilization, the vials were moved to a laminar flow hood. Then, 10 mL of the sterile 70% corn oil/10% benzyl alcohol/20% benzyl benzoate solution was removed and added to the abiraterone decanoate and the vial was re-stoppered and crimped closed. The abiraterone decanoate was then dissolved by sonicating, vortexing, and placing the vials on a rotator. The final concentration of the sterile solution of abiraterone decanoate was 242 mg/ml.

Example 3J. Preparation of Abiraterone Isocaproate 90% Corn Oil, 10% Benzyl Alcohol Solution An abiraterone isocaproate injectable (IM depot) 90% corn oil, 10% benzyl alcohol solution was prepared as follows:

1190 mg of abiraterone isocaproate was weighed and placed in a 10-mL serum vial with a crimped stopper. 8 mL of a 90% corn oil/10% benzyl alcohol mixture was placed in a separate 10-mL serum vial with a crimped stopper. The vehicle vial was then wrapped in aluminum foil and sterilized in an autoclave using a 30-minute liquid cycle. Following sterilization, the vials were moved to a laminar flow hood. Then, 6.4 mL of the sterile 90% corn oil/10% benzyl alcohol solution was removed and added to the abiraterone isocaproate and the vial was re-stoppered and crimped closed. The abiraterone isocaproate was then dissolved by sonicating, vortexing, and placing the vials on a rotator. The final concentration of the sterile solution of abiraterone isocaproate was 158 mg/ml.

Example 4A. Solubility Testing of Abiraterone Prodrugs

The solubilities of various abiraterone prodrugs were tested as follows. The results are shown in Table 2.

For each solvent studied, a sufficient quantity of prodrug was weighed into a separate glass vial and 1-2 ml of solvent was added. The resultant suspension was sonicated and vortexed. If the prodrug was completely dissolved, more prodrug was added until an excess of material was observed. If there was a large excess of undissolved prodrug, additional diluent could be added. The total mass and volume used were recorded. Each vial was tightly capped and wrapped with foil to protect it from light as necessary. The vials were placed on a laboratory rotator in a 25° C. incubator (or at any other temperature that was required). The samples were allowed to equilibrate for a minimum of 1 day before assessing solubility. A later second time point, typically at about 1 week, was also taken to confirm the solubility of each prodrug.

At the appropriate time point, the vials were removed from the incubator. A small amount of supernatant from each vial was transferred into a microcentrifuge tube containing a 0.22 or 0.45 um filter. The tube was centrifuged at 10,000 rpm until all of the liquid passed through the filter to the bottom of the tube. Alternatively, samples were filtered using a 0.22 or 0.45 μm syringe filter. The filtered liquid was assayed using HPLC. Samples were diluted as necessary so that the sample concentrations were bracketed by the standards.

TABLE 2

Solubilities of Abiraterone Prodrugs.

| Vehicle | Abiraterone Prodrug Solubility (mg/ml) | | | |
| --- | --- | --- | --- | --- |
| | Acetate | Propionate | Butanoate | Decanoate |
| Castor oil | 74 | 154 | 36 | 188 |
| Castor oil, 10% benzyl alcohol | 112 | 188 | 52 | 190 |
| Castor oil, 10% benzyl benzoate | 91 | — | — | — |
| Castor oil, 50% benzyl benzoate | 148 | — | — | — |
| Sesame oil | 27 | 86 | 17 | 130 |
| Cottonseed oil | 27 | 85 | 17 | 152 |

TABLE 2-continued

Solubilities of Abiraterone Prodrugs.

| Corn oil | 56 | 134 | 30 | 183 |
| Corn oil, 10% benzyl alcohol | — | 223 | — | 277 |

| | Abiraterone Prodrug Solubility (mg/ml) | | | | |
| --- | --- | --- | --- | --- | --- |
| Vehicle | Cypionate | Isocaproate | Heptanoate | Hexanoate | Pentanoate |
| Castor oil | 48 | 120 | 124 | 173 | 89 |
| Castor oil, 10% benzyl alcohol | 108 | 160 | 171 | 188 | 121 |
| Corn oil | 70 | 103 | 124 | 133 | 81 |
| Corn oil, 10% benzyl alcohol | 121 | 183 | 189 | 204 | 146 |

The parenteral formulations must be sterilized before administration. This can be achieved by a variety of techniques including heat sterilization (for example, dry heat or moist heat), radiation sterilization (for example, gamma ray sterilization), filtration sterilization (for example, 0.22 micrometer membrane filters), or gaseous sterilization (for example, formaldehyde or ethylene oxide gas).

Example 4B. Solubility, Viscosity, and Glide Force Testings of Abiraterone Decanoate Formulations or Oil Vehicles This example tests properties of various abiraterone decanoate formulations and oil vehicles.

First, further solubility studies show solubility advantages of abiraterone decanoate formulation 70% Corn oil, 10% benzyl alcohol, 20% benzyl Benzoate. See Table 2A below. The abiraterone decanoate used for the studies in Table 2A was obtained from Example 6A.

TABLE 2A

Solubility Studies of Abiraterone Decanoate in Different Vehicles

| Formulation | | | Equilibrium saturation solubility |
| --- | --- | --- | --- |
| Corn Oil | Benzyl Alcohol | Benzyl Benzoate | (RT, mg/ml) |
| 100% | — | — | 63 |
| 90% | — | 10% | 79 |
| 80% | — | 20% | 94 |
| 95% | 5% | — | 108 |
| 90% | 10% | — | 170 |
| 85% | 5% | 10% | 148 |
| 70% | 10% | 20% | 240 |

As can be seen from this study, the combination of benzyl alcohol and benzyl benzoate can significantly enhance the solubility of abiraterone decanoate in corn oil. See also FIGS. 13A and 13B.

Additional experiments also show that the inclusion of benzyl benzoate lowers viscosity and Glide Force of oil vehicles. It is expected that such oil vehicles can be advantageously used in formulating the abiraterone prodrugs herein to provide a lower viscosity and lower Glide Force abiraterone prodrug formulation when desired.

The Glide Force testing was carried out with tensile and compression testing machine (e.g. Lloyd press or equivalent), NEXYGEN Plus materials testing software, or equivalent Load cell 250N. 5-mL Luer-Lok Syringe (e.g. Becton, Dickinson and Company/BD, P/N 309646), or equivalent 23 gauge, 1.5 inch length, thin wall, Precision Glide Needle (e.g. Becton, Dickinson and Company/BD, P/N 305194), or equivalent 27 gauge, 1.5 inch length, regular wall, Precision Glide Needle (e.g. Becton, Dickinson and Company/BD, P/N 301629), or equivalent.

Table 2B shows the viscosity of various oil vehicles, without additives, or with 10% benzyl alcohol, 20% benzyl benzoate, or a combination of 10% benzyl alcohol and 20% benzyl benzoate. See also FIG. 13C.

TABLE 2B

Viscosity (Pa*s) of Various Oils with Additives

| Solvent | None | 10% Benzyl Alcohol | 20% Benzyl Benzoate | 20% Benzyl Benzoate with 10% Benzyl alcohol |
| --- | --- | --- | --- | --- |
| Corn Oil | 0.0550 | 0.0386 | 0.0371 | 0.0267 |
| Sesame Oil | 0.0594 | 0.0409 | 0.0395 | 0.0277 |
| Peanut Oil | 0.0671 | 0.0458 | 0.0434 | 0.0302 |
| Cottonseed Oil | 0.0591 | 0.0408 | 0.0396 | 0.0280 |
| Miglyol 812 | 0.0259 | 0.0193 | 0.0204 | 0.0154 |

Tables 2C and 2D show Glide Force (N) of various oil vehicles, without additives, or with 10% benzyl alcohol, 20% benzyl benzoate, or a combination of 10% benzyl alcohol and 20% benzyl benzoate, using 23 Gauge Needle or 27 Gauge Needle, respectively. See also FIGS. 13D and 13E.

TABLE 2C

Glide Force (N) of Various Oils with Additives, 23 Gauge Needle

| Solvent | None | 10% Benzyl Alcohol | 20% Benzyl Benzoate | 20% Benzyl Benzoate with 10% Benzyl alcohol |
| --- | --- | --- | --- | --- |
| Corn Oil | 13.4 | 8.7 | 8.0 | 7.5 |
| Sesame Oil | 12.4 | 9.7 | 8.7 | 6.1 |
| Peanut Oil | 14.6 | 12.9 | 10.9 | 6.6 |
| Cottonseed Oil | 11.9 | 10.8 | 10.1 | 5.7 |
| Miglyol 812 | 12.4 | 6.7 | 6.5 | 4.1 |

TABLE 2D

Glide Force (N) of Various Oils with Additives, 27 Gauge Needle

| Solvent | None | 10% Benzyl Alcohol | 20% Benzyl Benzoate | 20% Benzyl Benzoate with 10% Benzyl alcohol |
|---|---|---|---|---|
| Corn Oil | 91.5 | 66.4 | 53.0 | 48.5 |
| Sesame Oil | 92.6 | 68.0 | 63.2 | 46.1 |
| Peanut Oil | 85.6 | 74.0 | 58.2 | 49.2 |
| Cottonseed Oil | 99.3 | 68.4 | 63.8 | 45.0 |
| Miglyol 812 | 46.8 | 35.4 | 37.7 | 27.2 |

Example 5

Blood Plasma Pharmacokinetics of Abiraterone in Rats and Dogs Following Administration of Formulations of Abiraterone Prodrugs

Example 5A. PK Studies of Abiraterone and Abiraterone Acetate in Rats and Dogs Several formulations were considered in the initial rat study. These formulations consisted of abiraterone acetate as a solution in castor oil or as a suspension in sodium phosphate buffer, 0.1% Tween and abiraterone suspension in castor oil or as an aqueous mixture of sodium phosphate buffer, 0.1% Tween. The manufacturing of these long-acting IM formulations follows the general process of placing the drug in one vial and the solubilizing solution in a second vial and sterilizing each of the vials. Once the components are sterilized, they are mixed together under sterile conditions to produce the final product. Sterilization is done separately because the drug could possibly degrade during the sterilization process when the drug is in solution. Additionally, this sterilization process was selected over filtration sterilization due to the viscosity of the oils or the suspension nature of two of the formulations.

An additional study was done using dogs as the animal model instead of rats. Four formulations were taken into this study and they included a solution of abiraterone acetate in an aqueous system (given IV) and solutions of abiraterone acetate in castor, 90% castor oil and 10% benzyl alcohol, or abiraterone acetate in 50% castor oil and 50% benzyl benzoate.

The above formulations were administered to either rats or dogs as an IV injection or as IM injections to the hind leg(s) of each animal. Plasma samples were pulled throughout the length of the study and analyzed for both prodrug and abiraterone. The results of the rat study are provided in Table 3 and FIG. 1.

TABLE 3

Group Mean Plasma Pharmacokinetic Parameters for Abiraterone Following IM Injection of Various Formulations of Abiraterone or Abiraterone Acetate in Rats.

| Group | Animal | $T_{max}$ (hr) | $C_{max}$ (ng/mL) | $AUC_{last}$ (ng*hr/mL) |
|---|---|---|---|---|
| 1 | N | 5 | 5 | 5 |
|  | Mean | 39.2 | 21.6 | 934 |
|  | SD | 35.3 | 26.1 | 332 |
|  | CV % | 90.2 | 121 | 35.5 |

TABLE 3-continued

Group Mean Plasma Pharmacokinetic Parameters for Abiraterone Following IM Injection of Various Formulations of Abiraterone or Abiraterone Acetate in Rats.

| Group | Animal | $T_{max}$ (hr) | $C_{max}$ (ng/mL) | $AUC_{last}$ (ng*hr/mL) |
|---|---|---|---|---|
| 2 | N | 5 | 5 | 5 |
|  | Mean | 8.00 | 3.84 | 329 |
|  | SD | 0.00 | 2.40 | 71.6 |
|  | CV % | 0.00 | 62.6 | 21.8 |
| 3 | N | 5 | 5 | 4 |
|  | Mean | 2.60 | 13.3 | 163 |
|  | SD | 1.34 | 16.0 | 174 |
|  | CV % | 51.6 | 120 | 107 |
| 4 | N | 3 | 3 | 0 |
|  | Mean | 1.67 | 1.43 |  |
|  | SD | 0.577 | 0.261 |  |

Group 1: abiraterone acetate solution in castor oil (70 mg/ml);
Group 2: abiraterone acetate suspension, sodium phosphate buffer, 0.1% Tween (70 mg/ml);
Group 3: abiraterone suspension in castor oil (62.5 mg/ml);
Group 4: abiraterone suspension, sodium phosphate buffer, 0.1% Tween (62.5 mg/ml)

The data from the rat study indicate that formulations containing abiraterone acetate preformed significantly better than the formulations containing abiraterone. Additionally, the formulation of Group 1, which contained abiraterone acetate in solution, performed better than the formulation of Group 2, which contained abiraterone acetate in suspension versus solution.

FIG. 1 depicts the mean plasma concentrations versus time profiles of abiraterone in rats following IM injection of the abiraterone acetate formulation into the thigh muscle of five male rats at a dose of 35 mg/kg. Blood samples for the evaluation of systemic exposure after abiraterone acetate IM depot administration were collected at 1, 2, 4, 8, 24, 48, 72 and 168 hours post-administration and analyzed for abiraterone as well as abiraterone acetate. In this study, the abiraterone acetate castor oil solution formulation was compared with abiraterone acetate aqueous suspension formulation and abiraterone aqueous and castor oil suspensions.

Initially, we attempted to administer abiraterone intramuscularly to rats as a suspension consisting of vegetable oils and aqueous. Surprisingly, very low blood plasma levels were achieved with abiraterone itself (See FIG. 1). Also, surprisingly, the use of abiraterone acetate in aqueous suspension resulted in low blood plasma levels (See FIG. 1). Conversely, a vegetable oil solution of abiraterone acetate gave not only the highest blood plasma levels but also the longest extended blood plasma concentrations of abiraterone in rats when injected intramuscularly (See FIG. 1).

The abiraterone acetate castor oil IM depot solution formulation showed superior plasma concentrations of abiraterone compared with the abiraterone and abiraterone acetate aqueous and castor oil suspensions over the 168-hour period.

Figure 2:
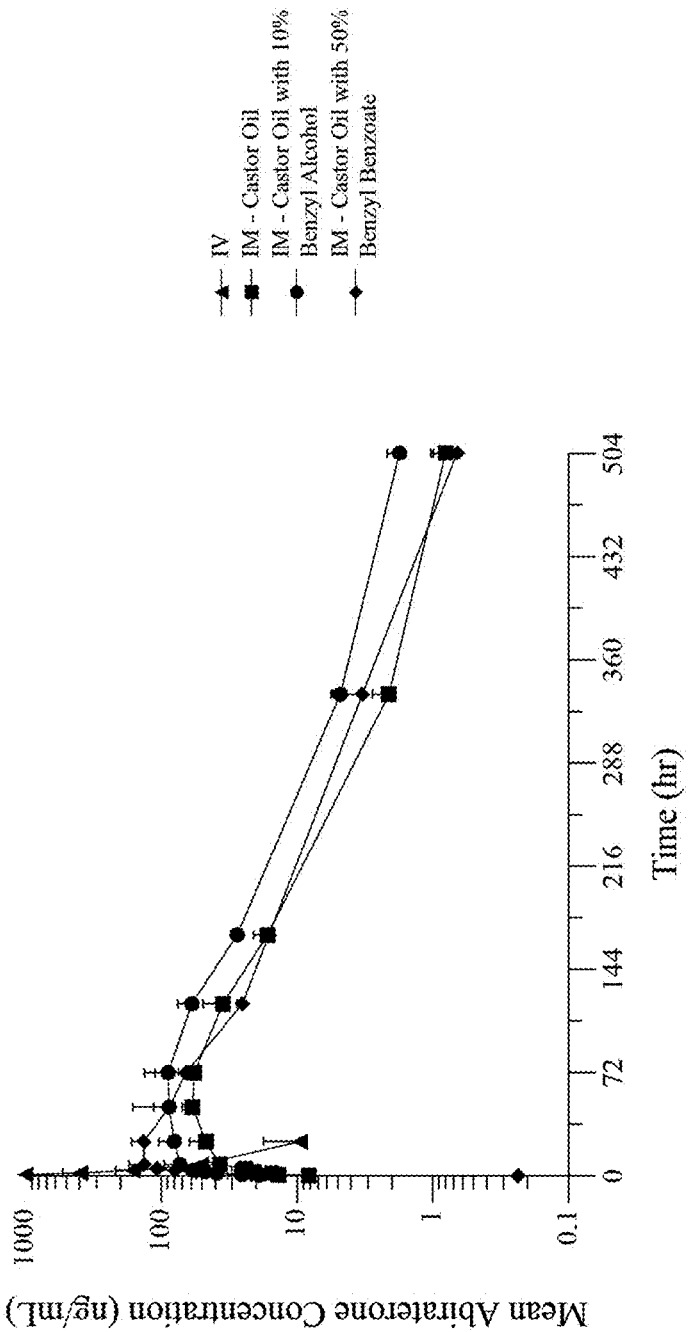
FIG. 2 shows the mean blood plasma concentrations of abiraterone (ng/ml) in dogs at different times (hours) after IM or intravenous (IV) administration of various abiraterone acetate formulations.
Figure 3:
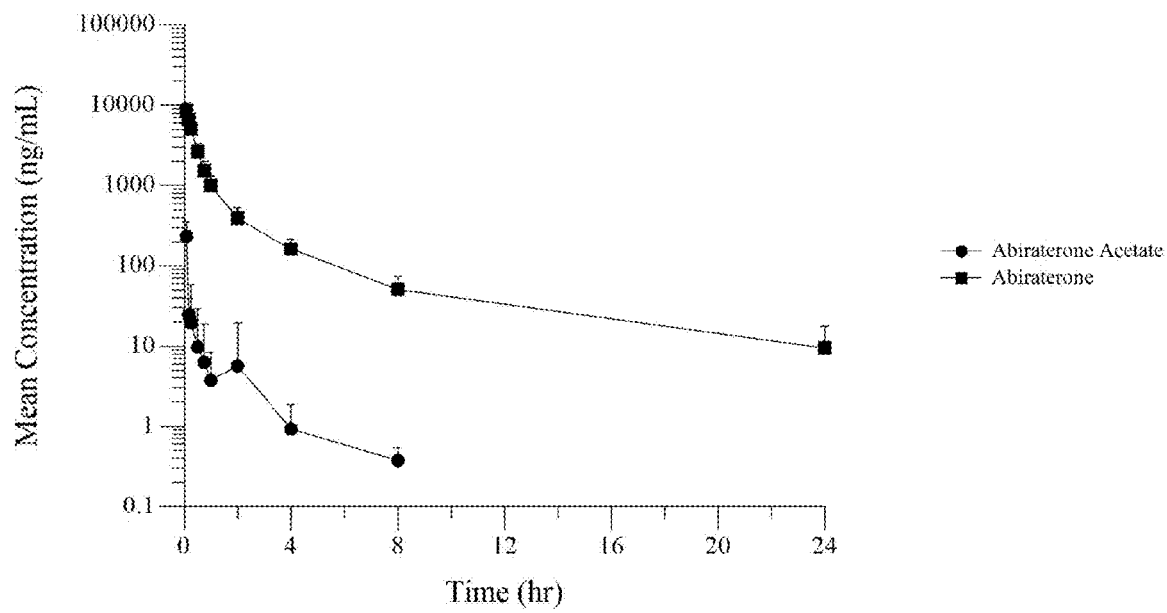
FIG. 3 shows the mean blood plasma concentrations of abiraterone (top line) and abiraterone acetate (bottom line) (ng/ml) in dogs at different times (hours) after IV administration of abiraterone acetate (dosed at 10.3 mg/ml as a solution in 33% aqueous HP-beta-cyclodextrin).
Figure 4:
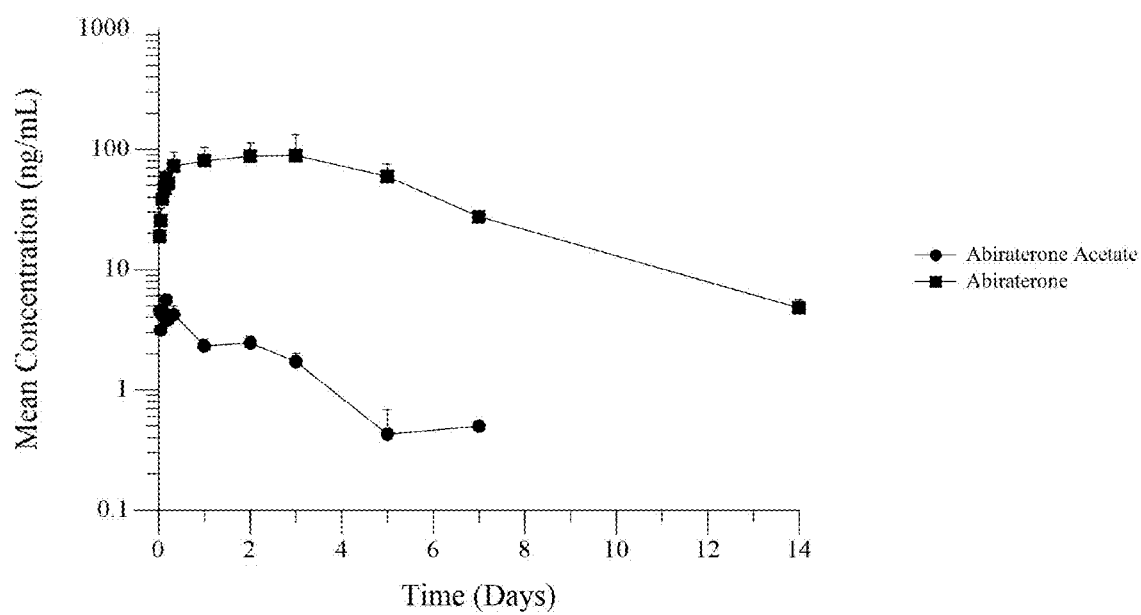
FIG. 4 shows the mean blood plasma concentration of abiraterone (top line) and abiraterone acetate (bottom line) (ng/nl) in dogs at different times (days) after IM administration of abiraterone acetate solution in castor oil with 10% benzyl alcohol (91 mg/ml) dosed at 30 mg/kg.
Figure 5:
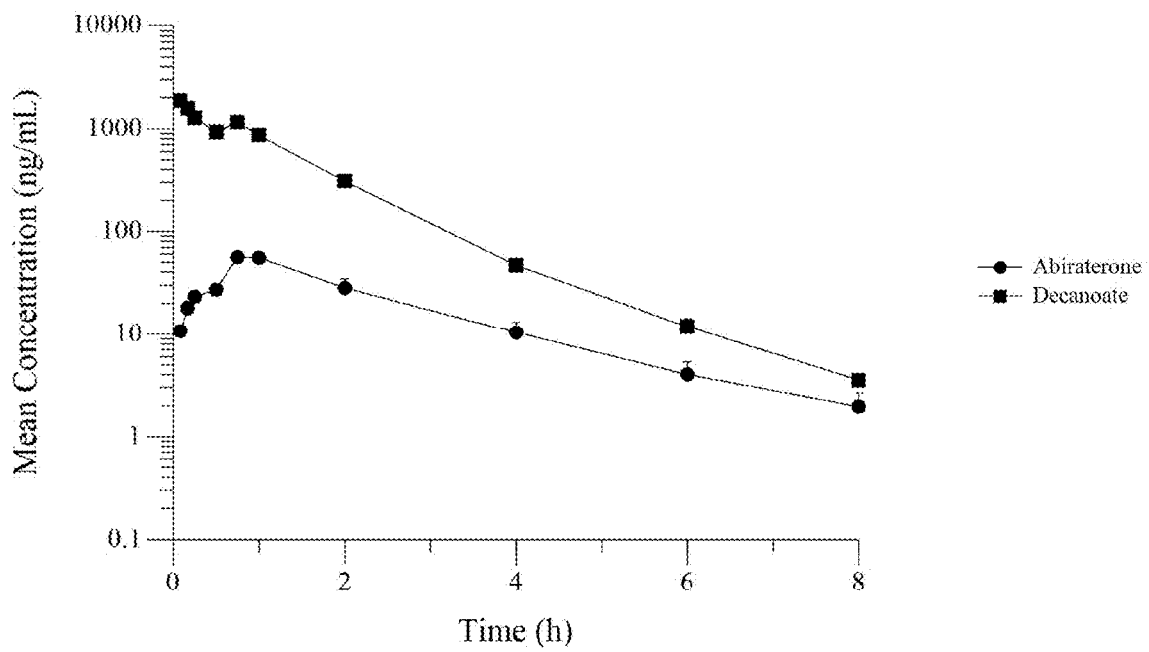
FIG. 5 shows mean abiraterone and abiraterone decanoate plasma concentration versus time profile data following IV administration of 1.2 mg/kg abiraterone decanoate in dogs. Error bars represent standard deviation.
Figure 6:
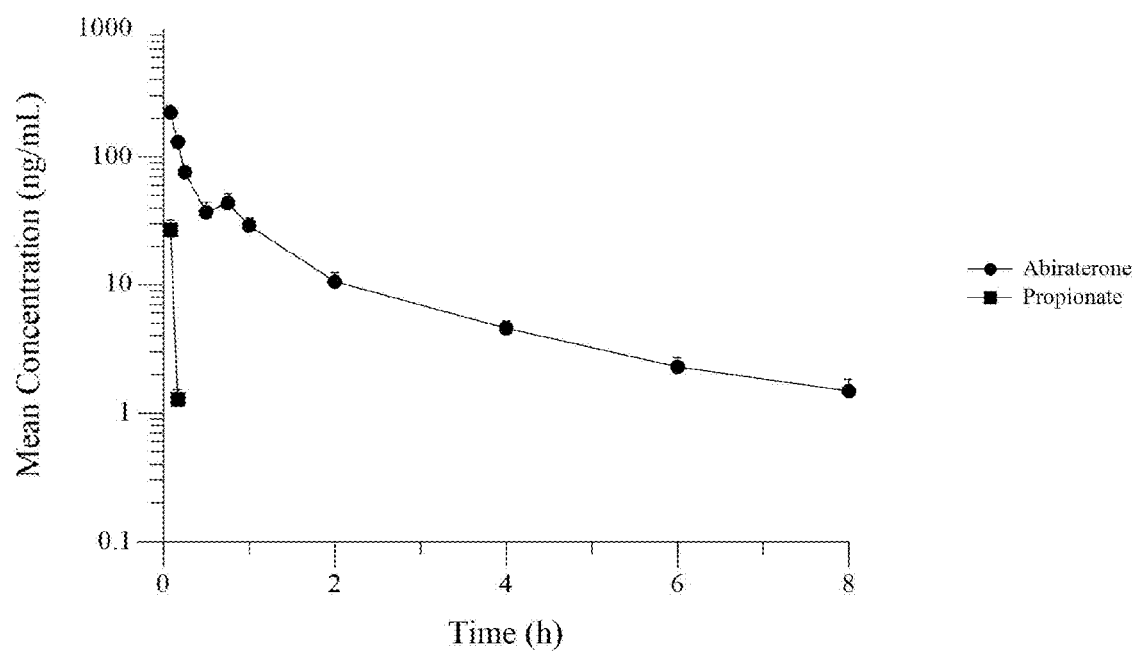
FIG. 6 shows mean abiraterone and abiraterone propionate plasma concentration versus time profile data following IV administration of 1 mg/kg abiraterone propionate in dogs. Error bars represent standard deviation.
Figure 7:
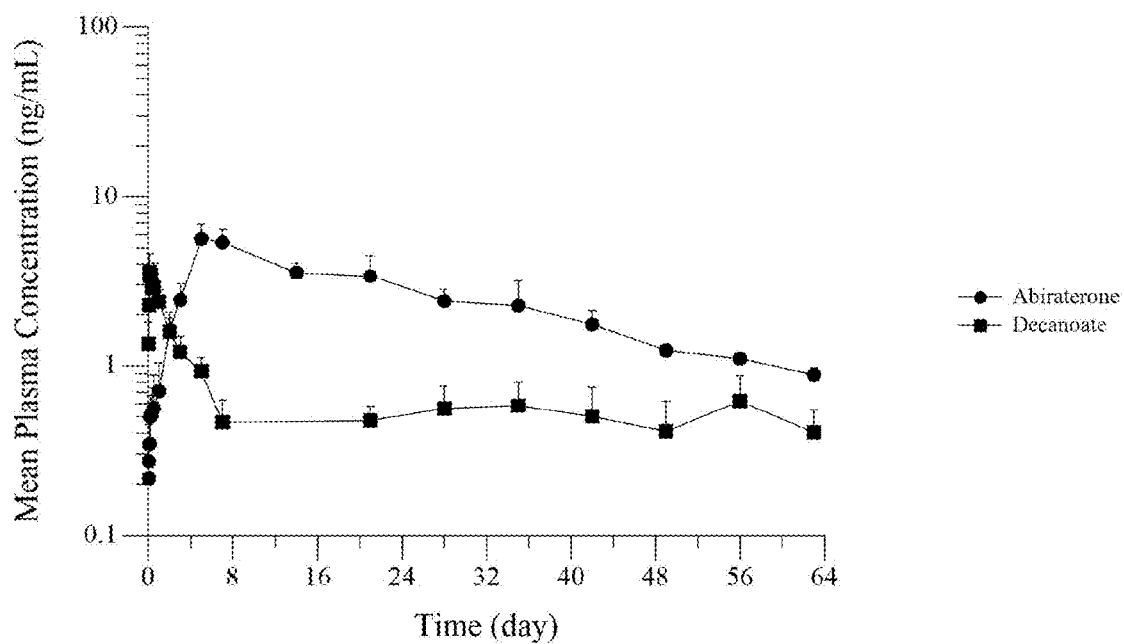
FIG. 7 shows mean abiraterone and abiraterone decanoate plasma concentration versus time profile data following IM Administration of 50 mg/kg abiraterone decanoate (90% castor oil/10% benzyl alcohol) in dogs. Error bars represent standard deviation.
Figure 8:
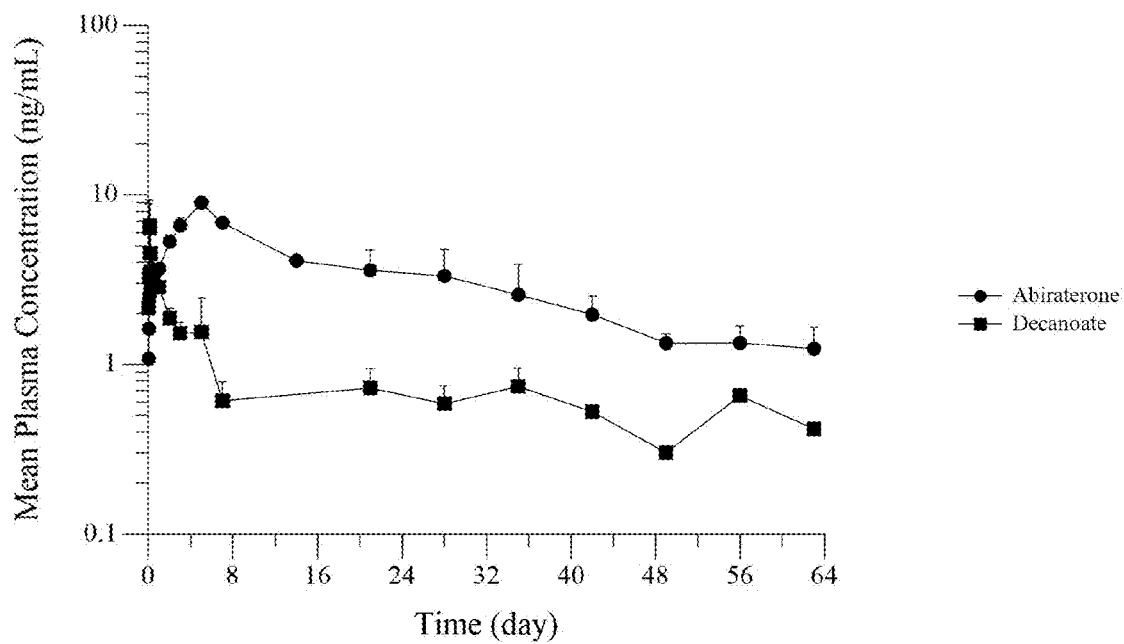
FIG. 8 shows mean abiraterone and abiraterone decanoate plasma concentration versus time profile data following IM Administration of 50 mg/kg abiraterone decanoate (90% corn oil/10% benzyl alcohol) in dogs. Error bars represent standard deviation.
Figure 9:
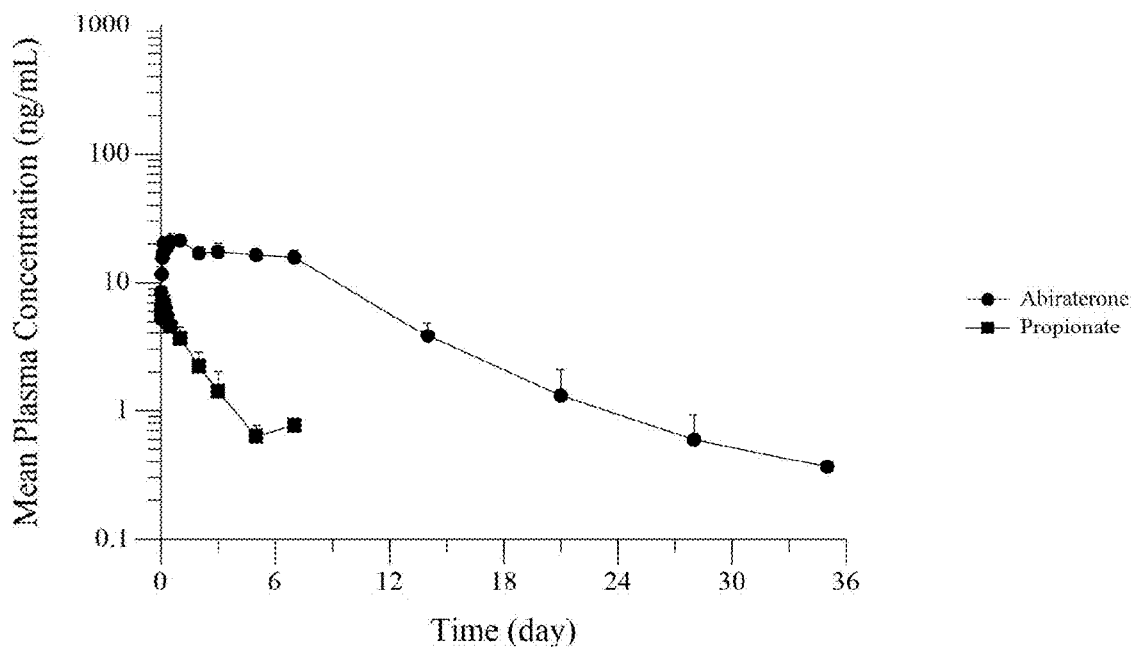
FIG. 9 shows mean abiraterone and abiraterone propionate plasma concentration versus time profile data following IM administration of 41 mg/kg abiraterone propionate (90% castor oil/10% benzyl alcohol) in dogs. Error bars represent standard deviation.
Figure 10:
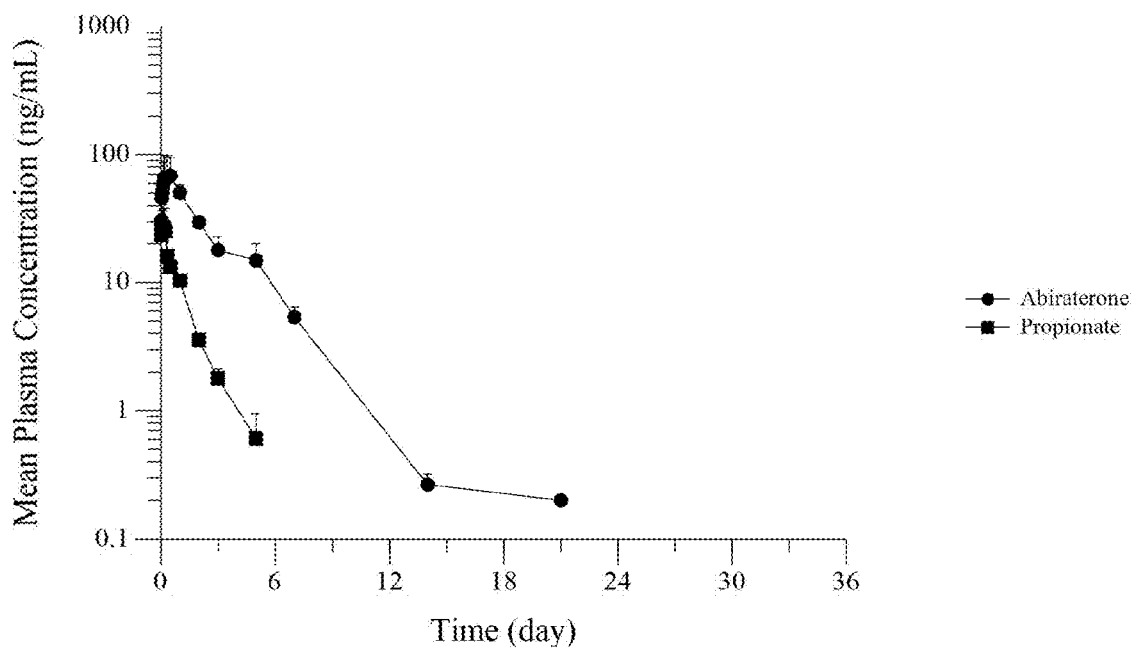
FIG. 10 shows mean abiraterone and abiraterone propionate plasma concentration versus time profile data following IM administration of 41 mg/kg abiraterone propionate (90% corn oil/10% benzyl alcohol) in dogs. Error bars represent standard deviation.
Figure 11A:
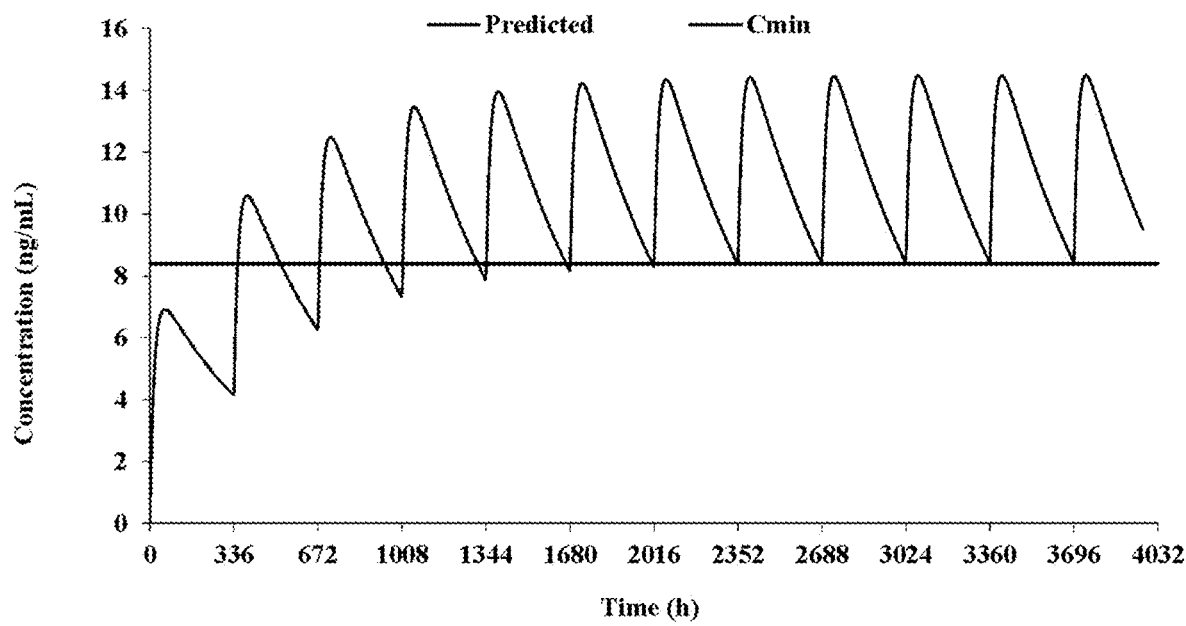
FIG. 11A, FIG. 11B, FIG. 11C, and FIG. 11D show exemplary predicted human abiraterone plasma concentrations following intramuscular administration of abiraterone decanoate by computer modeling in human, using an input half-life assumed to be the same as that observed in dog.
Figure 11B:
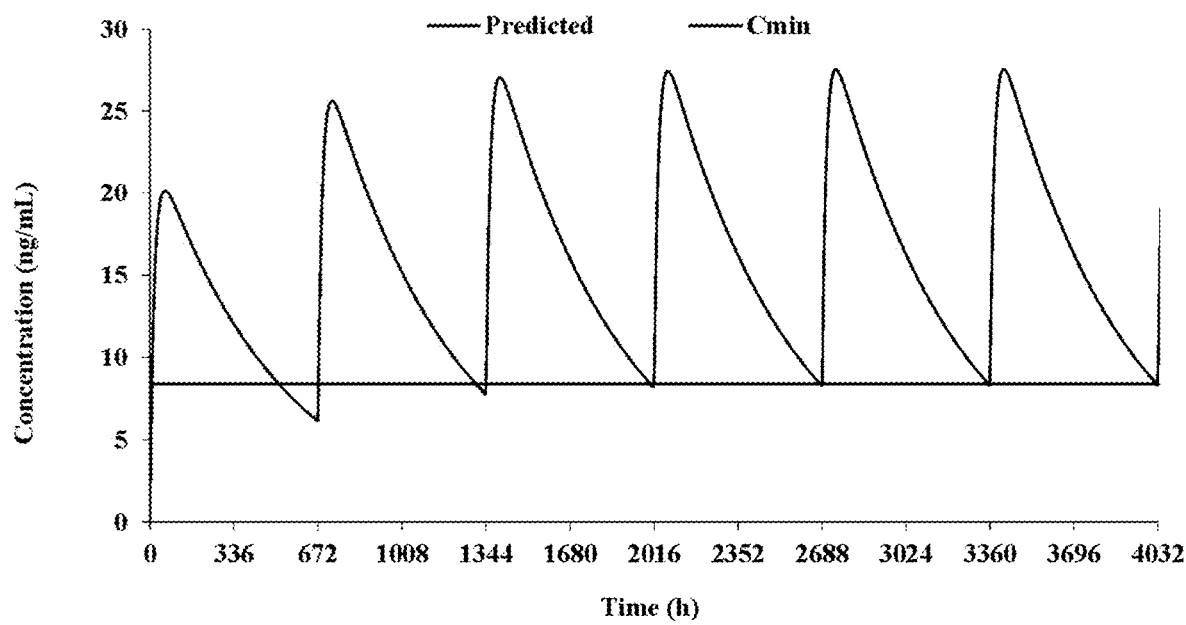
Figure 11C:
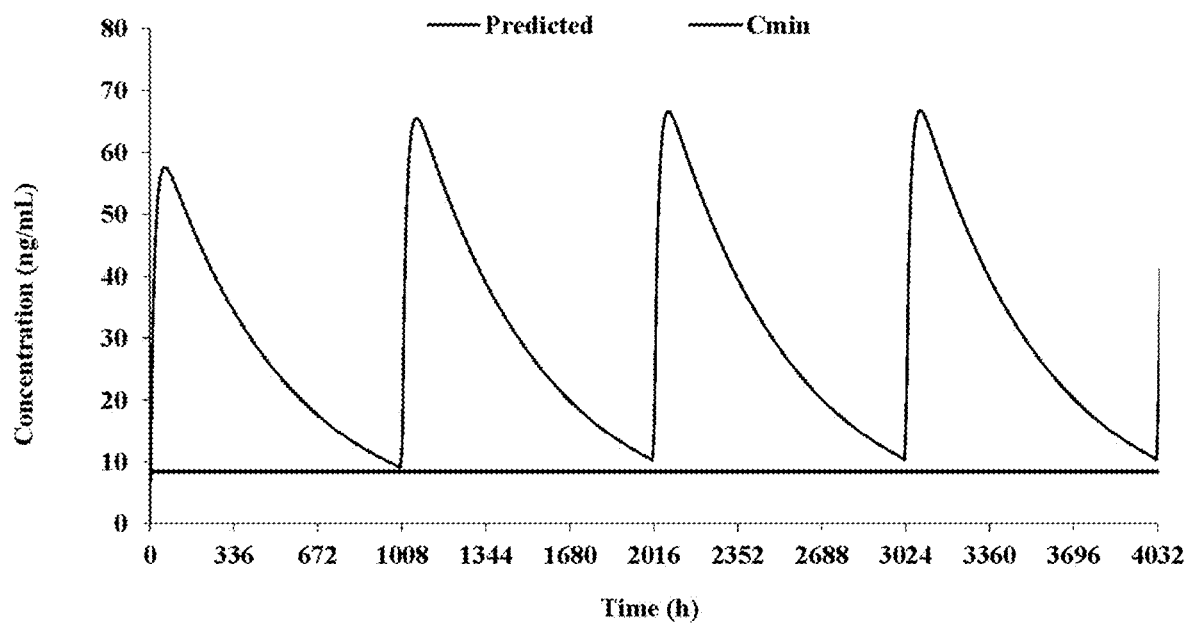
Figure 11D:
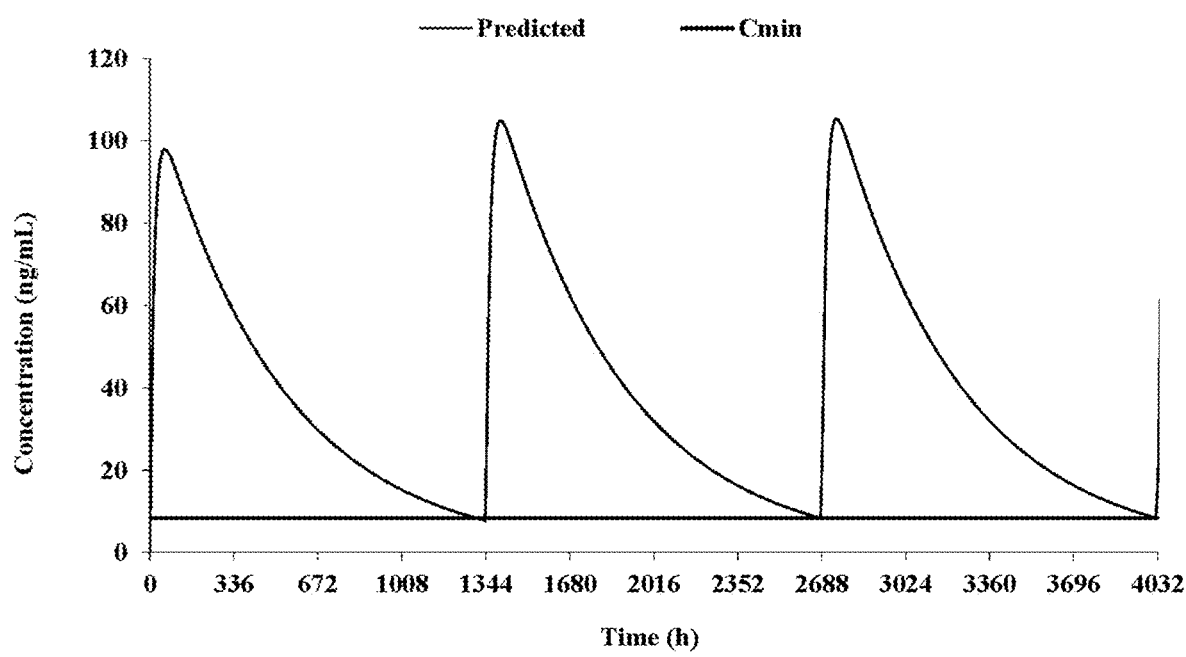

The results of the dog study are provided in Table 4 and FIG. 2.

TABLE 4

Group Mean Plasma Pharmacokinetic Parameters for
Abiraterone Following IV and IM Injection of Abiraterone Acetate in Dogs.

| Group | Dose (mg/kg) | Animal | $T_{max}$ (hr) | $C_{max}$ (ng/ml) | $C_{max}$/ Dose | $AUC_{last}$ (hr * ng/mL) | $AUC_{last}$/ Dose | $AUC_{INF}$ (hr * ng/mL) | $AUC_{INF}$/ Dose | $t_{1/2}$ (hr) | % F |
|---|---|---|---|---|---|---|---|---|---|---|---|
| 1 | 10 | N | 9 | 9 | 9 | 9 | 9 | 9 | 9 | 9 | |
| | | Mean | 0.0830 | 8560 | 856 | 5920 | 592 | 5990 | 599 | 4.64 | |
| | | SD | 0.00 | 2170 | 217 | 1590 | 159 | 1630 | 163 | 1.33 | |
| | | CV % | 0.00 | 25.4 | 25.4 | 26.9 | 26.9 | 27.3 | 27.3 | 28.6 | |
| 2 | 19 | N | 3 | 3 | 3 | 3 | 3 | 3 | 3 | 3 | 3 |
| | | Mean | 56.0 | 60.6 | 2.89 | 8910 | 469 | 8990 | 473 | 78.4 | 86.2 |
| | | SD | 13.9 | 14.4 | 0.684 | 1830 | 96.3 | 1790 | 94.2 | 10.2 | 9.58 |
| | | CV % | 24.7 | 23.7 | 23.7 | 20.5 | 20.5 | 19.9 | 19.92 | 13.1 | 11.1 |
| 3 | 27 | N | 3 | 3 | 3 | 3 | 3 | 3 | 3 | 3 | 3 |
| | | Mean | 56.0 | 97.7 | 3.26 | 14900 | 551 | 15000 | 555 | 87.3 | 85.7 |
| | | SD | 13.9 | 39.2 | 1.45 | 3940 | 146 | 3940 | 146 | 3.73 | 2.11 |
| | | CV % | 24.7 | 40.1 | 40.1 | 26.5 | 26.5 | 26.3 | 26.3 | 4.27 | 2.46 |
| 4 | 38 | N | 3 | 3 | 3 | 3 | 3 | 3 | 3 | 3 | 3 |
| | | Mean | 21.3 | 153 | 4.04 | 12400 | 327 | 12500 | 329 | 66.0 | 61.7 |
| | | SD | 23.1 | 33.5 | 0.882 | 3350 | 88.2 | 3370 | 88.6 | 13.4 | 28.8 |
| | | CV % | 108 | 21.8 | 21.8 | 26.9 | 26.9 | 27.0 | 27.0 | 20.2 | 46.7 |

Group 1: IV administration of abiraterone acetate solution (33% aq HP-beta-cyclodextrin) dosed at 10 mg/kg;
Group 2: IM administration of abiraterone acetate solution in castor oil (66 mg/ml) dosed at 21 mg/kg;
Group 3: IM administration of abiraterone acetate solution in castor oil with 10% benzyl alcohol (91 mg/ml) dosed at 30 mg/kg;
Group 4: IM administration of abiraterone acetate solution in castor oil with 50% benzyl benzoate (124 mg/ml) dosed at 42 mg/kg.

The data from the dog study indicate that abiraterone acetate given as a solution in castor oil (with or without benzyl alcohol) produced measurable blood levels out to 504 hours. Additionally, although the formulation with benzyl benzoate produced measurable levels of abiraterone acetate, the formulation was found to be irritating to the dogs at the injection site; one or two dogs were licking and biting at the injection site and developed an open wound. This caused a significant decrease in the fraction of prodrug absorbed from these animals and a significant decrease in the average fraction absorbed (61.7%) in this dose group. The absolute bioavailabities for these formulations were found to range between 61.7 and 86.2%.

FIG. 2 depicts the mean plasma concentrations versus time profiles of abiraterone in dogs following IM injection of various abiraterone acetate formulations into the thigh muscle of male dogs (three dogs for each formulation) at doses of 19, 27, and 38 mg/kg. Blood samples for the evaluation of systemic exposure after abiraterone acetate IM depot administration were collected at 0.5, 1, 2, 3, 4, 5, 8, 24, 48, 60, 120, 168, 336, and 504 hours post-administration and analyzed for abiraterone as well as abiraterone acetate.

The abiraterone acetate IM depot solution formulations in castor oil, castor oil/benzyl alcohol, and castor oil/benzyl benzoate showed extended plasma concentrations of abiraterone over the 504-hour period.

An IV administration of abiraterone acetate was included in this study (dose of 10 mg/kg) to measure the bioavailability of the IM depot formulations. The bioavailabilies were determined to be 86.2%; 85.7% and 61.7%.

Computer-modeling was used to predict the human pharmacokinetic profile of abiraterone prodrugs administered IM to humans based on data obtained from the IM rat and dog studies. The modeling predicted that an IM dose of 600 mg to 2,000 mg of abiraterone acetate administered to human subjects every two to four weeks would produce the desired plasma pharmacokinetic profile in human subjects (that is, bioavailability of greater than 80%, $C_{min}$ value of abiraterone greater than 1.0 ng/ml to 8.4 ng/ml, e.g., greater than 1 ng/ml, greater than 2 ng/ml, greater than 4 ng/ml, or greater than 8.4 ng/ml, and $C_{max}$ value of abiraterone of approximately 10 ng/ml to 400 ng/ml for at least two weeks). The predicted 600 mg IM dose of abiraterone acetate administered every two weeks should be compared to the current 1,000 mg/day oral dose of Zytiga® (which would be 14,000 mg for a two-week dosing period). The higher bioavailability of the IM delivery together with the elimination of the food effect will lead to lower patient variability which together with higher and less frequent plasma trough levels should lead to better efficacy (ref $C_{min}$>8.4 ng/ml associated with improved prostate-specific antigen response and improved progression-free survival in castration-resistant prostate cancer patients) (Carton et al., *Eur. J. Can.* 72:54, 2017).

Example 5B. PK Studies of Abiraterone Propionate and Abiraterone Decanoate in Dogs This is a Single-Dose Bioavailability Study of Several Abiraterone Pro-drugs (Propionate and Decanoate) given as Intramuscular Injections (IM) and intravenous injections to Beagle Dogs.

The formulations and dosages used for this study are as follows:

1) Intramuscular (IM); Abiraterone propionate 197 mg/mL solution in 10% Benzyl alcohol/90% Castor oil, dosed at 41 mg/kg;
2) Intramuscular (IM); Abiraterone propionate 168 mg/mL solution in 10% Benzyl alcohol/90% Corn oil, dosed at 41 mg/kg;
3) Intramuscular (IM); Abiraterone decanoate 160 mg/mL solution in 10% Benzyl alcohol/90% Castor oil; dosed at 50 mg/kg;
4) Intramuscular (IM); Abiraterone decanoate 170 mg/mL solution in 10% Benzyl alcohol/90% Corn oil; dosed at 50 mg/kg;
5) Intravenous (IV); Abiraterone propionate 0.57 mg/mL solution in 40% HP-b-CD/25 mM Na phosphate (pH 7.4) dosed at 1 mg/kg; and
6) Intravenous (IV); Abiraterone decanoate 0.37 mg/mL solution in 40% HP-b-CD/25 mM Na phosphate (pH 7.4), dosed at 1.2 mg/kg.

Table 5 below summarizes the study design:

TABLE 5

Experimental Study Design

| Group | Test Article | Route | Dose Level (mg/kg)* | Dose Conc. (mg/mL) | # of Animals |
|---|---|---|---|---|---|
| 1 | Abiraterone Propionate in 40% HP-beta-cyclodextrin | IV | 1 | 0.57 | 6 |
| 2 | Abiraterone Decanoate in 40% HP-beta-cyclodextrin | IV | 1.2 | 0.37 | 6 |
| 3 | Abiraterone Propionate in 90% castor oil/10% benzyl alcohol | IM | 41 | 197 | 3 |
| 4 | Abiraterone Propionate in 90% corn oil/10% benzyl alcohol | IM | 41 | 168 | 3 |
| 5 | Abiraterone Decanoate in 90% castor oil/10% benzyl alcohol | IM | 50 | 160 | 3 |
| 6 | Abiraterone Decanoate in 90% corn oil/10% benzyl alcohol | IM | 50 | 170 | 3 |

*dose is Pro-drug concentration.
Equivalent Abiraterone active dose was 0.82 mg/kg for IV administration and 35 mg/kg for IM administration All animals were dose via IV administration. Following a washout period of 72 hours, all dogs were dosed via IM route. Doses were based on an assumed body weight of 10 kg. Following IV administration, blood was collected at 0.083, 0.1667, 0.25, 0.5, 0.75, 1, 2, 4, 6, 8, and 24 hours post dose administration. Following IM administration, blood was collected at 0.5, 1, 2, 3, 4, 5, 8, and 12 hours and 1, 2, 3, 5, 7, 14, 21, 28, 35, 42, 49, 56 (decanoate only) and 63 (decanoate only) days post dose administration (time of collection to approximate the time of dose administration). Blood was processed to plasma and the resulting plasma samples were analyzed for the prodrug and abiraterone.

Following IV administration of abiraterone propionate, animals only had 1 or 2 quantifiable plasma concentrations, as such, no reliable pharmacokinetic parameters could be assessed.

Pharmacokinetic analyses were performed on plasma concentration versus time data using Phoenix WinNonlin (v 8.1) non-compartmental analysis function (linear trapezoidal rule for AUC calculations). Nominal dose values and sampling times were used for calculations. For the purpose of PK calculations, any concentration reported as "BLQ" was set equal to zero.

$C_{max}$ and the corresponding $T_{max}$ values were determined by direct assessment of the concentration versus time data. All AUC calculations were performed using the linear trapezoidal rule.

As data permitted, the terminal elimination rate constant (lambda z, $\lambda z$) was calculated. The value of $\lambda z$ was determined by the slope of the regression line of the natural log transformed concentrations versus time with the following constraints:

Data points should be randomly distributed around a single straight line;
At least three data points post the $C_{max}$ should be used in the regression;
The correlation coefficient ($R^2$) of regression should be >0.80;
To optimize the reliability of the identified terminal phase ($\lambda z$), where possible, the data points used to define the $\lambda z$ were manually selected. Lambda z profiles that did not meet the guidelines stated above excluded the $AUC_{INF}$, $t_{1/2}$, CL/F, and Vz/F parameters for that animal profile with an asterisk and excluded the results from summary descriptive statistics.

The $AUC_{INF}$ value was calculated as: $AUC_{last}+(C_{last}/\lambda z)$. CL/F was calculated as: Dose per dosing interval/($AUC_{INF}$) and Vz/F was calculated as: Dose per dosing interval/($AUC_{INF}*\lambda z$). Terminal $t_{1/2}$ was calculated as: $\ln(2)/\lambda z$. If the lambda z interval was not at least 2-fold greater than the calculated half-life, the half-life value was flagged as unreliable with an asterisk and excluded from descriptive statistics.

Mean plasma concentration versus time data are presented with standard deviation (SD) and percent coefficient of variation (CV %) and reported to three significant figures. PK parameter values are presented with mean, SD, and CV %. Individual $T_{max}$ values were reported to two significant figures, while all other values and descriptive statistics are reported to three significant figures.

Individual animal and group mean PK parameters for the pro-drugs and abiraterone, following IV administration, are presented in Table 6 and Table 7. Individual animal and group mean PK parameters for the pro-drugs and abiraterone, following IM administration, are presented in Table 8 and Table 9. Group mean plasma concentration versus time profiles, following administration to dogs, are plotted in FIG. 5 through FIG. 10.

Results from IV administration: Following IV administration of abiraterone decanoate (pro-drug), a mean CL value of 8.88 mL/min/kg was calculated for the prodrug, which was considered low clearance. Using a dose value of 0.84 mg/kg (assuming 100% conversion of the prodrug to abiraterone) the mean CL/F value was 97.8 mL/min/kg for abiraterone. The mean Vz value was 0.659 L/kg for the pro-drug and the mean Vz/F value 13.0 L/kg for abiraterone. The mean $t_{1/2}$ value for the prodrug and abiraterone was 0.86 hours and 1.5 hours, respectively.

Exposure to abiraterone propionate was only observed in the first 2 time points after dose administration, as such no reliable PK parameters could be calculated. Following IV administration of abiraterone propionate (pro-drug), the mean CL/F value for abiraterone was 114 mL/min/kg, with a mean Vz/F value of 20.8 L/kg. The mean $t_{1/2}$ value for abiraterone was 2.1 hours.

While the abiraterone Cmax value was almost 4-fold higher following IV administration of abiraterone propionate, the AUC values were comparable (within 2-fold), suggesting marginal differences between the pro-drugs.

Results from IM administration: Following IM administration of the two decanoate formulations, mean abiraterone $T_{max}$ value was 5.0 days for either of the two formulations and the mean decanoate $T_{max}$ values ranged between 0.11 and 0.26 days between the formulations. The mean pro-drug and abiraterone exposures (as evidenced by $C_{max}$ and AUC values) were within 2-fold between the 2 formulations. The terminal elimination phase for the prodrug did not achieve a stable negative slope beyond the Day 7 time points, as such no additional disposition parameters could be assessed. For abiraterone, the mean $t_{1/2}$ value (terminal $t_{1/2}$) was 23 and 24 days following administration in the 2 vehicles. Estimates of the absolute bioavailability for abiraterone are calculated using the mean $AUC_{INF}$ values following IV administration (145 h*ng/mL) and IM administration (corrected for dose and time units=104 h*ng/mL for Group 5 and 134 h*ng/mL for Group 6). The bioavailability was 72 and 92% for Group 5 and 6, respectively.

Following IM administration of the two propionate formulations, mean abiraterone $T_{max}$ values ranged between 0.56 or 0.61 days and the mean propionate $T_{max}$ values ranged between 0.11 and 0.26 days (2.3 and 6.2 hours) between the formulations. The mean pro-drug and abiraterone exposures (as evidenced by $C_{max}$ and AUC values) were within 2-fold between the 2 formulations. Excluding the Day 7 time point (no values beyond Day 7), the mean t½ values for the pro-drug were between 0.98 and 1.7 days following administration of the 2 different vehicles. For abiraterone, the mean $t_{1/2}$ value was 1.8 and 4.5 days following administration in the 2 vehicles. Estimates of the absolute bioavailability for abiraterone are calculated using the mean $AUC_{INF}$ values following IV administration (127 h*ng/mL) and IM administration (corrected for dose and time units=105 h*ng/mL for Group 3 and 94.1 h*ng/mL for Group 4). The bioavailability was 83 and 74% for Group 3 and 4, respectively.

Tables 6-9 and FIGS. 5-10 provide a summary of the PK studies of this example.

Computer-modeling was also used to predict the human pharmacokinetic profile of abiraterone decanoate administered IM to humans based on data obtained from the rat and dog studies. Pharmacokinetic (PK) modelling and simulations were carried out using a fully-validated version (8.1) of WinNonlin Phoenix. Linear PK (exponential) models were fitted to the plasma concentration-time profiles of abiraterone following IV administration of abiraterone (acetate or decanoate formulations) to rats and dogs. The derived PK parameters of clearance (CL) and distribution volume (Vss) were predicted in man by allometric scaling. The rate (K01) and extent (F) of bioavailability of abiraterone after IM administration to dogs was estimated by deconvolution; values of K01 and F were assumed to be equivalent in man.

The predicted PK parameters (CL, Vss, K01 and F) were used to simulate plasma concentration-time profiles in man after IM administration with various prescribed dose regimens (assuming linear kinetics of abiraterone.) The modeling predicted that an IM dose of as low as 120 mg abiraterone decanoate every two weeks can achieve a therapeutically effective abiraterone plasma concentration in human with a $C_{min}$ value of abiraterone at steady state greater than about 8 ng/ml, with a $C_{max}$ value of abiraterone at steady state of about 14 ng/ml. The modeling also predicted that an IM dose of abiraterone decanoate is suitable for once a month or once in more than a month dosing regimen in human, which can provide a therapeutically effective abiraterone plasma concentration. For example, an IM dose of about 350 mg abiraterone decanoate once in 4 weeks is sufficient to provide a $C_{min}$ value of abiraterone at steady state greater than about 8 ng/ml. $C_{max}$ value of abiraterone at steady state generally is dose proportional. See also FIG. 11A, FIG. 11B, FIG. 11C, and FIG. 11D. In light of this disclosure, in some cases, the dosing regimen can also include an initial dosing period with a higher dosing frequency or with a different abiraterone medication to achieve certain exposure of abiraterone in a treated subject, which is then followed by a once a month (or in more than a month) dosing regimen as described herein. For example, in some cases, the dosing regimen can include an initial IM doses of abiraterone decanoate once in two weeks, e.g., for about 2-3 doses, which is then followed by a once in a month administration of abiraterone decanoate. Computer modeling predicted that such dosing regimen can achieve a $C_{min}$ value of abiraterone at steady state greater than about 8 ng/ml during the treatment period.

TABLE 6

Group Mean Abiraterone or Abiraterone Decanoate Plasma PK Parameters
Following IV Administration of 1.2 mg/kg Abiraterone Decanoate in Dogs (N = 6)

| Analyte Dose (mg/kg) | | $T_{max}$ (h) | $C_{max}$ (ng/mL) | $AUC_{0-8}$ (h * ng/mL) | $AUC_{last}$ (h * ng/mL) | $AUC_{INF}$ (h * ng/mL) | Vz or Vz/F (L/kg) | CL or CL/F (mL/min/kg) | $t_{1/2}$ (h) |
|---|---|---|---|---|---|---|---|---|---|
| Abiraterone | Mean | 0.833 | 57.2 | 135 | 143 | 145 | 13.0 | 97.8 | 1.54 |
| 0.83 | SD | 0.129 | 5.78 | 21.7 | 28.0 | 26.9 | 2.86 | 17.6 | 0.202 |
|  | CV % | 15.5 | 10.1 | 16.0 | 19.6 | 18.5 | 22.0 | 18.0 | 13.1 |
| Abiraterone | Mean | 0.0833 | 1890 | 2250 | 2260 | 2260 | 0.659 | 8.88 | 0.858 |
| Decanoate | SD | 0.00 | 220 | 143 | 141 | 142 | 0.0329 | 0.577 | 0.0202 |
| 1.2 | CV % | 0.00 | 11.6 | 6.35 | 6.26 | 6.27 | 5.00 | 6.50 | 2.36 |

TABLE 7

Group Mean Abiraterone or Abiraterone Propionate Plasma PK Parameters
Following IV Administration of 1 mg/kg Abiraterone Propionate in Dogs (N = 6)

| Analyte Dose (mg/kg) | | $T_{max}$ (h) | $C_{max}$ (ng/mL) | $AUC_{0-8}$ (h * ng/mL) | $AUC_{last}$ (h * ng/mL) | $AUC_{INF}$ (h * ng/mL) | Vz/F (L/kg) | CL/F (mL/min/kg) | $t_{1/2}$ (h) |
|---|---|---|---|---|---|---|---|---|---|
| Abiraterone | Mean | 0.0833 | 222 | 112 | 126 | 127 | 20.8 | 114 | 2.11 |
| 0.86 | SD | 0.00 | 30.8 | 11.9 | 14.1 | 14.2 | 2.53 | 12.9 | 0.142 |
|  | CV % | 0.00 | 13.9 | 10.7 | 11.2 | 11.2 | 12.2 | 11.3 | 6.76 |
| Abiraterone | Mean | 0.0833 | 27.1 |  |  |  |  |  |  |
| Propionate | SD | 0.00 | 5.47 |  |  |  |  |  |  |
| 1.0 | CV % | 0.00 | 20.2 |  |  |  |  |  |  |

TABLE 8

Individual Animal and Group Mean Abiraterone or Abiraterone Decanoate Plasma PK Parameters Following IM Administration of 41 mg/kg Abiraterone Decanoate in Dogs

| Analyte | Group | | $T_{max}$ (d) | $C_{max}$ (ng/mL) | $AUC_{0-28}$ (d * ng/mL) | $AUC_{last}$ (d * ng/mL) | $AUC_{INF}$ (d * ng/mL) | Vz/F (L/kg) | CL/F (mL/min/kg) | $t_{1/2}$ (d) |
|---|---|---|---|---|---|---|---|---|---|---|
| Abiraterone | 5 | N | 3 | 3 | 3 | 3 | 2 | 2 | 2 | 2 |
| | | Mean | 5.0 | 5.66 | 99.2 | 141 | 178 | 6560 | 138 | 23 |
| | | SD | 0.0 | 1.25 | 13.3 | 19.8 | 21.9 | 1170 | 17.0 | 1.3 |
| | | CV % | 0.00 | 22.1 | 13.4 | 14.1 | 12.3 | 17.8 | 12.3 | 5.53 |
| Abiraterone | 6 | N | 3 | 3 | 3 | 3 | 2 | 2 | 2 | 2 |
| | | Mean | 5.0 | 8.99 | 135 | 184 | 229 | 5330 | 107 | 24 |
| | | SD | 0.0 | 0.760 | 14.1 | 4.28 | 28.0 | 300 | 13.0 | 4.3 |
| | | CV % | 0.00 | 8.45 | 10.5 | 2.33 | 12.2 | 5.62 | 12.2 | 17.8 |
| Abiraterone Decanoate | 5 | N | 3 | 3 | 3 | 3 | 0 | 0 | 0 | 0 |
| | | Mean | 0.26 | 4.15 | 16.6 | 30.0 | | | | |
| | | SD | 0.21 | 0.673 | 1.72 | 8.07 | | | | |
| | | CV % | 81.2 | 16.2 | 10.3 | 26.9 | | | | |
| Abiraterone Decanoate | 6 | N | 3 | 3 | 3 | 3 | 0 | 0 | 0 | 0 |
| | | Mean | 0.11 | 6.61 | 21.9 | 35.9 | | | | |
| | | SD | 0.024 | 2.70 | 6.12 | 1.40 | | | | |
| | | CV % | 21.8 | 40.9 | 27.9 | 3.89 | | | | |

TABLE 9

Individual Animal and Group Mean Abiraterone or Abiraterone Propionate Plasma PK Parameters Following IM Administration of 50 mg/kg Abiraterone Propionate in Dogs (N = 3)

| Analyte | Group | | $T_{max}$ (d) | $C_{max}$ (ng/mL) | $AUC_{0-28}$ (d * ng/mL) | $AUC_{last}$ (d * ng/mL) | $AUC_{INF}$ (d * ng/mL) | Vz/F (L/kg) | CL/F (mL/min/kg) | $t_{1/2}$ (d) |
|---|---|---|---|---|---|---|---|---|---|---|
| Abiraterone | 3 | Mean | 0.556 | 22.8 | 215 | 217 | 219 | 1050 | 112 | 4.53 |
| | | SD | 0.419 | 1.55 | 19.1 | 19.9 | 19.6 | 219 | 10.5 | 0.949 |
| | | CV % | 75.5 | 6.79 | 8.88 | 9.20 | 8.92 | 20.9 | 9.38 | 21.0 |
| Abiraterone | 4 | Mean | 0.611 | 74.9 | 198 | 190 | 196 | 467 | 124 | 1.81 |
| | | SD | 0.347 | 29.0 | 12.0 | 14.5 | 11.7 | 36.8 | 7.45 | 0.135 |
| | | CV % | 56.8 | 38.7 | 6.05 | 7.60 | 5.98 | 7.88 | 6.00 | 7.44 |
| Abiraterone Propionate | 3 | Mean | 0.111 | 7.15 | 15.7 | 13.0 | 14.9 | 6870 | 1980 | 1.71 |
| | | SD | 0.0485 | 1.02 | 3.08 | 2.82 | 3.29 | 1570 | 481 | 0.502 |
| | | CV % | 43.7 | 14.3 | 19.6 | 21.7 | 22.1 | 22.9 | 24.3 | 29.3 |
| Abiraterone Propionate | 4 | Mean | 0.104 | 31.6 | 28.6 | 28.0 | 29.0 | 2110 | 1000 | 0.983 |
| | | SD | 0.0953 | 18.4 | 5.67 | 5.97 | 5.29 | 937 | 181 | 0.264 |
| | | CV % | 91.6 | 58.3 | 19.8 | 21.3 | 18.2 | 44.4 | 18.0 | 26.9 |

Example 6A. Large Scale Preparation of Abiraterone Decanoate from Decanoic Acid

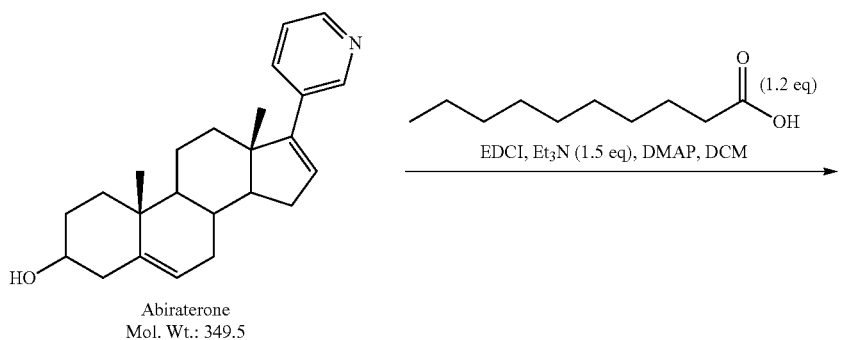

Abiraterone
Mol. Wt.: 349.5

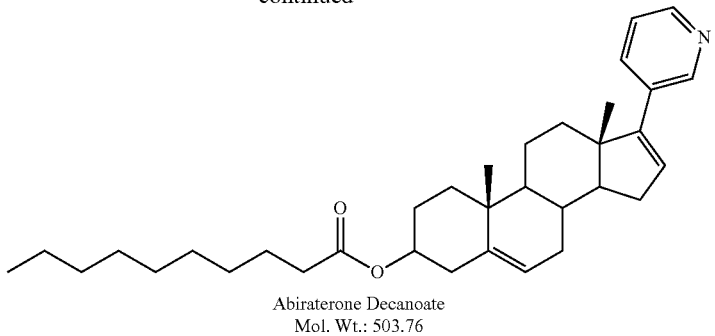

Abiraterone Decanoate
Mol. Wt.: 503.76

To a suspension of Abiraterone (381.9 g, 1.09 mol) in dichloromethane (3500 mL) was added triethylamine (165 g, 1.64 mol) and a catalytic amount of DMAP (13.35 g, 0.109 mol). Decanoic acid (225 g, 1.31 mol) as a solution in dichloromethane (500 mL) was added to the suspension, followed by EDCI (293 g, 1.53 mol) and the reaction then agitated for 19 h at 20-25° C.

10 wt % aq $NaH_2PO_4$ (4000 mL) was then added and the reaction was agitated for 20 min. The organic layer was separated and extracted with 10 wt % aq $NaH_2PO_4$ (2000 mL) and brine (2000 mL). The organic layer was solvent exchanged with acetonitrile (4750 mL) and concentrated to 3100 g keeping temperature of bath <40° C. The suspension was diluted with acetonitrile (900 g). The solids were isolated by filtration to afford 510 g of crude abiraterone decanoate.

510 g of the crude abiraterone decanoate was dissolved in acetone (4000 mL) at 40° C. The solution was filtered through a filter paper. The filtrate was transferred to a 12 L 3-neck flask, diluted to 5100 g and reheated to 40° C. to form a solution. The solution was cooled slowly to 20° C. to form a suspension. This was diluted with water (1020 mL) and agitated at RT overnight. The solid was filtered and the flask was rinsed with the filtrate and transferred to filter funnel. The wet cake was transferred to drying tray and dried at 40-45° C. in vacuum oven overnight to obtain 457.1 g (90% yield) as white solid. $^1$H NMR ($CDCl_3$, 400 MHz): $d_H$ 8.62 (d, 1H, J=1.9 Hz), 8.31 (dd, 1H, J=4.9, 1.6 Hz), 7.64 (dt, 1H, J=7.9, 1.9 Hz), 7.21 (ddd, 1H, J=8.0, 4.9, 0.8 Hz), 6.01-5.97 (m, 1H), 5.44-5.40 (m, 1H), 4.68-4.58 (m, 1H), 2.39-2.23 (m, 3H), 2.27 (t, 2H, J=7.6 Hz), 2.12-2.00 (m, 3H), 1.91-1.54 (m, 10H), 1.49 (dt, 1H, J=11.9, 5.1 Hz), 1.35-1.23 (m, 12H), 1.20-1.07 (m, 2H), 1.08 (s, 3H), 1.05 (s, 3H), 0.88 (t, 3H, J=6.8 Hz). Elemental Analysis, theoretical (corrected for 0.055% moisture level): C, 81.0%, H, 9.8%, N, 2.8%; found: C, 81.1%, H, 10.2%, N, 2.8%.

The abiraterone decanoate obtained in this example was determined to have a purity of 99.7% by weight using a HPLC method. For HPLC analysis, abiraterone decanoate samples were prepared in methanol at a concentration of 0.05 mg/mL (for assay analysis) or 5 mg/mL (for impurity analysis). The HPLC conditions are the following: HPLC column: Halo C8 (2.7 um, 100×3.0 mm); injection volume: 5 uL; Column Temperature: 40° C.; Sample Temperature: ambient; Detection: 210 nm; Mobile Phase: 25 mM Ammonium Acetate, pH 8.0 (MPA) and 95/5 acetonitrile/tetrahydrofuran (MPB); Flow Rate: 0.6 ml/min; Gradient: starting with 65/35 MPA/MPB, in 35 minutes, reaching to 100% MPB, hold at 100% MPB until 40 minutes, at 40.10 minute, back to 65/35 MPA/MPB, and hold at 65/35 MPA/MPB until end at 45 minutes.

Figure 12C:
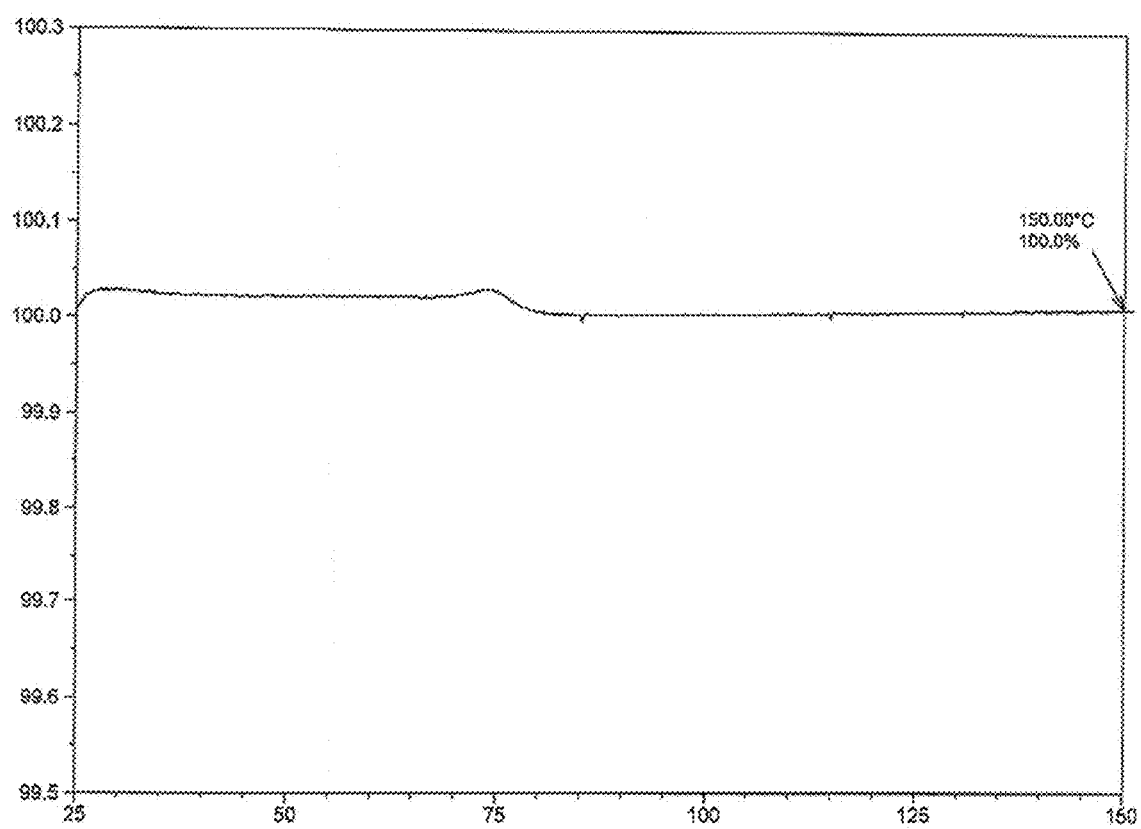
FIG. 12C shows a thermogravimetric analysis (TGA) of the abiraterone decanoate solid form prepared in Example 6A.
Figure 13A:
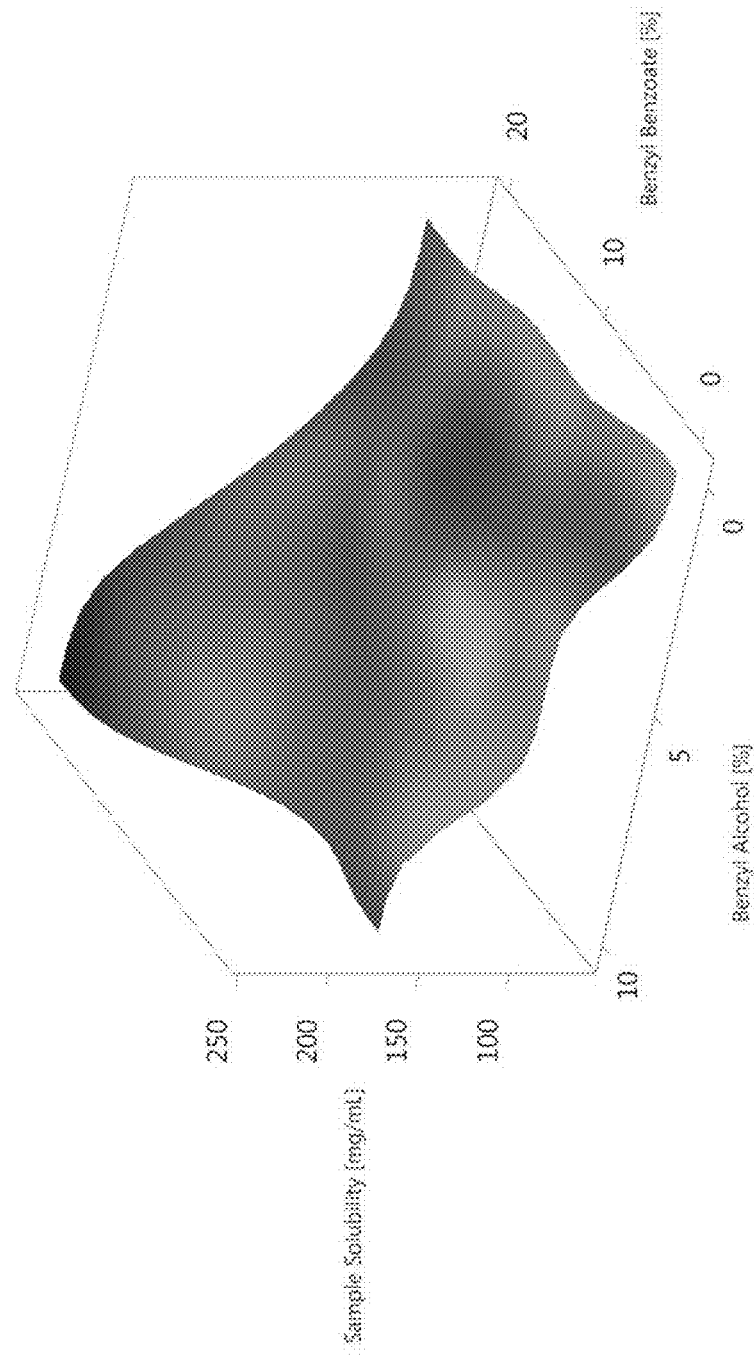
FIG. 13A presents a plot of abiraterone decanoate solubility in corn oil in the presence of various amounts of benzyl alcohol and benzyl benzoate.
Figure 13B:
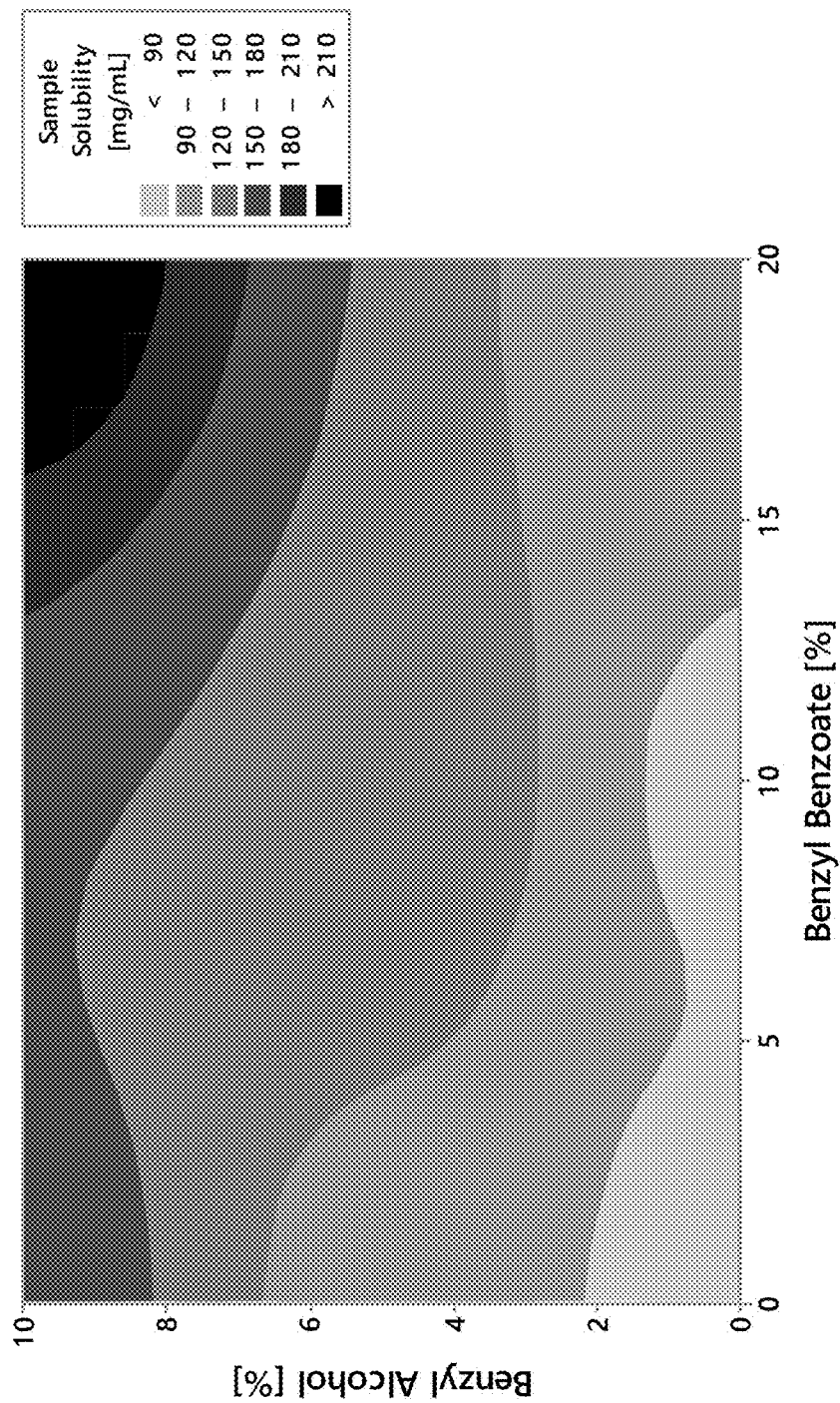
FIG. 13B shows a contour plot of abiraterone decanoate solubility in corn oil in the presence of various amounts of benzyl alcohol and benzyl benzoate.
Figure 13C:
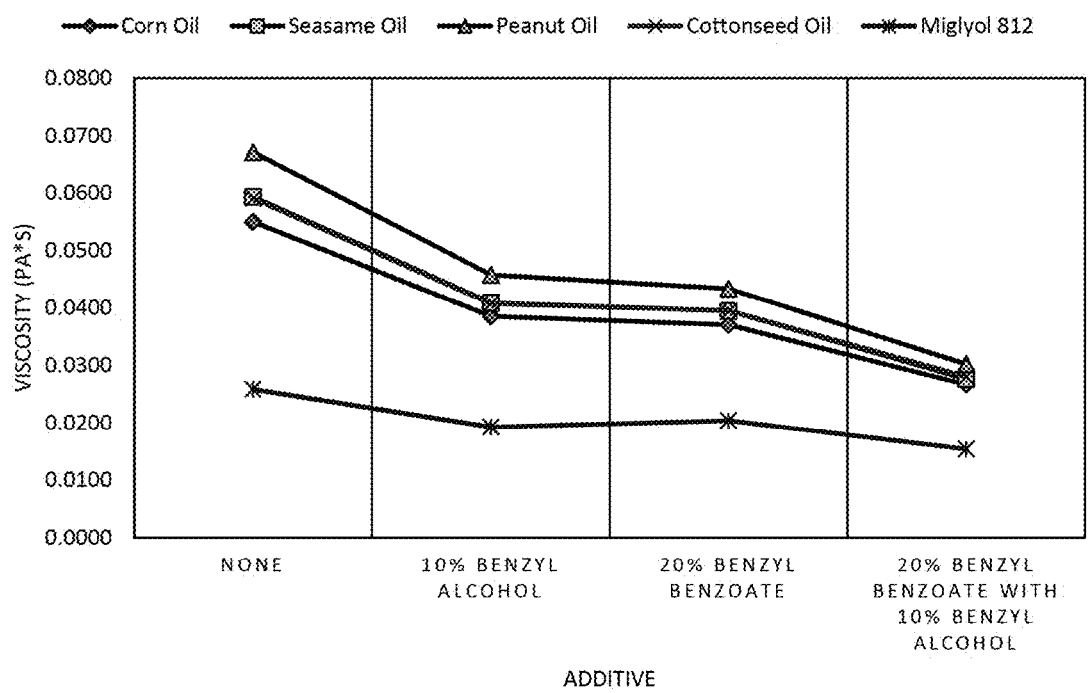
FIG. 13C shows viscosity (Pa*s) for various oil vehicles, without additive or with 10% benzyl alcohol, 20% benzyl benzoate, or a combination of 10% benzyl alcohol and 20% benzyl benzoate.
Figure 13D:
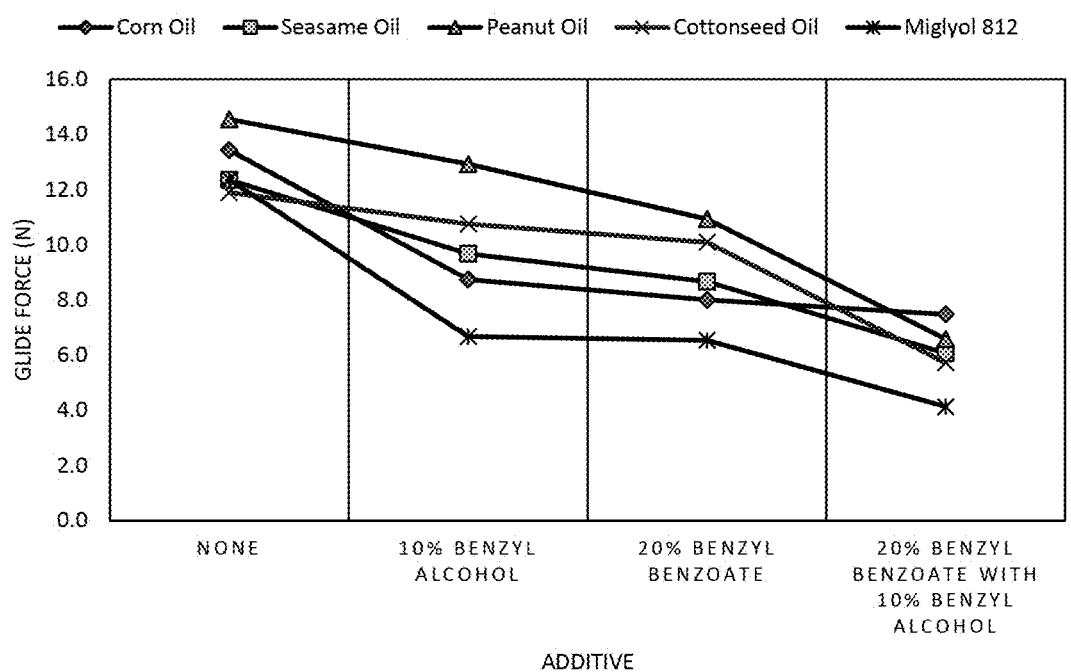
FIGS. 13D and 13E show Glide Foce (N) for various oil vehicles, without additive or with 10% benzyl alcohol, 20% benzyl benzoate, or a combination of 10% benzyl alcohol and 20% benzyl benzoate tested with 5 ml Syringe, with 23 Gauge needle or 27 Gauge needle, respectively.
Figure 13E:
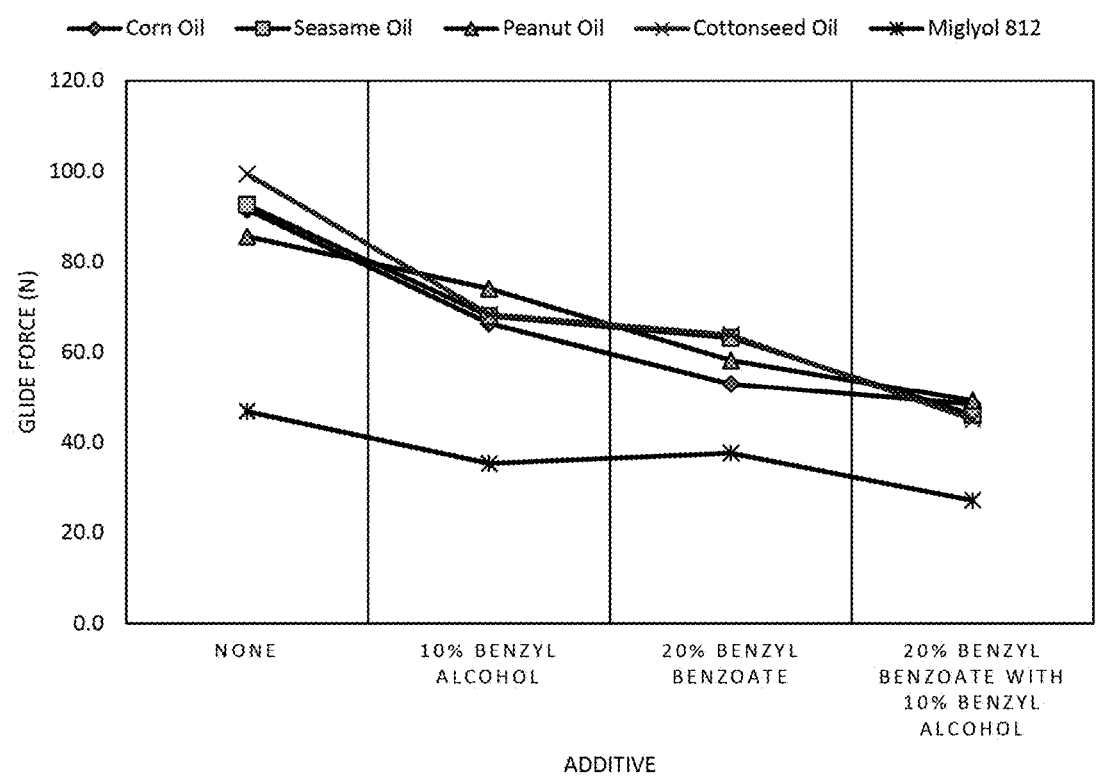

The white solid obtained in this example was also characterized by X-Ray Powder Diffraction (XRPD) and Differential Scanning Calorimetry (DSC). XRPD was conducted with Bruker's D8 Discover X-rat diffractometer, with Theta\theta vertical goniometer, using Vantec-500 as detector. Standard conditions: voltage 40 kV, current 40 mA, radiation, Cu, temperature, ambient, X-ray source exit slit size, 0.5 mm pinhole, snout collimator, 0.5 mm, sample holder, ground quartz plate. Operating conditions: detector distance, 30 cm, Chi integration range, 4-40 degree 20, count time, 120 seconds/frame, # of frames: 3, Theta 1 position, 4 degree, Theta 2 position, 4 degree, Frame width, 12, scan axis, coupled. Software used include GADDs software, General Area Detector Diffraction System, version 4.1.50; and DIFFRAC.EVA, version 4.0. DSC was performed with TA Instruments Q2000 (Thermal Advantage V 5.0.0—qualified), with a sample size of 2-10 mg, heating range from 25° C. to 250° C. at a heating rate of 10° C./min. Representative XRPD and DSC spectra are shown in FIGS. 12A-12B. A thermogravimetric analysis (TGA) was also performed on this sample. TGA was performed with TA Instruments TGA Q500 (Thermal Advantage V5.2.5—qualified), with a sample size of 5-20 mg, heating range from 25° C. to 150° C. at a heating rate of 10° C./min. A representative TGA trace is shown in FIG. 12C.

Example 6B. Preparation of Abiraterone Decanoate Salts

Preparation of Abiraterone Decanoate Oxalate Salt

A solution of Abiraterone Decanoate (374 g, 744 mmoles) dissolved in isopropyl acetate to 5200 g and taken in a 12 L reactor. Oxalic acid (18.0 g) was charged and agitated for 2 h. The suspension was warmed to 72° C. and agitated for 2 h. After cooling to 60° C., oxalic acid (20 g) and isopropyl acetate (1000 g) were charged. Heating was continued at 60° C. for 30 min. More oxalic acid (20 g) and isopropyl acetate (600 g) were charged and heating was continued at 60° C. After 30 min more oxalic acid (15.7 g) and isopropyl acetate (600 g) were charged. Reaction temperature was increased to 72° C. and heating was maintained for 18 h.

The reaction was then cooled to RT and further to 5-10° C. and the slurry was agitated for 2 h at the same temperature. The solids were filtered and rinsed with cold isopropyl acetate (520 mL). The wet cake was transferred to drying trays and dried in vacuum oven at 45-50° C. until constant weight of 410 g (92.8% yield). HPLC of the ABIRATERONE DECANOATE oxalate showed a purity of 99.62A %. $^1$H NMR ($CDCl_3$, 400 MHz): $d_H$ 12.62 (brs, 2H), 8.84 (d, 1H, J=1.8 Hz), 8.69 (d, 1H, J=5.5, 1.1 Hz), 8.24 (dt, 1H, J=8.3, 1.7 Hz), 7.75 (dt, 1H, J=8.2, 5.5), 6.32-6.29 (m, 1H), 5.44-5.39 (m, 1H), 4.68-4.58 (m, 1H), 2.42-2.31 (m, 3H), 2.28 (t, 2H, J=7.5 Hz), 2.20-2.00 (m, 3H), 1.93-1.47 (m, 11H), 1.38-1.11 (m, 14H), 1.10 (s, 6H), 0.88 (t, 3H, J=6.9 Hz).

Preparation of Abiraterone Decanoate HCl Salt

A solution of Abiraterone Decanoate (20 mmol) in EtOAc (140 mL) was treated with 2 M HCl/ether (12 mL; 24 mmol; 1.2 eq.). The suspension was heated at 50° C. overnight; then cooled to 0-5° C. for 2 h. The solids filtered reasonably fast and it was rinsed with EtOAc to obtain 7.97 g (14.76 mmol; 74% yield) of ABIRATERONE DECANOATE HCl salt as white solid. $^1$H NMR (CDCl$_3$, 400 MHz): d$_H$ 8.70 (d, 1H, J=1.6 Hz), 8.58 (dd, 1H, J=1.6, 5.6 Hz), 8.34 (dt, 1H, J=8.3, 1.6 Hz), 7.84 (dd, 1H, J=8.3, 5.6 Hz), 6.37-6.33 (m, 1H), 5.44-5.39 (m, 1H), 4.68-4.58 (m, 1H), 4.43-2.31 (m, 3H), 2.27 (t, 2H, J=7.5 Hz), 2.20-2.00 (m, 3H), 1.92-1.45 (m, 13H), 1.36-1.23 (m, 13H), 1.21-1.10 (m, 2H), 1.09 (s, 3H), 1.08 (s, 3H), 0.88 (t, 3H, J=6.9 Hz).

Preparation of Abiraterone Decanoate Benzene Sulfonic Salt

A solution of ABIRATERONE DECANOATE (0.57 mmol) in ethyl acetate (10 ml) was treated with benzene sulfonic acid (0.72 mmol. The resulting solid ABIRATERONE DECANOATE benzene sulfonate salt (0.72 mmol) was isolated by filtration (74% yield). $^1$H NMR (CDCl$_3$, 400 MHz): d$_H$ 8.87 (d, 1H, J=1.7 Hz), 8.81 (brd, 1H, J=5.6 Hz), 8.32 (dt, 1H, J=8.1, 1.4 Hz), 7.97-7.92 (m, 2H), 7.86 (dd, 1H, J=8.1, 5.6 Hz), 7.41-7.36 (m, 3H), 6.36-6.32 (m, 1H), 5.44-5.38 (m, 1H), 4.68-4.56 (m, 1H), 2.59-2.30 (m, 3H), 2.27 (t, 2H, J=7.5 Hz), 2.17-2.00 (m, 4H), 1.91-1.54 (m, 10H), 1.47 (dt, 1H, J=12.1, 4.7 Hz), 1.35-1.22 (m, 15H), 1.20-1.10 (m, 1H), 1.08 (s, 3H), 1.06 (s, 3H), 0.88 (t, 3H, J=7.2 Hz).

Preparation of Abiraterone Decanoate p-Toluene Sulfonate Salt

A solution of ABIRATERONE DECANOATE (0.57 mmol) in ethyl acetate (10 ml) was treated with p-Toluene sulfonic acid (0.72 mmol. The resulting solid ABIRATERONE DECANOATE p-Toluene sulfonate salt was isolated by filtration (64% yield). $^1$H NMR (CDCl$_3$, 400 MHz): d$_H$ 8.85 (d, 1H, J=1.7 Hz), 8.81 (brd, 1H, J=5.6 Hz), 8.31 (dt, 1H, J=8.4, 1.6 Hz), 7.85 (dd, 1H, J=8.3, 5.8 Hz), 7.82 (dt, 1H, J=8.3, 1.6 Hz), 7.18 (d, 2H, J=8.0 Hz), 6.36-6.31 (m, 1H), 5.45-5.39 (m, 1H), 4.69-4.57 (m, 1H), 2.57-2.30 (m, 6H), 2.28 (t, 2H, J=7.5 Hz), 2.19-2.00 (m, 4H), 1.93-1.54 (m, 10H), 1.46 (dt, 1H, J=4.8, 1.20 Hz), 1.36-1.10 (m, 16H), 1.08 (s, 3H), 1.06 (s, 3H), 0.88 (t, 3H, J=6.9 Hz).

Preparation of Abiraterone Decanoate Phosphate Salt

A solution of ABIRATERONE DECANOATE (1.0 mmol) in isopropyl acetate (10 ml) was treated with phosphoric acid (69.6 mg, 0.61 mmol). The resulting solid ABIRATERONE DECANOATE phosphate salt was isolated by filtration (0.39 g, 65% yield). 1H NMR (CDCl$_3$, 400 MHz): d$_H$ 9.75 (brs, 4H), 8.60 (brs, 2H), 8.00 (brd, 1H, J=7.7), 7.65 (brs, 1H), 6.17 (brs, 1H), 5.37 (brs, 1H), 4.59 (brs, 1H), 2.45-2.16 (m, 6H), 2.09-1.78 (m, 5H), 1.73-1.44 (m, 9H), 1.35-1.21 (m, 16H), 1.03 (s, 3H), 0.95 (s, 3H), 0.88 (t, 3H, J=6.9 Hz).

Example 7. Studies of Abiraterone Decanoate in Rats and Monkeys and Allometric Scaling and Prediction of Plasma Profile in Human Example 7a. Studies of Abiraterone Decanoate in Monkeys In the monkey PK studies, abiraterone decanoate formulation (90% Corn Oil, 10% Benzyl Alcohol, 192 mg/ml abiraterone decanoate) was dosed intramuscularly at 90 mg/kg in Male Cynomolgus Monkeys (n=3).

An IV dose of Abiraterone Decanoate (0.4 mg/ml solution in 40% HP-beta-cyclodextrin 25 mM Na phosphate buffer (pH 7.4) dosed at 1.2 mg/kg (Average n=3) was used as comparison. For the IV dose, blood samples were taken at 0 hr, 0.083 hr, 0.17 hr, 0.25 hr, 0.5 hr, 0.75 hr, 1 hr, 2 hr, 4 hr, 8 hr, and 24 hr. The results are shown in Table 10A and FIG. 14A.

TABLE 10A

Monkey IV PK parameters (arithmetic mean)

|  | $T_{max}$ (h) | $C_{max}$ (ng/mL) | $AUC_{inf}$ (ng · h/mL) | $t_{1/2}$ (h) |
|---|---|---|---|---|
| Abiraterone Decanoate | 0.083 | 2450 | 2860 | 2.27 |
| Abiraterone | 0.83 | 123 | 376 | 2.59 |

Single Dose PK studies were carried out by injection of the abiraterone decanoate formulation (90% Corn Oil, 10% Benzyl Alcohol, 192 mg/ml abiraterone decanoate) intramuscularly at 90 mg/kg in Male Cynomolgus Monkeys (n=3). The abiraterone decanoate formulation was injected intramuscularly with split between 2 injections into the thigh on each hind leg, using 27-Gauge needle. Blood samples were taken at 0 hr, 0.5 hr, 1 hr, 2 hr, 3 hr, 4 hr, 5 hr, 8 hr, 24 hr, 48 hr, 72 hr, 120 hr, 168 hr, 336 hr, 504 hr, 672 hr, 840 hr, 1008 hr, 1176 hr, 1344 hr. Plasma concentration of Abiraterone Decanoate and Abiraterone were determined. The results are shown in Table 10B and FIG. 14B.

TABLE 10B

Monkey single Dose PK parameters (geometric mean; Tmax is the median)

|  | $T_{max}$ (days) | $C_{max}$ (ng/mL) | AUC (ng · days/mL) | $t_{1/2}$ (days) | F (%) |
|---|---|---|---|---|---|
| Abiraterone Decanoate | 0.74 | 11 | 69.6 | 10 | 0.8 |
| Abiraterone | 6.3 | 10 | 156 | 16 | 14 |

The progesterone, cortisol, and testosterone levels were also analyzed in this single dose PK study. As shown in FIG. 14C, following the single dose IM injection, a long duration of CYP17A1 inhibition was achieved as evidenced by the sustained increase of progesterone level and reduction of cortisol and testosterone level. The reduction in testosterone level is modest as the monkeys in this study were non-castrated.

Figure 14E:
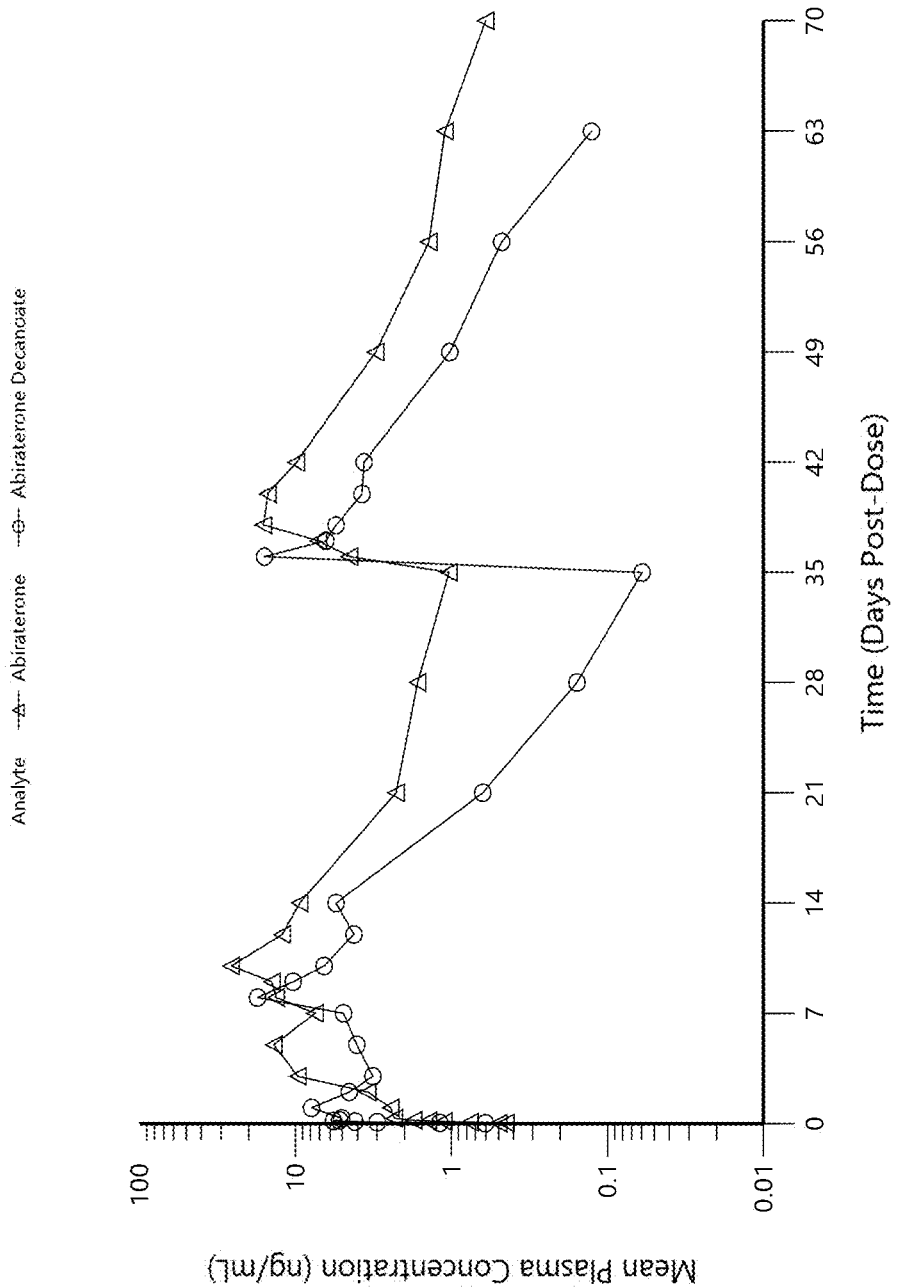
FIG. 14E shows mean abiraterone and abiraterone decanoate plasma concentration versus time profile data following multiple doses of IM administration of abiraterone decanoate formulation (90% Corn Oil, 10% Benzyl Alcohol, 192 mg/ml abiraterone decanoate) in Male Cynomolgus Monkeys (n=3) at Day 0, Day 7 and Day 35. Each dose is of 90 mg/kg abiraterone decanoate.

Multiple Dose PK studies were also carried out. In this study, multiple doses (each dose is 90 mg/kg) of the abiraterone decanoate formulation (90% Corn Oil, 10% Benzyl Alcohol, 192 mg/ml abiraterone decanoate) were injected intramuscularly in Male Cynomolgus Monkeys (n=3) at Day 0, Day 7 and Day 35. Each dose of the abiraterone decanoate formulation was injected intramuscularly with split between 2 injections into the thigh on each hind leg, using 27-Gauge needle. Blood samples were taken at 0 hr, 0.5 hr, 1 hr, 2 hr, 3 hr, 4 hr, 5 hr, 8 hr, 24 hr, 48 hr, 72 hr, 120 hr, 168 hr, 192 hr, 216 hr, 240 hr, 288 hr, 336 hr, 504 hr, 672 hr, 840 hr, 864 hr, 888 hr, 912 hr, 960 hr, 1008 hr, 1176 hr, 1344 hr, 1512 hr, 1680 hr. Plasma concentration of Abiraterone Decanoate and Abiraterone were determined. The results were shown in FIG. 14E.

Example 7B. Studies of the Impact of Benzyl Benzoate on Abiraterone Exposure in Monkeys This example compares the pharmacokinetic behaviours of IM injections of two different abiraterone decanoate formulations:

Formulation 1, Abiraterone Decanoate in 90% Corn oil 10%, benzyl alcohol, with the concentration of abiraterone decanoate of 207 mg/ml Formulation 2—Abiraterone Decanoate in 70% Corn Oil, 10% benzyl alcohol, 20% benzyl benzoate, with the concentration of abiraterone decanoate of 209 mg/ml.

Formulations 1 and 2 were intramuscularly dosed into male cynomolgus monkeys (n=1) at 100 mg/kg. The injections were given at day 0, day 7 and day 14. Blood samples were taken at 0 hr, 1 hr, 2.5 hr, 5 hr, 7.5 hr, 10 hr, 24 hr, 48 hr, 72 hr, 120 hr and 168 hr post each injection. Plasma abiraterone concentrations are shown in FIG. 14F.

Figure 14F:
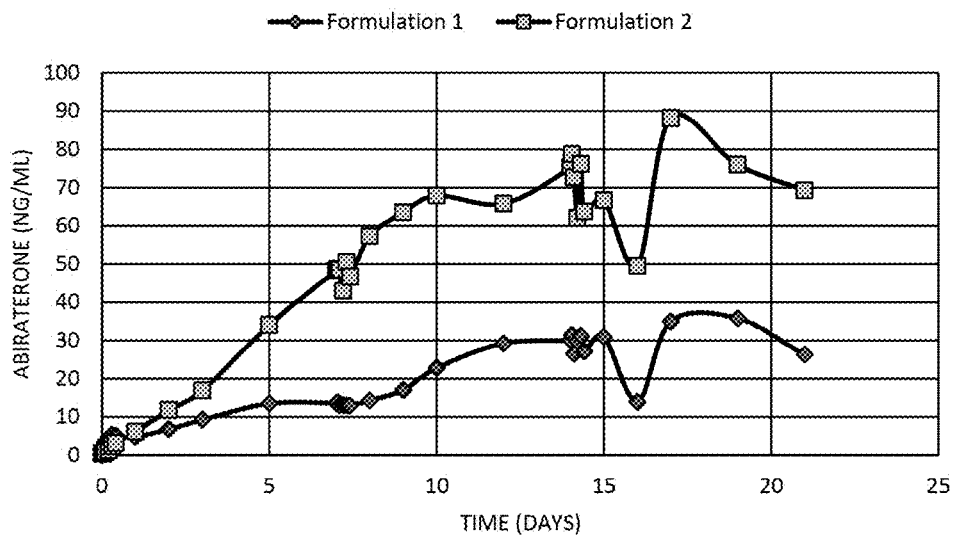
FIG. 14F shows mean abiraterone plasma concentration versus time profile data following multiple doses of IM administration of abiraterone decanoate Formulation 1 (90% Corn Oil, 10% Benzyl Alcohol, 207 mg/ml abiraterone decanoate) or Formulation 2 (70% Corn Oil, 10% Benzyl Alcohol, 20% benzyl benzoate, 209 mg/ml abiraterone decanoate) in Male Cynomolgus Monkeys (n=1) at Day 0, Day 7 and Day 14. Each dose is of 100 mg/kg abiraterone decanoate.

As shown in FIG. 14F, IM injection of Formulation 2 unexpectedly provided significantly higher abiraterone plasma concentrations in monkeys compared to IM injection of Formulation 1 at the same dose. This trend was also confirmed by parallel studies at different dosing levels.

Example 7C. Studies of Abiraterone Decanoate in Rats

In the rat PK studies, abiraterone decanoate formulation (90% Corn Oil, 10% Benzyl Alcohol, 172 mg/ml abiraterone decanoate) was dosed intramuscularly at 90 mg/kg in male rats (n=5).

Figure 15A:
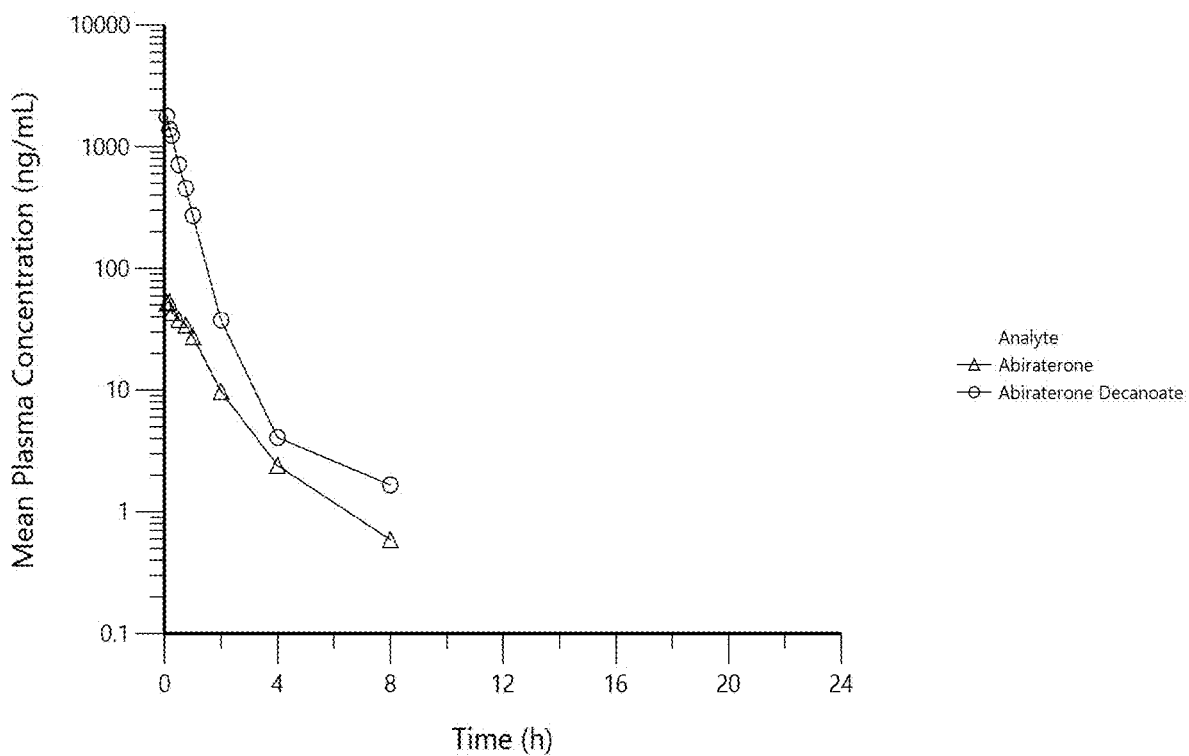
FIG. 15A shows mean abiraterone and abiraterone decanoate plasma concentration versus time profile data following IV administration of 1.2 mg/kg abiraterone decanoate (0.4 mg/ml solution in 40% HP-beta-cyclodextrin 25 mM Na phosphate buffer (pH 7.4)) in Male Rats (n=5).

An IV dose of Abiraterone Decanoate (0.4 mg/ml solution in 40% HP-beta-cyclodextrin 25 mM Na phosphate buffer (pH 7.4) dosed at 1.2 mg/kg (Average n=5) was used as comparison. For the IV dose, blood samples were taken at 0 hr, 0.083 hr, 0.17 hr, 0.25 hr, 0.5 hr, 0.75 hr, 1 hr, 2 hr, 4 hr, 8 hr, and 24 hr. The results are shown in Table 11A and FIG. 15A.

TABLE 11A

Rat IV PK parameters

| | $T_{max}$ (h) | $C_{max}$ (ng/mL) | $AUC_{inf}$ (ng · h/mL) | $t_{1/2}$ (h) |
|---|---|---|---|---|
| Abiraterone Decanoate | 0.083 | 1800 | 1020 | 3.2 |
| Abiraterone | 0.167 | 55.1 | 75.6 | 1.5 |

Figure 15B:
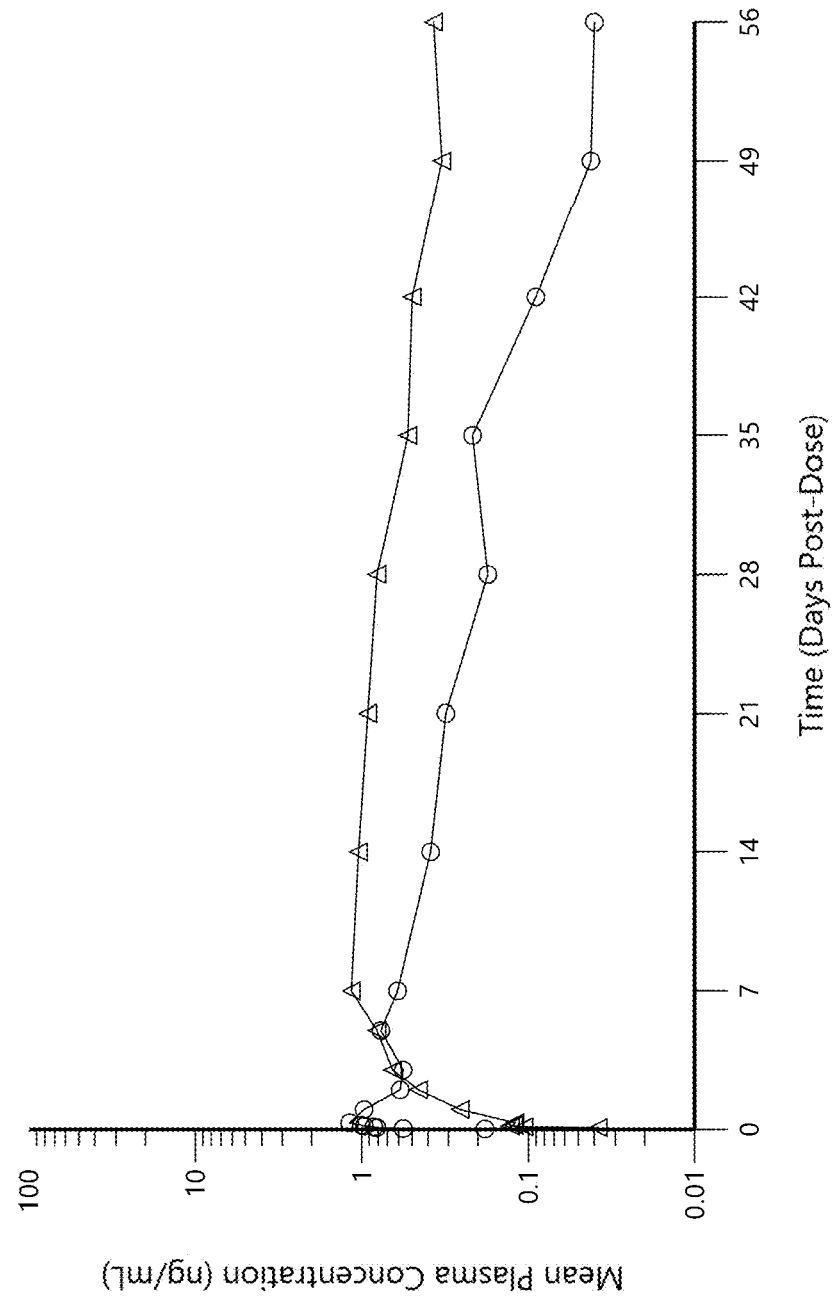
FIG. 15B shows mean abiraterone and abiraterone decanoate plasma concentration versus time profile data following a single IM administration of abiraterone decanoate formulation (90% Corn Oil, 10% Benzyl Alcohol, 172 mg/ml abiraterone decanoate) at a dose of 90 mg/kg abiraterone decanoate in Male Rats (n=5).

Single Dose PK studies were carried out by injection of the abiraterone decanoate formulation (90% Corn Oil, 10% Benzyl Alcohol, 172 mg/ml abiraterone decanoate) intramuscularly at 90 mg/kg in Male rats (n=5). The abiraterone decanoate formulation was injected intramuscularly into the thigh on hind leg, using 27-Gauge needle. Blood samples taken at 0 hr, 0.5 hr, 1 hr, 2 hr, 3 hr, 4 hr, 5 hr, 8 hr, 24 hr, 48 hr, 72 hr, 120 hr, 168 hr, 336 hr, 504 hr, 672 hr, 840 hr, 1008 hr, 1176 hr, 1344 hr. Plasma concentration of Abiraterone Decanoate and Abiraterone were determined. The results are shown in Table 11B and FIG. 15B.

TABLE 11B

Rat Single IM dose PK parameters

| | $T_{max}$ (days) | $C_{max}$ (ng/mL) | AUC (ng · days/mL) | $t_{1/2}$ (days) | F (%) |
|---|---|---|---|---|---|
| Abiraterone Decanoate | 0.46 | 1.3 | 25 | 33 | 0.8 |
| Abiraterone | 11 | 1.19 | 53 | 23 | 22 |

Figure 15C:
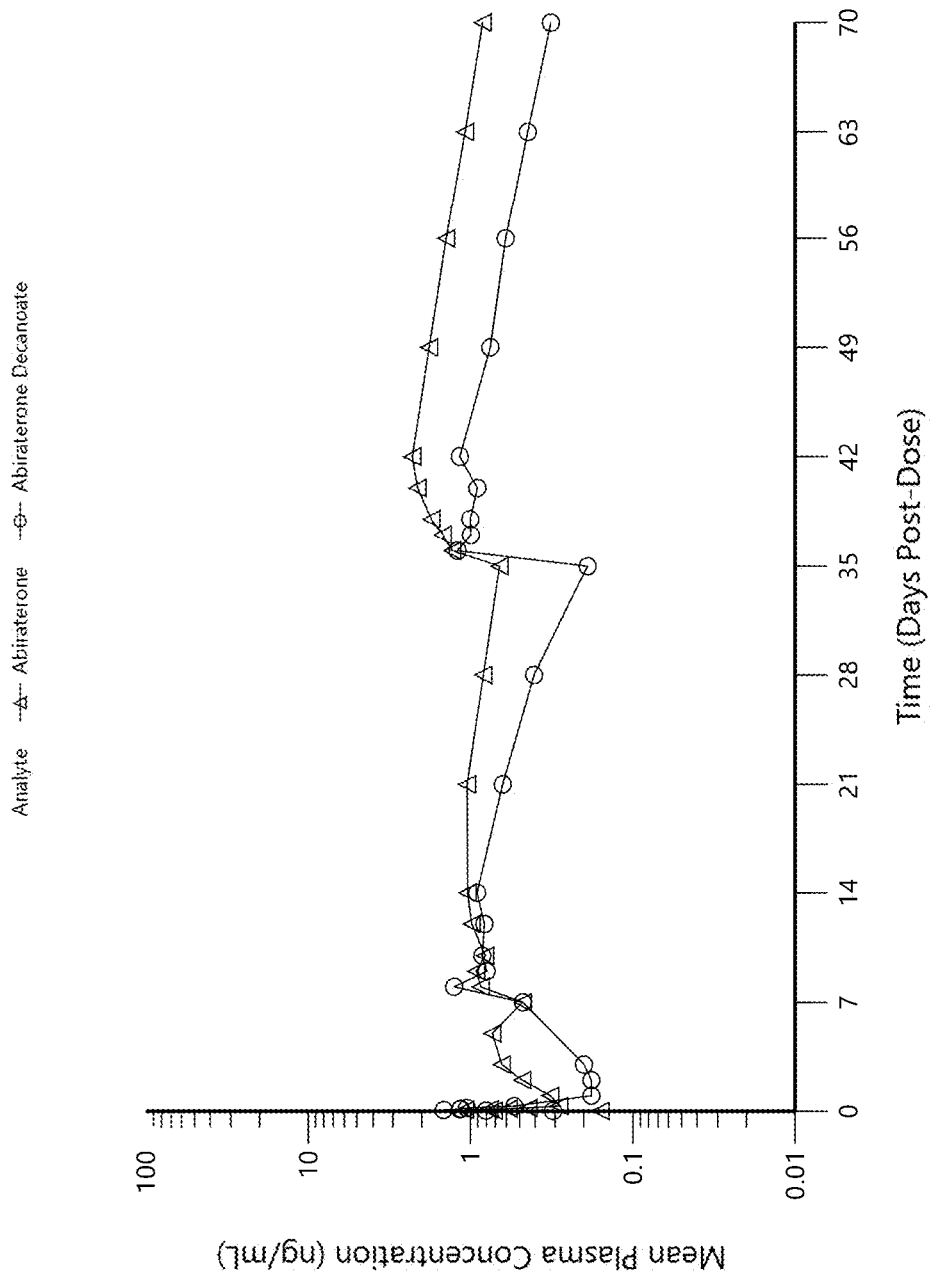
FIG. 15C shows mean abiraterone and abiraterone decanoate plasma concentration versus time profile data following multiple doses of IM administration of abiraterone decanoate formulation (90% Corn Oil, 10% Benzyl Alcohol, 172 mg/ml abiraterone decanoate) in Male Rats (n=5) at Day 0, Day 7 and Day 35. Each dose is of 90 mg/kg abiraterone decanoate.

Multiple Dose PK studies were also carried out. In this study, multiple doses (each dose is 90 mg/kg) of the abiraterone decanoate formulation (90% Corn Oil, 10% Benzyl Alcohol, 172 mg/ml abiraterone decanoate) were injected intramuscularly in Male rats (n=5) at Day 0, Day 7 and Day 35. Each dose of the abiraterone decanoate formulation was injected intramuscularly into the thigh on hind leg, using 27-Gauge needle. Blood samples were taken at 0 hr, 0.5 hr, 1 hr, 2 hr, 3 hr, 4 hr, 5 hr, 8 hr, 24 hr, 48 hr, 72 hr, 120 hr, 168 hr, 192 hr, 216 hr, 240 hr, 288 hr, 336 hr, 504 hr, 672 hr, 840 hr, 864 hr, 888 hr, 912 hr, 960 hr, 1008 hr, 1176 hr, 1344 hr, 1512 hr, 1680 hr. Plasma concentration of Abiraterone Decanoate and Abiraterone were determined. The results are shown in FIG. 15C.

Example 7D. Allometric Scaling and Prediction of Plasma Profile of Abiraterone in Man This pharmacokinetic (PK) analysis deals with the modelling of plasma concentrations of abiraterone following single intravenous (IV) and intramuscular (IM) administration of abiraterone to rats, dogs and monkeys. PK parameters were derived from the PK model after IV dosing and IM dosing in rats, dogs and monkeys to predict, by means of deconvolution and allometric scaling, the plasma profile of abiraterone in man after IM dosing of abiraterone decanoate.

Abiraterone decanoate was administered IV (1.2 mg/kg) and IM (90 mg/kg) to rats and monkeys; each animal received IV and IM doses. Abiraterone decanoate was administered IV (1.2 mg/kg) and IM (50 mg/kg) to dogs and IM (87 mg/kg) to dogs. Following single IV administration in rats, dogs and monkeys and single intramuscular administration in dogs, plasma samples were taken up 24 h. Following single IM administration in rats, dogs and monkeys, plasma samples were taken up to 1344 h. The PK results were reported herein.

Pharmacokinetic modelling: Pharmacokinetic models (one and two-compartment with zero-order input were fitted (with or without weighting of 1/C predicted) to the plasma concentration profiles of abiraterone in individual animals, following single intravenous administration of abiraterone to rats, dogs and monkeys using WinNonlin Phoenix Version 8.2. The modelling was based on the assumptions of linear (dose-proportional) and time-invariant kinetics and that there was complete conversion of the abiraterone decanoate pro-drug to abiraterone. The function (representing one-compartment disposition with zero-order absorption) was WinNonlin Model 2 and the function (representing two-compartment disposition with zero-order absorption) was WinNonlin Model 10. Weighting was included, dependent on the pattern of residuals (residual Y versus predicted concentration or time) and precision of the estimated parameters. The appropriate model was selected based on: (i) visual inspection of the model fit to the data (ii) the lowest value of Akaike Information Criterion (AIC) and (iii) precision of the estimated parameters (CV). Systemic clearance (CL) and apparent volume of distribution ($V_{ss}$) were derived from the exponential functions.

Deconvolution: The rate and extent of input from an intramuscular administration was simulated by deconvolution using WinNonlin Phoenix Version 8.2. Deconvolution is based on linear systems analysis and is defined by the convolution integral: G(t)=R(t)*H(t). G(t) is the measured plasma concentration profile after intramuscular dosing, H(t) is represented by the exponential function described in Section 3.2 and R(t), the rate of input from the IM depot over time, is derived by deconvolution of the above expression. The slope of the input rate versus time generates the input rate constant (Koi). Integration of input rate versus time generates the cumulative input function and an estimate of absolute bioavailability.

Allometric scaling to man: The plasma concentration profile in man after intramuscular dosing was simulated based on the predictions of CL and Vss (to describe the disposition of abiraterone), and rate and extent of input (absorption) into systemic circulation (bioavailability). The disposition of abiraterone in animals was characterised by the PK parameters (CL and $V_{ss}$), derived from the exponential model. CL and $V_{ss}$ in man were predicted from CL and $V_{ss}$ in animals by an allometric approach. $V_{ss}=a \cdot W^x$ where a is the intercept, W is bodyweight and x is the allometric exponent; then, $\log V_{ss}=x \cdot \log W + \log a$ (derived from a log-log plot of body weight versus $V_{ss}$ in the 3 species). CL in man was derived by the data-driven method of Tang[5]; i.e. CLman/kg=0.407·CL monkeys/kg. The rate and extent of input was derived by deconvolution.

Results: A bi-exponential function was considered to best represent the plasma concentration-time profiles of abiraterone following single intravenous administration to rats, dogs and monkeys, respectively. Plasma clearance (CL) of abiraterone was 11414, 6469 and 2578 mL/h/kg in rats, dogs and monkeys, respectively. Apparent of volume of distribution at steady state ($V_{ss}$) of abiraterone was 22313, 14205 and 5732 mL/kg in rats, dogs and monkeys, respectively. See Table 12A below.

TABLE 12A

Summary of PK parameters of abiraterone in rats, dogs and monkeys following intravenous and intramuscular administration of abiraterone decanoate

| Species | CL (mL/h/kg) | Vss (mL/kg) | K01 (/h) | F (%) |
| --- | --- | --- | --- | --- |
| Rats | 11414 | 22313 | 0.00213 | 19 |
| Dogs | 6469 | 14205 | 0.00217 | 56 |
| Monkeys | 2578 | 5732 | 0.00213 | 14 |

Allometric scaling predicted CL (from monkeys only given the very high values of CL in rats and dogs) and $V_{ss}$ (from rats, dogs and monkeys) in man of 73 L/h and 437 L, respectively. The predicted $V_{ss}$ in man was appreciably greater than total body water volume (42 L), indicating extensive tissue distribution. The predicted CL in man was not appreciably different to hepatic blood flow (80 L/h).

Deconvolution of the IM profiles with the IV profiles provided estimations of the rate and extent of bioavailability of abiraterone. IM bioavailability in rats, dogs and monkeys was 19, 56 and 14%, respectively. The input (release from the IM depot) half-life after IM dosing in rats, dogs and monkeys was 325, 319 and 325 h, respectively.

Therefore, the parameters of CL (73 L/h), $V_{ss}$ (437 L), K01 (0.00213 h$^{-1}$) and F (56%) were used to simulate the plasma profile in man. See Table 12B, FIGS. 16A and 16B.

TABLE 12B

Predicted parameters of abiraterone in man following intramuscular administration of abiraterone decanoate*

| Parameter | Estimate |
| --- | --- |
| CL (L/h) | 73 |
| $V_{ss}$ (L) | 437 |
| K01 (/h) | 0.00213 |
| $t_{1/2}$ (h) | 325 |
| F (%) | 56 |

*Predictions assume a one-compartment disposition with first-order absorption model and linear kinetics in man.

Figure 16D:
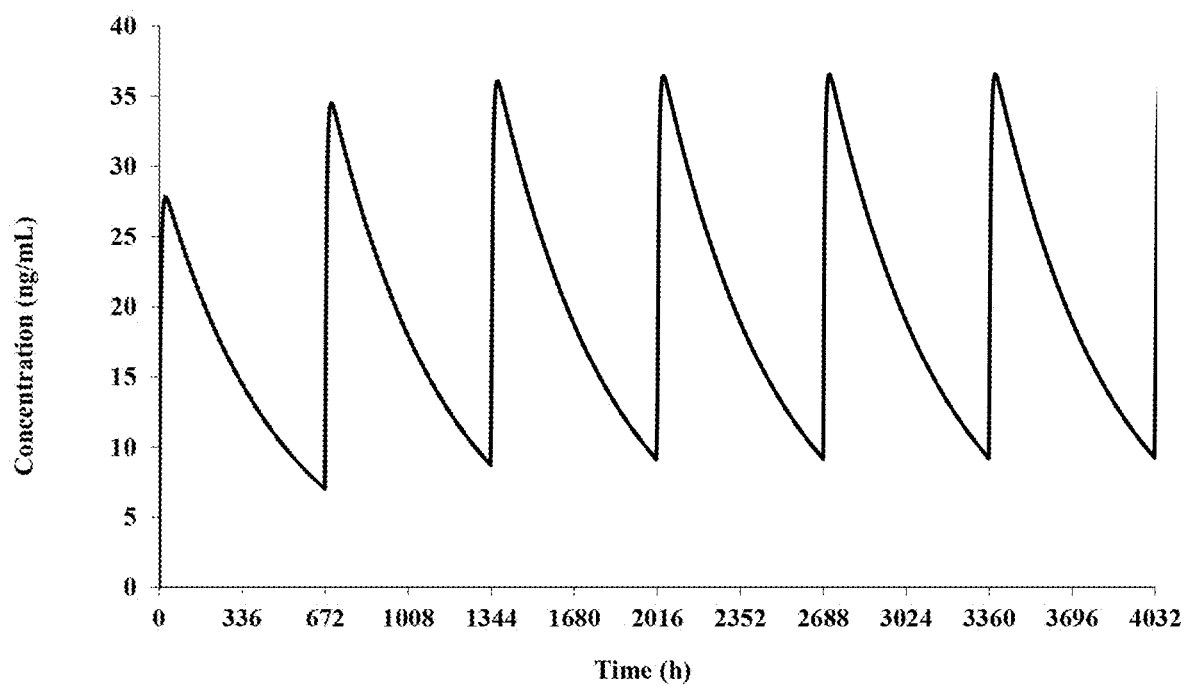
FIG. 16D shows predicted plasma profile of abiraterone in man following repeated intramuscular doses of abiraterone decanoate at 1000 mg every 4 weeks assuming complete bioavailability.

Following once monthly (i.e., every 4 weeks) intramuscular dose of abiraterone at 1000 mg to man, the predicted $C_{min}$ value was 5 ng/mL at steady state. See FIG. 16C. The inventors believe that human bioavailability of the once monthly intramuscular administration at this dosing level can be higher than the 56% used for the prediction in FIG. 16C and approaching complete bioavailability. Assuming complete bioavailability, the inventors believe that following once monthly intramuscular dose of abiraterone at 1000 mg to man, the predicted $C_{min}$ value would be 9.3 ng/mL at steady state. See FIG. 16D.

Conclusion: Volume of distribution ($V_{ss}$) in man (437 L) was predicted by allometry with adequate correlation between rats, dogs and monkeys. $V_{ss}$ indicates extensive tissue distribution in man. Systemic clearance (CL) in man (73 L/h) was predicted by allometry in monkeys. CL in man was not appreciably different to hepatic blood flow. Rate of absorption (absorption half-life of 325 h) and bioavailability (F of 56%) was predicted from deconvolution of intramuscular and intravenous data. Following once in four weeks intramuscular dose of abiraterone decanoate at 1000 mg to man, the predicted $C_{min}$ was 5 ng/mL at steady state.

Example 8. Studies of Abiraterone Isocaproate and Decanoate in Dogs

The objective of this study was to compare the pharmacokinetics (PK) of two different esters of abiraterone (isocaproate and decanoate) from intramuscular (IM) formulations following single administration to beagle dogs relative to a single intravenous (IV) formulation of abiraterone isocaproate used to enable calculation of absolute bioavailability of the isocaproate ester.

Naïve male beagle dogs were obtained from Marshall Bioresources, North Rose, NY for use in this study. The animals were 6-7 months old and weighed 7.0-7.9 kilograms at the time of first dose administration.

Two groups of three male dogs/group underwent standard evaluations such as body weight, clinical observations, and blood collection for PK. One group of three dogs were dosed on Day 1 via IV with abiraterone isocaproate (Test article #1, abiraterone isocaproate in 40% HP-beta-cyclodextrin). Following a minimum washout of 72 hours, all six dogs were dosed via IM. The three dogs that received the IV dose of abiraterone isocaproate were given the abiraterone isocaproate IM preparation (Test article #2, abiraterone isocaproate in 90% corn oil/10% benzyl alcohol) and the remaining three dogs were dosed with abiraterone decanoate IM preparation (Test article #3, abiraterone decanoate in 90% corn oil/10% benzyl alcohol). Doses were based on an assumed body weight of 10 kg, which could impact the calculated CL (or CL/F), Vz (or Vz/F) values, and the bioavailability assessment. The study design is summarized in the following table.

| Study Group | Test Article | Dose Route | Dose (mg/kg) | Dose Conc* (mg/mL) | Dose Volume (mL/kg) | Number of Animals |
|---|---|---|---|---|---|---|
| 1 | #1 | IV | 1.0 | 0.3 | 3.3 | 3 |
| 2 | #2 | IM | 77 | 158 | 0.49 | 3 |
| 3 | #3 | IM | 87 | 155 | 0.56 | 3 |

*Concentration of Prodrug.

Blood was collected predose and following IV administration, at 0.083, 0.1667, 0.25, 0.5, 0.75, 1, 2, 4, and 24 hours post dose administration. Blood was collected just prior to dosing and following IM administration, at 0.5, 1, 2, 3, 4, 5, 8, and 24 hours and 2, 3, 5, 7, 14, 21, 28, 35, and 49 days post dose administration (time of collection to approximate the time of dose administration). Blood was processed to plasma and the resulting plasma samples were analyzed for the prodrug and abiraterone.

Pharmacokinetic analyses were performed on plasma concentration versus time data using Phoenix WinNonlin (v 8.1) non-compartmental analysis function (linear trapezoidal rule for AUC calculations). See e.g., Example 5B.

Figure 17A:
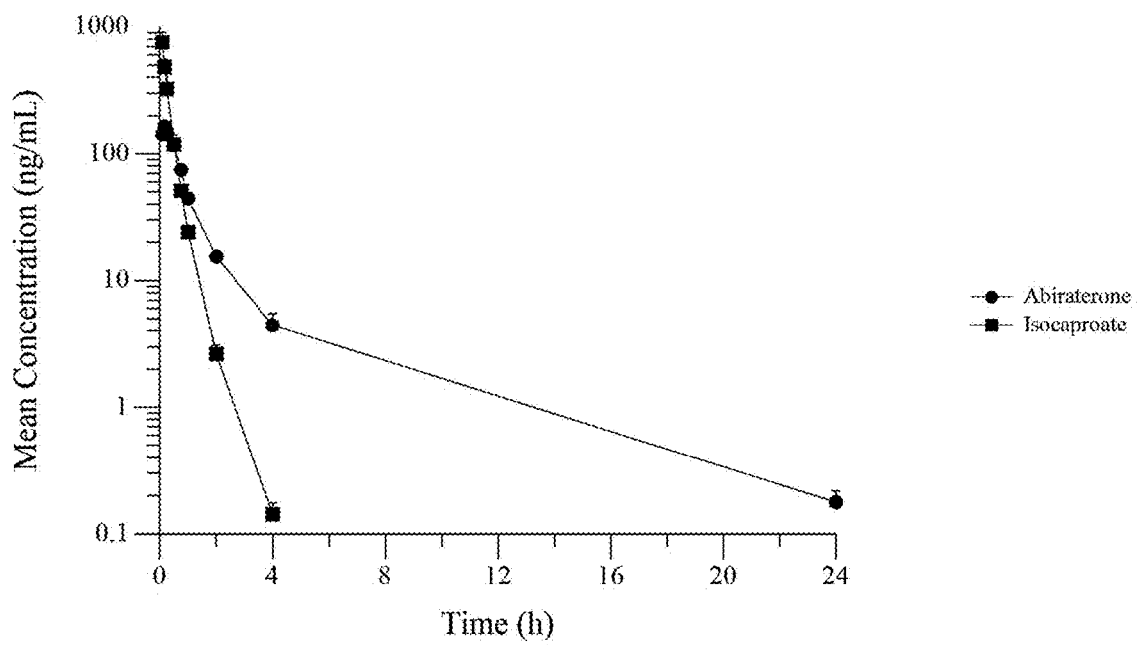
FIG. 17A shows mean abiraterone and abiraterone isocaproate plasma concentration versus time profile data following IV administration of 1.0 mg/kg abiraterone isocaproate in dogs. Error bars represent standard deviation.

Results: Single-Dose Pharmacokinetics of Abiraterone and Abiraterone Isocaproate Following IV Administration of 1 mg/kg Abiraterone Isocaproate: Evidence of systemic exposure to abiraterone and abiraterone isocaproate was observed in all treated dogs following IV administration (Table 13A and FIG. 17A). Following IV administration of abiraterone isocaproate (pro-drug), a mean CL value of 62.8 mL/min/kg was calculated for the prodrug, which was considered high clearance. Using a dose value of 0.78 mg/kg (assuming 100% conversion of the prodrug to abiraterone) the mean CL/F value was 63.3 mL/min/kg for abiraterone. The mean Vz value was 1.91 L/kg for the pro-drug and the mean Vz/F value 4.22 L/kg for abiraterone. The mean $t_{1/2}$ value for the prodrug and abiraterone was 0.350 hours and 0.773 hours, respectively.

Figure 17B:
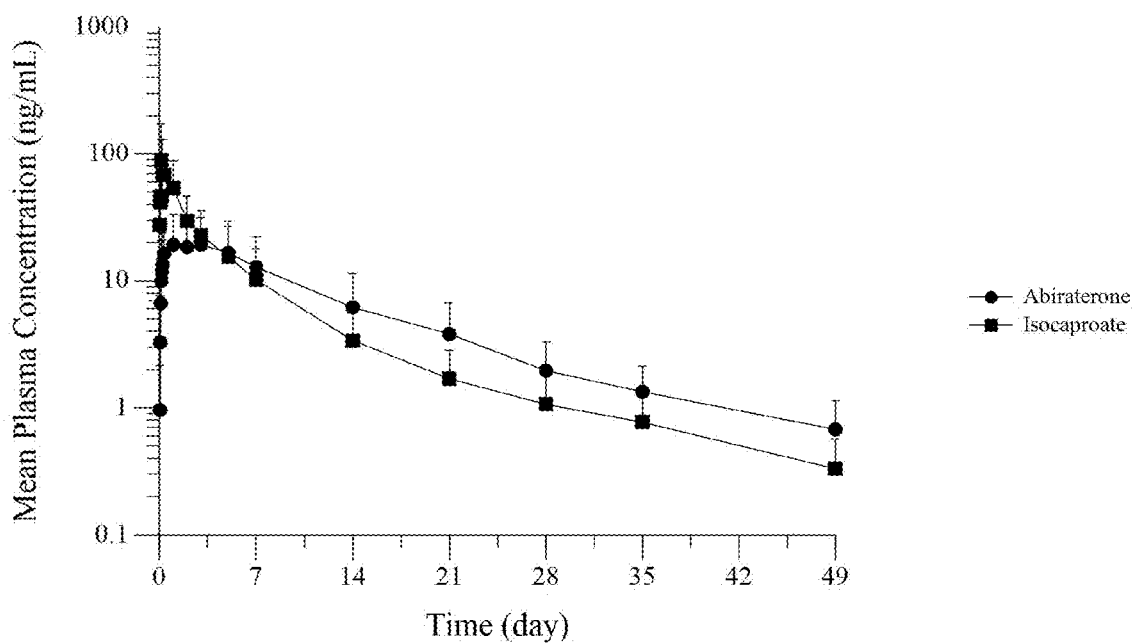
FIG. 17B shows mean abiraterone and abiraterone isocaproate plasma concentration versus time profile data following IM administration of abiraterone isocaproate in dogs. Error bars represent standard deviation.

Single-Dose Pharmacokinetics of Abiraterone and Abiraterone Isocaproate Following IM Administration of Abiraterone Isocaproate: Evidence of systemic exposure to abiraterone and abiraterone isocaproate was observed in all treated dogs following IM administration (Table 13B and FIG. 17B), although it should be noted that there was high variability in exposure parameters ($C_{max}$ and AUC values) as CV % values ranged between 60 to 70%. Following IM administration, mean $T_{max}$ values were 1.7 and 0.19 days for abiraterone and the isocaproate prodrug, respectively. The mean $C_{max}$ values were 20.2 and 106 ng/mL for abiraterone and the isocaproate prodrug, respectively. The mean $AUC_{last}$ values were 266 and 281 day*ng/mL for abiraterone and the isocaproate prodrug, respectively. The mean $t_{1/2}$ values were 9.3 and 7.4 days for abiraterone and the isocaproate prodrug, respectively.

Estimates of the absolute bioavailability for abiraterone were calculated using the mean $AUC_{INF}$ values following 0.78 mg/kg IV abiraterone isocaproate administration (206 h*ng/mL, or 131 h*ng/mL when corrected for dose) and 60 mg/kg IM administration of abiraterone isocaproate (corrected for dose and time units=114 h*ng/mL). The estimated abiraterone bioavailability from the isocaproate ester was calculated at 87%, although these data should be interpreted with caution since the dose was based on an assumed body weight of 10 kg.

Figure 17C:
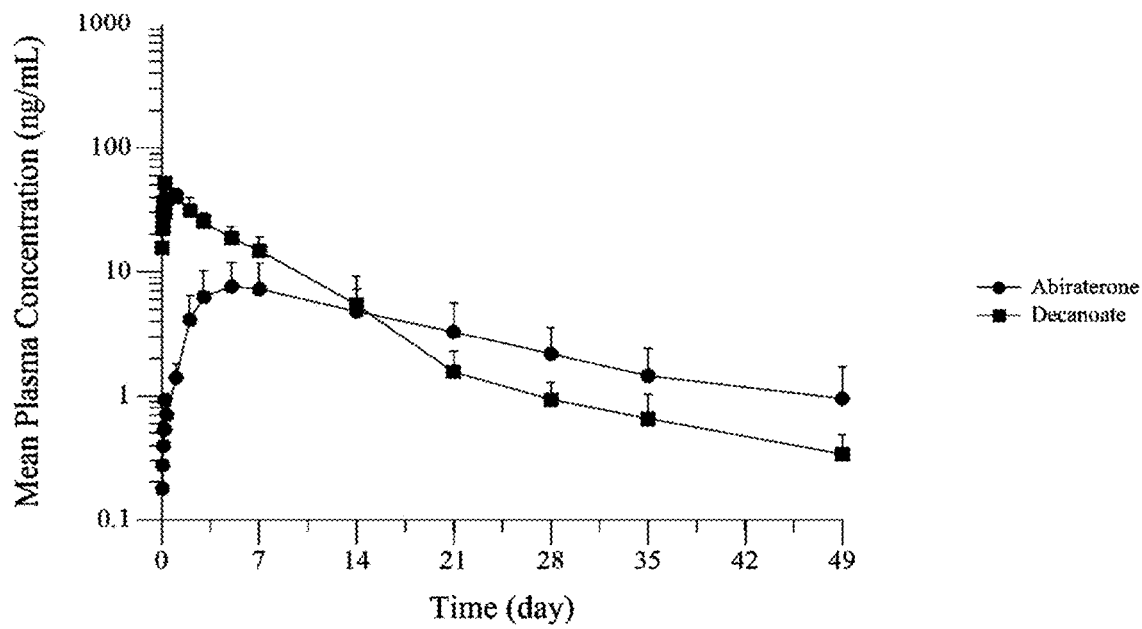
FIG. 17C shows mean abiraterone and abiraterone decanoate plasma concentration versus time profile data following IM administration of abiraterone decanoate in dogs. Error bars represent standard deviation.
Figure 17D:
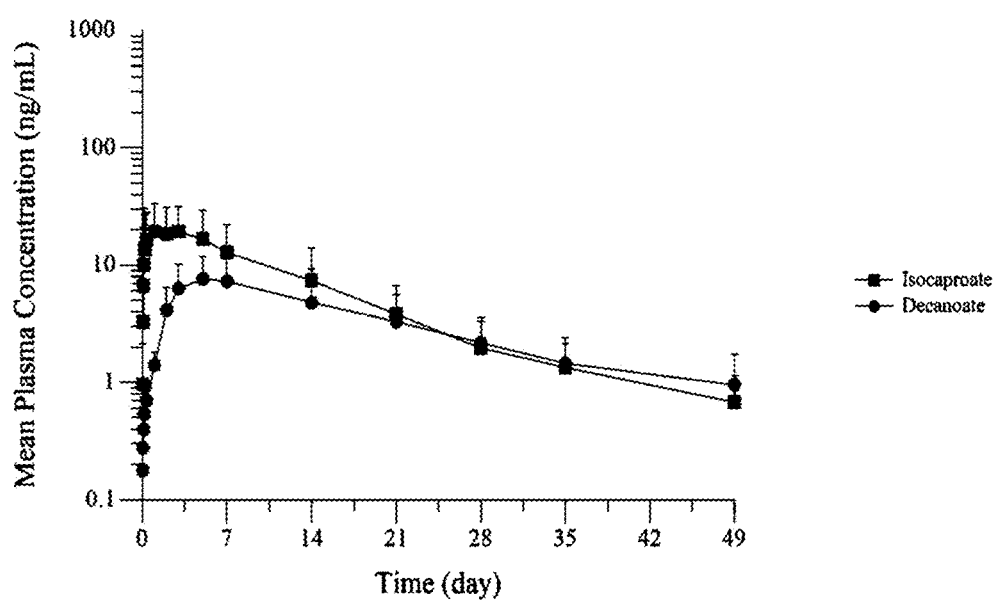
FIG. 17D shows mean abiraterone plasma concentration versus time profile data following IM administration of abiraterone isocaproate or decanoate in dogs. Error bars represent standard deviation.

Single-Dose Pharmacokinetics of Abiraterone and Abiraterone Decanoate Following IM Administration of Abiraterone Decanoate: Evidence of systemic exposure to abiraterone and abiraterone decanoate was observed in all treated dogs following IM administration (Table 13B and FIG. 17C). The variability in abiraterone exposure parameters ($C_{max}$ and AUC values) was between 60 to 70%, while the decanoate exposure parameters had low variability with CV % values of <27%. Following IM administration, the mean $T_{max}$ values were 5.7 and 0.71 days for abiraterone and the decanoate prodrug, respectively. The mean $C_{max}$ values were 7.82 and 45.0 ng/mL for abiraterone and the decanoate prodrug, respectively. The mean $AUC_{last}$ values were 176 and 298 day*ng/mL for abiraterone and the decanoate prodrug, respectively. The mean $t_{1/2}$ values were 14 and 6.7 days for abiraterone and the decanoate prodrug, respectively. Estimates of the absolute bioavailability for abiraterone are calculated using the mean $AUC_{INF}$ values following 0.86 mg/kg IV administration of abiraterone decanoate (145 h*ng/mL, or 169 h*ng/mL when corrected for dose) and 60 mg/kg IM administration (corrected for dose and time units=70.4 h*ng/mL). The estimated abiraterone bioavailability was calculated at 42%, although these data should be interpreted with caution since the dose was based on an assumed body weight of 10 kg. The comparison of mean abiraterone plasma concentration profile following IM administration of abiraterone isocaproate or abiraterone decanoate is shown in FIG. 17D.

TABLE 13A

Summary Abiraterone or Abiraterone Isocaproate Plasma PK Parameters Following IV Administration in Dogs.

| Analyte | Dose (mg/kg) | | $T_{max}$ (h) | $C_{max}$ (ng/mL) | $AUC_{0-4}$ (h * ng/mL) | $AUC_{last}$ (h * ng/mL) | $AUC_{INF}$ (h * ng/mL) | Vz or Vz/F (L/kg) | CL or CL/F (mL/min/kg) | $t_{1/2}$ (h) |
|---|---|---|---|---|---|---|---|---|---|---|
| Abiraterone | 0.78 | N | 3 | 3 | 3 | 3 | 3 | 3 | 3 | 3 |
| | | Mean | 0.17 | 165 | 159 | 206 | 206 | 4.22 | 63.3 | 0.773 |
| | | SD | 0.0 | 17.2 | 3.48 | 12.5 | 12.5 | 0.125 | 3.85 | 0.0653 |
| | | CV % | 0.00 | 10.5 | 2.18 | 6.08 | 6.09 | 2.97 | 6.08 | 8.45 |
| Isocaproate | 1.0 | N | 3 | 3 | 3 | 3 | 3 | 3 | 3 | 3 |
| | | Mean | 0.083 | 751 | 269 | 269 | 269 | 1.91 | 62.8 | 0.350 |
| | | SD | 0.0 | 158 | 40.0 | 40.0 | 40.0 | 0.349 | 8.61 | 0.0228 |
| | | CV % | 0.00 | 21.0 | 14.9 | 14.9 | 14.9 | 18.3 | 13.7 | 6.52 |

TABLE 13B

Summary Abiraterone or Abiraterone Prodrug Plasma PK Parameters Following IM Administration in Dog

| Group | Analyte | | $T_{max}$ (d) | $C_{max}$ (ng/mL) | $AUC_{last}$ (d * ng/mL) | $AUC_{INF}$ (d * ng/mL) | Vz/F (L/kg) | CL/F (mL/min/kg) | $t_{1/2}$ (d) |
|---|---|---|---|---|---|---|---|---|---|
| 2 | Isocaproate | N | 3 | 3 | 3 | 3 | 3 | 3 | 3 |
| | | Mean | 0.19 | 106 | 2.81 | 285 | 3640 | 238 | 7.40 |
| | | SD | 0.12 | 67.2 | 186 | 188 | 1950 | 114 | 1.36 |
| | | CV % | 61.9 | 63.5 | 66.1 | 65.9 | 53.6 | 47.8 | 18.4 |
| 2 | Abiraterone | N | 3 | 3 | 3 | 3 | 3 | 3 | 3 |
| | | Mean | 1.7 | 20.2 | 266 | 275 | 3910 | 201 | 9.31 |
| | | SD | 1.2 | 13.2 | 192 | 197 | 2060 | 105 | 0.845 |
| | | CV % | 69.3 | 65.4 | 72.2 | 71.6 | 52.7 | 52.4 | 9.07 |
| 3 | Decanoate | N | 3 | 3 | 3 | 3 | 3 | 3 | 3 |
| | | Mean | 0.71 | 45.0 | 295 | 299 | 2850 | 207 | 6.68 |
| | | SD | 0.51 | 12.0 | 50.2 | 51.4 | 426 | 38.0 | 0.723 |
| | | CV % | 71.3 | 26.6 | 17.0 | 17.2 | 15.0 | 18.4 | 10.8 |
| 3 | Abiraterone | N | 3 | 3 | 3 | 3 | 3 | 3 | 3 |
| | | Mean | 5.7 | 7.82 | 157 | 176 | 10900 | 386 | 13.8 |
| | | SD | 1.2 | 4.48 | 105 | 121 | 9600 | 350 | 0.466 |
| | | CV % | 20.4 | 57.3 | 67.1 | 68.8 | 88.1 | 90.5 | 3.37 |

Conclusion of Example 8: Evidence of systemic exposure to abiraterone was observed in all treated dogs following dose administration. Comparison of the mean $T_{max}$ and $C_{max}$ values suggest that the isocaproate prodrug is more rapidly absorbed, with shorter $T_{max}$ values and higher $C_{max}$ values relative to the decanoate prodrug. Mean abiraterone AUC values appeared to be less than 2-fold higher following IM administration of the isocaproate pro-drug when compared to the decanoate prodrug. The long half-life values observed following IM administration relative to those values observed following IV administration suggests that the prodrug has a slow release/absorption profile when administered via the IM route. There was some evidence that abiraterone half-life appeared to be longer following the decanoate administration, which is likely due to the slower absorption of the decanoate prodrug.

Each reference referred to within this disclosure is hereby incorporated in its respective entirety.

As used herein, the term "about" modifying an amount related to the disclosure refers to variation in the numerical quantity that can occur, for example, through routine testing and handling; through inadvertent error in such testing and handling; through differences in the manufacture, source, or purity of ingredients/materials employed in the disclosure; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

With respect to aspects of the disclosure described as a genus, all individual species are individually considered separate aspects of the disclosure. If aspects of the disclosure are described as "comprising" a feature, embodiments also are contemplated "consisting of" or "consisting essentially of" the feature.

All of the various aspects, embodiments, and options described herein can be combined in any and all variations.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

We claim:

1. A crystalline form of a compound having the following formula,

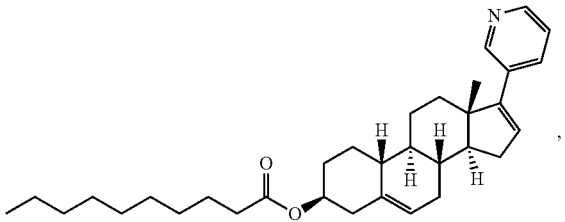

wherein the crystalline form is characterized by an X-Ray Powder Diffraction (XRPD) spectrum having one or more of the following peaks: 4.6, 6.9, 8.7, 17.5, 18.3, 18.6, 19.1, 19.6, and 20.8, degrees 2 theta, ±0.2°.

2. The crystalline form of claim 1, characterized by an XRPD spectrum having all of the following peaks: 4.6, 6.9, 8.7, 17.5, 18.3, 18.6, 19.1, 19.6, and 20.8, degrees 2 theta, ±0.2°.

3. The crystalline form of claim 1, characterized by an XRPD spectrum substantially the same as shown in FIG. 12A.

4. The crystalline form of claim 1, further characterized by a Differential Scanning calorimetry (DSC) pattern having an endothermic peak with an onset temperature at about 69.0° C.

5. The crystalline form of claim 2, further characterized by a Differential Scanning calorimetry (DSC) pattern having an endothermic peak with an onset temperature at about 69.0° C.

6. The crystalline form of claim 3, further characterized by a Differential Scanning calorimetry (DSC) pattern having an endothermic peak with an onset temperature at about 69.0° C.

7. A substantially pure compound having the following formula,

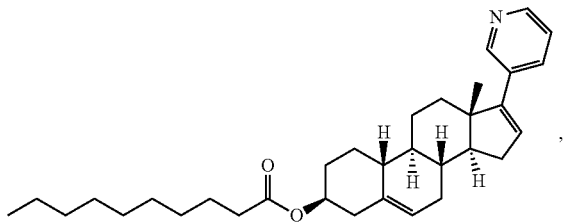

characterized as having a purity by weight of greater than 95%.

8. The substantially pure compound of claim 7, characterized as having a purity by weight of greater than 98%.

9. The substantially pure compound of claim 7, characterized as having a purity by weight of greater than 99%.

10. The substantially pure compound of claim 7, which is in a solid form.

11. The substantially pure compound of claim 10, which is in a crystalline form characterized by an X-Ray Powder Diffraction (XRPD) spectrum having one or more of the following peaks: 4.6, 6.9, 8.7, 17.5, 18.3, 18.6, 19.1, 19.6, and 20.8, degrees 2 theta, =0.2°.

12. The substantially pure compound of claim 10, which is in a crystalline form characterized by an X-Ray Powder Diffraction (XRPD) spectrum having all of the following peaks: 4.6, 6.9, 8.7, 17.5, 18.3, 18.6, 19.1, 19.6, and 20.8, degrees 2 theta, ±0.2°.

13. The substantially pure compound of claim 10, which is in a crystalline form characterized by an XRPD spectrum substantially the same as shown in FIG. 12A.

14. The substantially pure compound of claim 11, wherein the crystalline form is further characterized by a Differential Scanning calorimetry (DSC) pattern having an endothermic peak with an onset temperature at about 69.0° C.

15. The substantially pure compound of claim 12, wherein the crystalline form is further characterized by a Differential Scanning calorimetry (DSC) pattern having an endothermic peak with an onset temperature at about 69.0° C.

16. The substantially pure compound of claim 13, wherein the crystalline form is further characterized by a Differential Scanning calorimetry (DSC) pattern having an endothermic peak with an onset temperature at about 69.0° C.

17. A salt of a compound having the following formula,

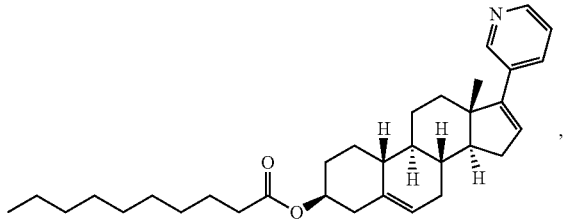

wherein the salt is an oxalate salt, a hydrochloride salt, a benzene sulfonate salt, a p-toluene sulfonate salt, or a phosphate salt.

18. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 7 with a pharmaceutically acceptable carrier.

19. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 8 with a pharmaceutically acceptable carrier.

20. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 9 with a pharmaceutically acceptable carrier.

21. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 10 with a pharmaceutically acceptable carrier.

22. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 11 with a pharmaceutically acceptable carrier.

23. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 12 with a pharmaceutically acceptable carrier.

24. A method of preparing a pharmaceutical composition suitable for parenteral administration to a subject having a sex hormone-dependent benign or malignant disorder, a syndrome due to androgen excess, and/or a syndrome due to glucocorticoid excess, comprising mixing the substantially pure compound of claim 13 with a pharmaceutically acceptable carrier.

25. The method of claim 18, wherein the pharmaceutically acceptable carrier comprises a pharmaceutically acceptable oil and optionally a pharmaceutically acceptable solvent.

26. The method of claim 18, wherein the pharmaceutically acceptable carrier comprises a pharmaceutically acceptable oil and a pharmaceutically acceptable solvent.

27. The method of claim 26, wherein the pharmaceutically acceptable oil comprises a vegetable oil, castor oil, corn oil, sesame oil, cottonseed oil, peanut oil, poppy seed oil, tea seed oil, or soybean oil, the pharmaceutically acceptable solvent comprises benzyl alcohol and/or benzyl benzoate.

28. A pharmaceutical composition comprising the crystalline form of claim 1.

29. A pharmaceutical composition comprising the crystalline form of claim 2.

30. A pharmaceutical composition comprising the crystalline form of claim 3.

31. The pharmaceutical composition prepared by the method of claim 18.

32. The pharmaceutical composition prepared by the method of claim 25.

33. The pharmaceutical composition prepared by the method of claim 26.

34. The pharmaceutical composition prepared by the method of claim 27.

\* \* \* \* \*